(12) United States Patent
Alexander et al.

(10) Patent No.: US 11,913,016 B2
(45) Date of Patent: Feb. 27, 2024

(54) SYNTHETIC YEAST CELLS AND METHODS OF MAKING AND USING THE SAME

(71) Applicant: Wisconsin Alumni Research Foundation, Madison, WI (US)

(72) Inventors: William Gerald Alexander, Madison, WI (US); David Peris Navarro, Madison, WI (US); Christopher Todd Hittinger, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 15/805,950

(22) Filed: Nov. 7, 2017

(65) Prior Publication Data

US 2018/0127784 A1    May 10, 2018

Related U.S. Application Data

(60) Provisional application No. 62/524,700, filed on Jun. 26, 2017, provisional application No. 62/418,444, filed on Nov. 7, 2016.

(51) Int. Cl.
| | |
|---|---|
| *C12N 15/90* | (2006.01) |
| *C12N 15/81* | (2006.01) |
| *C12N 1/18* | (2006.01) |
| *C12N 15/65* | (2006.01) |
| *C12N 9/16* | (2006.01) |

(52) U.S. Cl.
CPC ............ *C12N 15/905* (2013.01); *C12N 1/18* (2013.01); *C12N 9/16* (2013.01); *C12N 15/65* (2013.01); *C12N 15/81* (2013.01); *C12N 2800/80* (2013.01); *C12N 2840/002* (2013.01)

(58) Field of Classification Search
CPC ........ C12N 15/905; C12N 1/18; C12N 15/65; C12N 15/81; C12N 2800/80; C12N 2840/002
See application file for complete search history.

(56) References Cited

U.S. PATENT DOCUMENTS

2012/0252061 A1* 10/2012 Bavouzet .............. C12N 1/18
  435/34
2015/0307868 A1* 10/2015 Nicolas .................. C12N 9/90
  506/2

OTHER PUBLICATIONS

Czaja et al., (2011) Genetics, vol. 189, pp. 795-808. (Year: 2011).*
Schwartz et al. (2012) APJ1 and GRE3 Homologs Work in Concert to Allow Growth in Xylose in a Natural *Saccharomyces* sensu stricto Hybrid Yeast. Genetics, 191:621-632 (Year: 2012).*
Dani et al. (1983) Mitotic and meiotic stability of linear plasmids in yeast. PNAS, 80:3406-3410 (Year: 1983).*
Steensels et al. (2014) Improving industrial yeast strains: exploiting natural and artificial diversity. FEMS Microbiology Review, 38: 947-995 (Year: 2014).*
Wang et al. (2012) The combination of glycerol metabolic engineering and drug resistance marker-aided genome shuffling to improve very-high-gravity fermentation performances of industrial *Saccharomyces cerevisiae*. Bioresource Technology, 108:203-210 (Year: 2012).*
Pfliegler et al. (2012) Double sterility barrier between *Saccharomyces* species and its breakdown in allopolyploid hybrids by chromosome loss. FEMS Yeast Research, 12:703-718. (Year: 2012).*
Tani et al. (1993) A Novel Method for Breeding Polyploid Cells by Heat-induced Endomitotic Diploidization in *Saccharomyces cerevisiae*. Bioscience, Biotechnology, and Biochemistry, 57(12):2063-2066 (Year: 1993).*
Peris et al. (2020) Synthetic hybrids of six yeast species. Nature Communications, 11:2085, pp. 1-11 and Supplementary Information (Year: 2020).*
Dujon, B. "Yeasts illustrate the molecular mechanisms of eukaryotic genome evolution" 2006 Trends in Genetics 22(7):375-387.
Herskowitz, I. & Jensen, R.E. "Putting the HO Gene to Work: Practical Uses for Mating-Type Switching" 1991 Methods Enzymol. 194:132-146.
Kronstad, J.W. & Staben, C. "Mating Type in Filamentous Fungi" 1997 Annu. Rev. Genet. 31:245-276.
Pérez-Través, L., et al. "Evaluation of different genetic procedures for the generation of artificial hybrids in *Saccharomyces* genus for winemaking" 2012 International Journal of Food Microbiology 156:102-111.
Peris, D., et al. "Population structure and reticulate evolution of *Saccharomyces eubayanus* and its lager-brewing hybrids" 2014 Molecular Ecology 23:2031-2045.
Alexander, et al. 2016. Efficient engineering of marker-free synthetic allotetraploids of *Saccharomyces*. Fungal Genet Biol. Apr. 2016;89:10-17.
Bardwell, L., 2005. A walk-through of the yeast mating pheromone response pathway. Peptides 26, 339-350.
Bullard, et al. 2010. Polygenic and directional regulatory evolution across pathways in *Saccharomyces*. Proc. Natl. Acad. Sci. U. S. A. 107, 5058-63.
Casselton, L.A., Olesnicky, N.S., 1998. Molecular genetics of mating recognition in basidiomycete fungi. Microbiol. Mol. Biol. Rev. 62, 55-70.
Dunn, B., Sherlock, G., 2008. Reconstruction of the genome origins and evolution of the hybrid lager yeast *Saccharomyces pastorianus*. Genome Res. 18, 1610-1623.
Frank-Vaillant, M., Marcand, S., 2001. NHEJ regulation by mating type is exercised through a novel protein, Lif2p, essential to the ligase IV pathway. Genes Dev. 15, 3005-12.

(Continued)

*Primary Examiner* — Neil P Hammell
*Assistant Examiner* — Douglas Charles Ryan
(74) *Attorney, Agent, or Firm* — Quarles & Brady, LLP

(57) ABSTRACT

Methods of making synthetic yeast cells by mating together two diploid (or higher ploidy) yeast species or hybrids to generate multi-ploid yeast hybrids are provided herein. The synthetic yeast cells made by this process and kits for performing the process are also provided.

**18 Claims, 15 Drawing Sheets
(14 of 15 Drawing Sheet(s) Filed in Color)
Specification includes a Sequence Listing.**

(56) References Cited

OTHER PUBLICATIONS

Garí, E., et al. 1997. A set of vectors with a tetracycline-regulatable promoter system for modulated gene expression in *Saccharomyces cerevisiae*. Yeast 13, 837-48.

Gerstein, et al. 2006. Genomic convergence toward diploidy in *Saccharomyces cerevisiae*. PLoS Genet. 2, e145.

Glass, N.L., Grotelueschen, J., Metzenberg, R.L., 1990. Neurospora crassa A mating-type region. Proc. Natl. Acad. Sci. U. S. A. 87, 4912-4916.

González, S.S., Barrio, E., Querol, A., 2008. Molecular characterization of new natural hybrids of *Saccharomyces cerevisiae* and S. kudriavzevii in brewing. Appl. Environ. Microbiol. 74, 2314-2320.

Greig, D., Borts, R.H., Louis, E.J., Travisano, M., 2002. Epistasis and hybrid sterility in *Saccharomyces*. Proc. Biol. Sci. 269, 1167-71.

Gunge, N., 1966. Breeding of bakers' yeast-Determination of the ploidy and an attempt to improve practical properties. Japanese J. Genet. 41, 203-214.

Haber, J.E., 2012. Mating-type genes and MAT switching in *Saccharomyces cerevisiae*. Genetics 191, 33-64.

Hebly, et al. 2015. *S. cerevisiae* x S. eubayanus interspecific hybrid, the best of both worlds and beyond. FEMS Yeast Res. 15.

Husnik, J.I., Volschenk, H., Bauer, J., Colavizza, D., Luo, Z., van Vuuren, H.J.J., 2006. Metabolic engineering of malolactic wine yeast. Metab. Eng. 8, 315-23.

Jensen, R.E., Herskowitz, I., 1984. Directionality and regulation of cassette substitution in yeast. Cold Spring Harb. Symp. Quant. Biol. 49, 97-104.

Krogerus, K., Magalhães, F., Vidgren, V., Gibson, B., 2015. New lager yeast strains generated by interspecific hybridization. J. Ind. Microbiol. Biotechnol. 42, 769-78.

Le Jeune, et al. 2007. Characterization of natural hybrids of *Saccharomyces cerevisiae* and *Saccharomyces bayanus* var. uvarum. FEMS Yeast Res. 7, 540-9.

Maclean, C.J., Greig, D., 2008. Prezygotic reproductive isolation between *Saccharomyces cerevisiae* and *Saccharomyces paradoxus*. BMC Evol. Biol. 8, 1.

Masneuf, et al. 1998. New hybrids between *Saccharomyces* sensu stricto yeast species found among wine and cider production strains. Appl. Envir. Microbiol. 64, 3887-3892.

Nakao, et al. 2009. Genome sequence of the lager brewing yeast, an interspecies hybrid. DNA Res. 16, 115-29.

Pérez-Través, et al. 2014a. Stabilization process in *Saccharomyces* intra and interspecific hybrids in fermentative conditions. Int. Microbiol. 17, 213-24.

Peris, et al. 2012a. The molecular characterization of new types of *Saccharomyces cerevisiae* x S. kudriavzevii hybrid yeasts unveils a high genetic diversity. Yeast 29, 81-91.

Peris, et al. 2012c. Comparative genomics among *Saccharomyces cerevisiae* x *Saccharomyces kudriavzevii* natural hybrid strains isolated from wine and beer reveals different origins. BMC Genomics.

Peris, et al. 2017. Hybridization and adaptive evolution of diverse *Saccharomyces* species for cellulosic biofuel production. Biotechnol Biofuels. Mar. 27, 2017;10:78.

Peris, et al. 2012b. Reconstruction of the evolutionary history of *Saccharomyces cerevisiae* x S. kudriavzevii hybrids based on multilocus sequence analysis. PLoS One 7, e45527.

Piatkowska, et al. 2013. Chimeric protein complexes in hybrid species generate novel phenotypes. PLoS Genet. 9, e1003836.

Piotrowski, et al. 2012. Different selective pressures lead to different genomic outcomes as newly-formed hybrid yeasts evolve. BMC Evol. Biol. 12, 46.

Russell, et al. 1986. Structure of the *Saccharomyces cerevisiae* HO gene and analysis of its upstream regulatory region. Mol. Cell. Biol. 6, 4281-94.

Schwartz, et al. 2012. APJ1 and GRE3 homologs work in concert to allow growth in xylose in a natural *Saccharomyces* sensu stricto hybrid yeast. Genetics 191, 621-32.

Selmecki, et al. 2015. Polyploidy can drive rapid adaptation in yeast. Nature 519, 349-52.

Staben, C., Yanofsky, C., 1990. Neurospora crassa a mating-type region. Proc. Natl. Acad. Sci. U. S. A. 87, 4917-21.

Storchova, Z., 2014. Ploidy changes and genome stability in yeast. Yeast 31, 421-30.

Swain Lenz, D., Riles, L., Fay, J.C., 2014. Heterochronic meiotic misexpression in an interspecific yeast hybrid. Mol. Biol. Evol. 31, 1333-1342.

Tirosh, I., Reikhav, S., Levy, A.A., Barkai, N., 2009. A yeast hybrid provides insight into the evolution of gene expression regulation. Science 324, 659-62.

Walker, et al. 2003. Application of the reuseable, KanMX selectable marker to industrial yeast: Construction and evaluation of heterothallic wine strains of *Saccharomyces cerevisiae*, possessing minimal foreign DNA sequences. FEMS Yeast Res. 4, 339-347.

\* cited by examiner

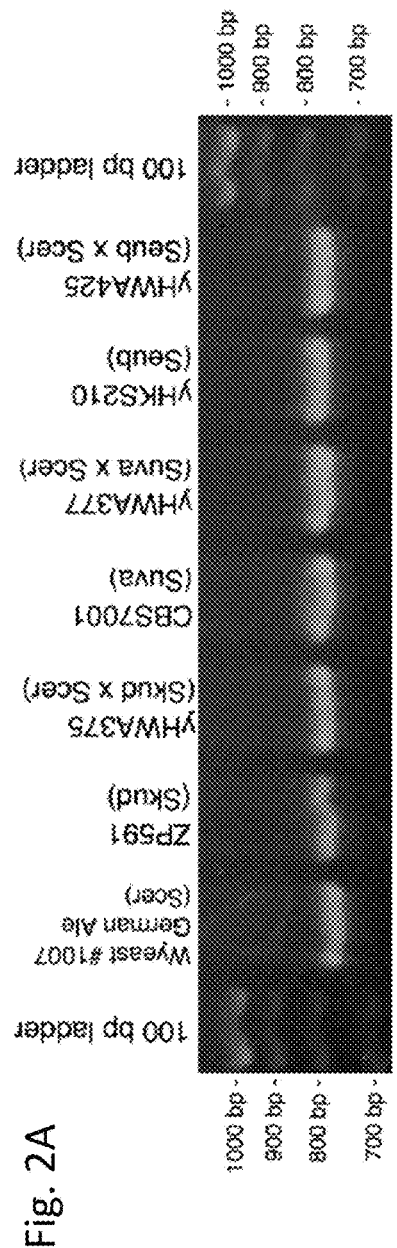
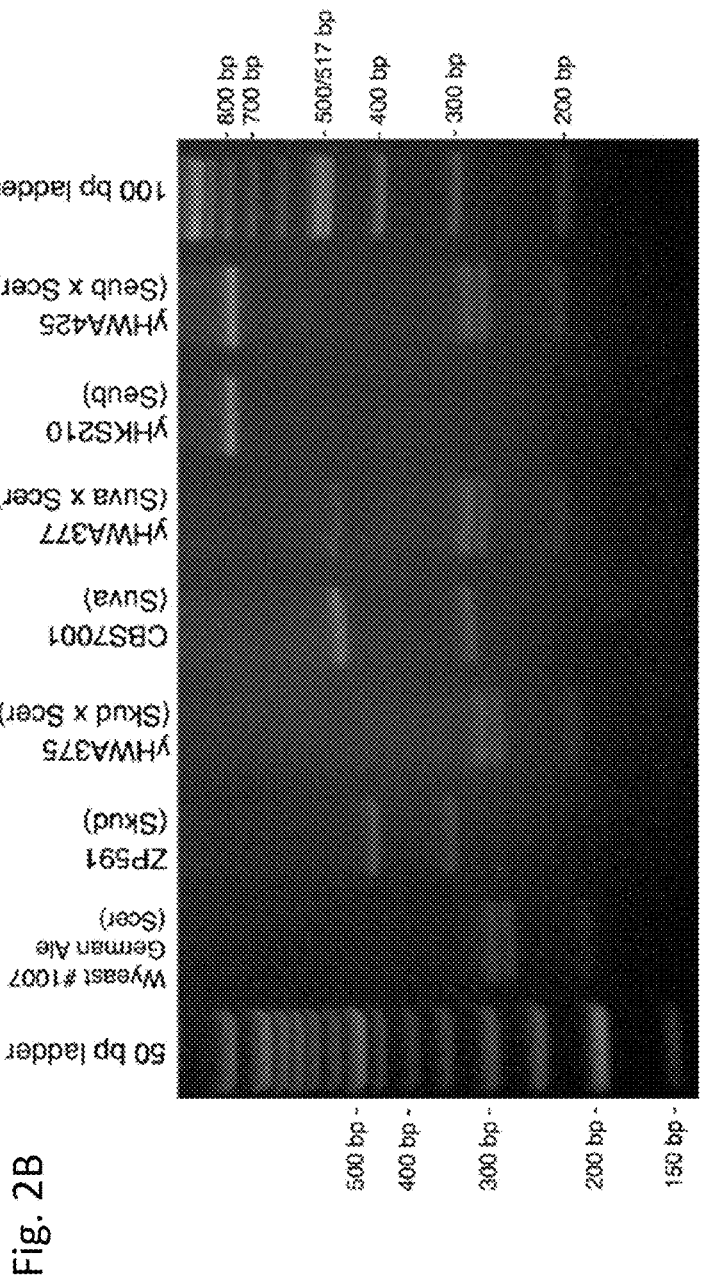
Fig. 2A
Fig. 2B

SYNTHETIC YEAST CELLS AND METHODS OF MAKING AND USING THE SAME

CROSS-REFERENCE TO RELATED APPLICATIONS

This patent application claims the benefit of priority of U.S. Provisional Patent Application No. 62/418,444, filed Nov. 7, 2016 and United States Provisional Patent Application No. 62/524,700, filed Jun. 26, 2017, both of which are incorporated herein by reference in their entireties.

STATEMENT REGARDING FEDERALLY SPONSORED RESEARCH

This invention was made with United States government support under grant number DE-FC02-07ER64494 awarded by the US Department of Energy and 1253634 awarded by the National Science Foundation. The government has certain rights in this invention.

SEQUENCE LISTING

This application is being filed electronically via EFS-Web and includes an electronically submitted Sequence Listing in .txt format. The .txt file contains a sequence listing entitled "2017-11-07 5671-00073_ST25.txt" created on Nov. 7, 2017 and is 39,919 bytes in size. The Sequence Listing contained in this .txt file is part of the specification and is hereby incorporated by reference herein in its entirety.

INTRODUCTION

Yeasts are critical biocatalysts commonly used in many types of commercial fermentations. One potential way of developing new yeast biocatalysts takes advantage of the natural mechanism of reproduction exhibited by many yeast species. For example, numerous yeast species are able to reproduce sexually, wherein meiosis serves to both increase genetic diversity and to repair genetic material. As with other eukaryotes, yeast meiosis generally initiates in diploid cells (John, 1990). Regulation of this process involves specialized genetic loci called the mating-type (MAT) loci. Among yeast species, *Saccharomyces* yeast species, for example, possess two different mating type loci, MATa and MATα, which each may contain two different genes. These mating-type genes encode transcription factors that regulate the expression of meiosis-specific genes, as well as other genes that function in self-recognition, pheromone production, and non-homologous end joining.

In addition to performing sexual reproduction among members of the same species ("intraspecies sexual reproduction"), *Saccharomyces* yeasts may also perform sexual reproduction among members of different species ("interspecies sexual reproduction"). All seven species of *Saccharomyces* yeasts possess the same mating-type locus organization and a predominantly diploid or diplontic lifestyle. Only limited pre-zygotic speciation barriers exist between *Saccharomyces* species, making hybridization possible between different *Saccharomyces* yeast species ("interspecies hybrids").

Interestingly, interspecies yeast hybrids produce many commercially important fermentation products. For example, *Saccharomyces cerevisiae*×*Saccharomyces eubayanus* hybrids are used to produce lager beer, the most common fermented beverage on the planet (Conan, 1975; Libkind et al., 2011). Two major lineages are used in lager production (Dunn and Sherlock, 2008; Nakao et al., 2009; Walther et al., 2014), and recent evidence indicates that these two lineages arose from independent hybridization events, suggesting that genetic diversity from the parental populations may be one contributor to the phenotypic differences seen in modern industrial strains (Baker et al., 2015). Many other fermented beverages also make use of *Saccharomyces* hybrids: *S. cerevisiae*×*Saccharomyces uvarum* hybrids are used in production of some ciders and cold-fermented wines (Le Jeune et al., 2007; Masneuf et al., 1998; Perez-Través et al., 2014b), while many Belgian ale and some European wine yeasts are *S. cerevisiae*×*Saccharomyces kudriavzevii* hybrids (Peris et al., 2012a, 2012b).

Given the importance of interspecies yeast hybrids in many commercial fermentations, there is an interest in the art of developing new synthetic interspecies hybrids that may possess novel properties and allow for strain improvement. However, current methods for making synthetic interspecies hybrids are cumbersome and/or require genomic modifications. New hybrid brewing strains have been generated by a laborious process of isolating auxotrophic mutants, which arise spontaneously at low frequency, followed by sporulation, dissection, and crossing MAT-compatible spores to obtain hybrids (Krogerus et al., 2015; Pérez-Través et al., 2012). Although these methods lack markers, which would likely streamline approval for food and beverage applications, the strains contain mutations in important biosynthetic pathways. Furthermore, using genetic markers can generate a reduction in genetic diversity by co-selecting for physically linked chromosomal sequences that could inadvertently remove interesting industrial traits. An easier method is to first generate stable heterothallic haploids for one or both parents, such as by replacing HO with drug markers, followed by interspecies crosses (Bullard et al., 2010; Swain Lenz et al., 2014; Tirosh et al., 2009). Variations of this strategy have used complementary drug markers and auxotrophic mutants in one species and spore dissection of wild-type diploids from another (Hebly et al., 2015; Piatkowska et al., 2013). However, the persistence of drug markers in the latter hybrids raises legitimate concerns about their safety that would need to be addressed prior to introducing them into the food and beverage industry.

Accordingly, there is a need in the art for new, easier, and "scarless" methods of creating genetic diversity within a yeast cell as well as new synthetic yeast strains that may be used for commercial fermentations such as in the beverage and biofuel industries.

SUMMARY

In one aspect, methods of making synthetic yeast cells are provided. The methods may be directed to mating together two diploid (or higher ploidy) yeast species or hybrids. The methods may include i) introducing a first polynucleotide comprising a first promoter operably connected to an HO polynucleotide encoding a yeast Ho protein, a first selectable marker cassette, and a first yeast origin of replication into a first yeast cell from a first yeast species or hybrid to produce a first transformed yeast cell, ii) introducing a second polynucleotide comprising a second promoter operably connected to an HO polynucleotide encoding a yeast Ho protein, a second selectable marker cassette, and a second yeast origin of replication into a second yeast cell from a second yeast species or hybrid to produce a second transformed yeast cell, and iii) co-culturing the first transformed yeast cell with the second transformed yeast cell to produce a mating mixture.

Alternatively, in another aspect, the methods of the present invention may also be directed to mating a diploid (or higher ploidy) yeast species with a haploid yeast species. Such methods may include i) introducing a first polynucleotide comprising a first promoter operably connected to an HO polynucleotide encoding a yeast Ho protein, a first selectable marker cassette, and a first yeast origin of replication into a first yeast cell from a first yeast species or hybrid to produce a first transformed yeast cell, ii) introducing a second polynucleotide comprising a second selectable marker cassette, and a second yeast origin of replication into a second yeast cell from a second haploid yeast species to produce a second transformed yeast cell, and iii) co-culturing the first transformed yeast cell with the second transformed yeast cell to produce a mating mixture.

In a further aspect, synthetic yeast cells are provided. The synthetic yeast cells may include 5, 6, 7, 8, 9, 10, 11, 12, 13, 14, 15, 16, or more sets of yeast chromosomes. As used herein, a "set of chromosomes" refers to a complete or substantially complete set of chromosomes. A set of chromosomes is 1N, a yeast is generally 2N (diploid), 4N (tetraploid), etc. The sets of chromosomes may all come from the same yeast species or may come from 2, 3, 4, 5, 6, 7, 8, or more different yeast species. The synthetic yeast cells of the present invention may also include chromosomes or chromosomal segments from 3, 4, 5, 6, 7, 8, or more yeast species.

In a further aspect, methods of using the synthetic yeast cells described herein are provided. The methods of use may include using any one of synthetic yeast cells described herein or any one of the synthetic yeast cells made by the methods disclosed herein in a fermentation process. In some embodiments, the fermentation process may be involved in beer making, wine making, cider making, biofuel production, biochemical production, or another commercially valuable process.

In a still further aspect, kits are provided. The kits may include a first polynucleotide comprising a first promoter operably connected to an HO polynucleotide encoding a yeast Ho protein, a first selectable marker cassette, and a first yeast origin of replication, and a second polynucleotide comprising a second promoter operably connected to an HO polynucleotide encoding a yeast Ho protein, a second selectable marker cassette, and a second yeast origin of replication. In some embodiments, the first selectable marker cassette and the second selectable marker cassette encode different selectable markers.

BRIEF DESCRIPTION OF THE DRAWINGS

The application file contains at least one drawing executed in color. Copies of this patent or patent application publication with color drawing(s) will be provided by the Office upon request and payment of the necessary fee.

FIG. 1A shows yHWA358 and its diploid (2n) Ethanol Red parent, FIG. 1B shows yHWA375 and its diploid *S. kudriavzevii* parent, FIG. 1C shows yHWA377 and its diploid *S. uvarum* parent, and FIG. 1D shows yHWA425 and its diploid *S. eubayanus* parent. Scer=*S. cerevisiae*, Skud=*S. kudriavzevii*, Suva=*S. uvarum*, Seub=*S. eubayanus*.

FIGS. 2A-2B shows how PCR and Restriction Fragment Long Polymorphism analyses confirm the presence of two different genomes in the synthetic allotetraploids. FIG. 2A shows the BRE5 PCR product is approximately the same size in all species shown. FIG. 2B shows digestion of the BRE5 PCR product with HaeIII produces a unique pattern for each species. Double-drug-resistant allotetraploids produce banding patterns consistent with those expected from a hybrid strain. Scer=*S. cerevisiae*, Skud=*S. kudriavzevii*, Suva=*S. uvarum*, Seub=*S. eubayanus*.

DETAILED DESCRIPTION

Figure 1A:
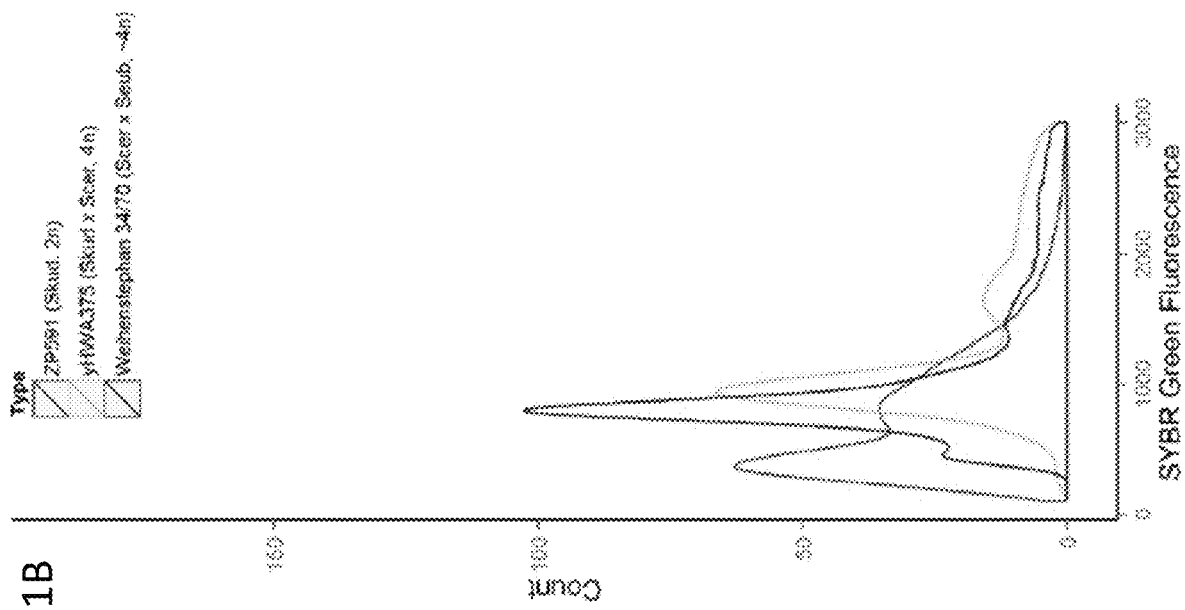
FIGS. 1A-1D shows DNA content of cells from double-drug-resistant colonies arising from HO-induced and co-cultured diploids. Diploid parents are also displayed in FIGS. 1A-1D. Flow cytometry was used to measure the DNA content of fixed, SYBR Green-stained cells harvested during exponential growth. The approximately tetraploid Weihenstephan strain is included on all graphs as a standard (Walther et al., 2014) and serves as a control to demonstrate that the new synthetic hybrids are tetraploid. Note that strains NRRL YB-210 and Wyeast #1007 German Ale did not survive the standard fixation and staining procedure intact, but genome sequencing and tetrad dissection have shown that NRRL YB-210 is approximately diploid (Wohlbach et al., 2014). These strains were stained by removing heating and protease treatments, and their comparative ploidy was determined (FIG. 6).
Figure 1B:
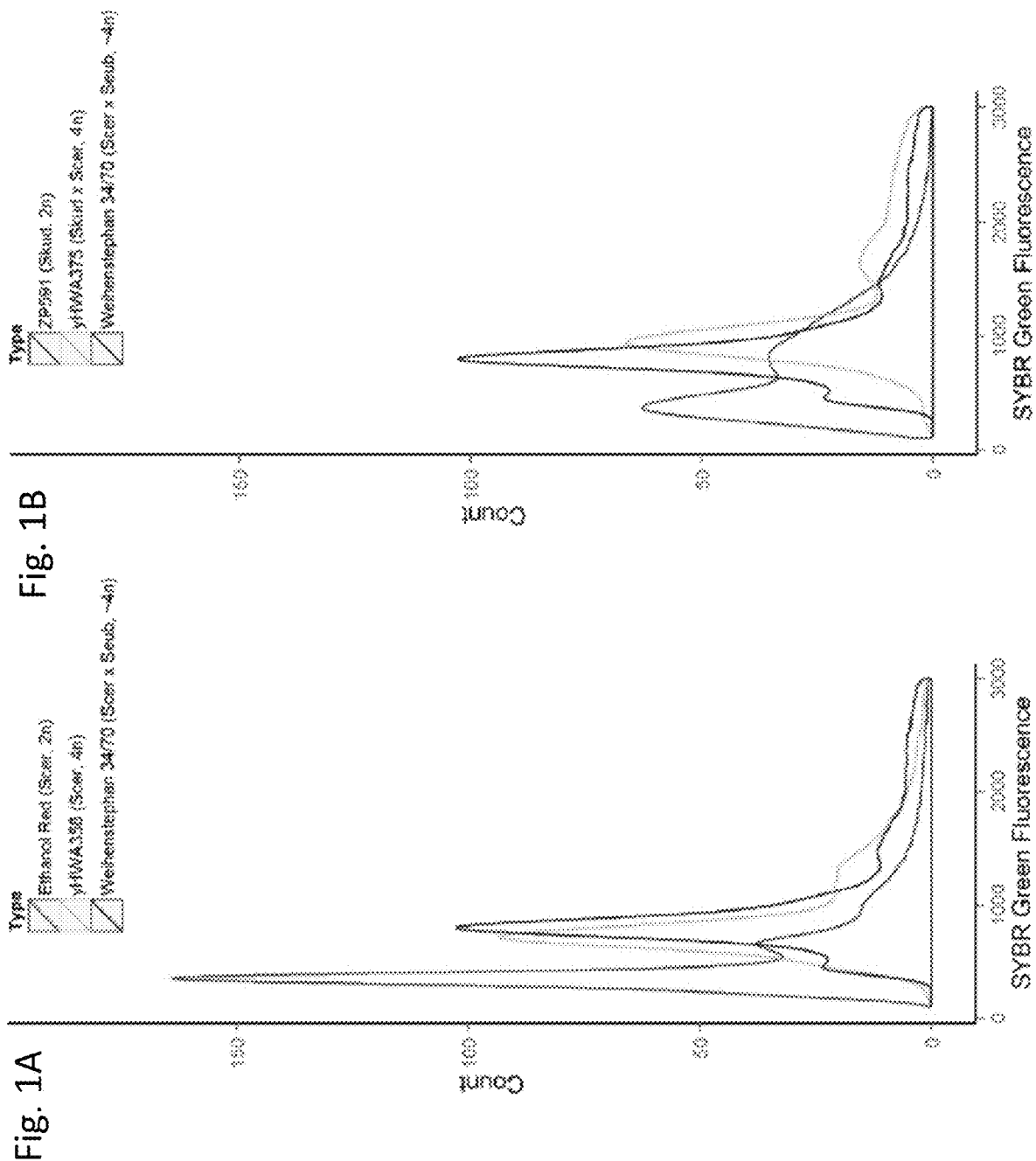
Figure 1D:
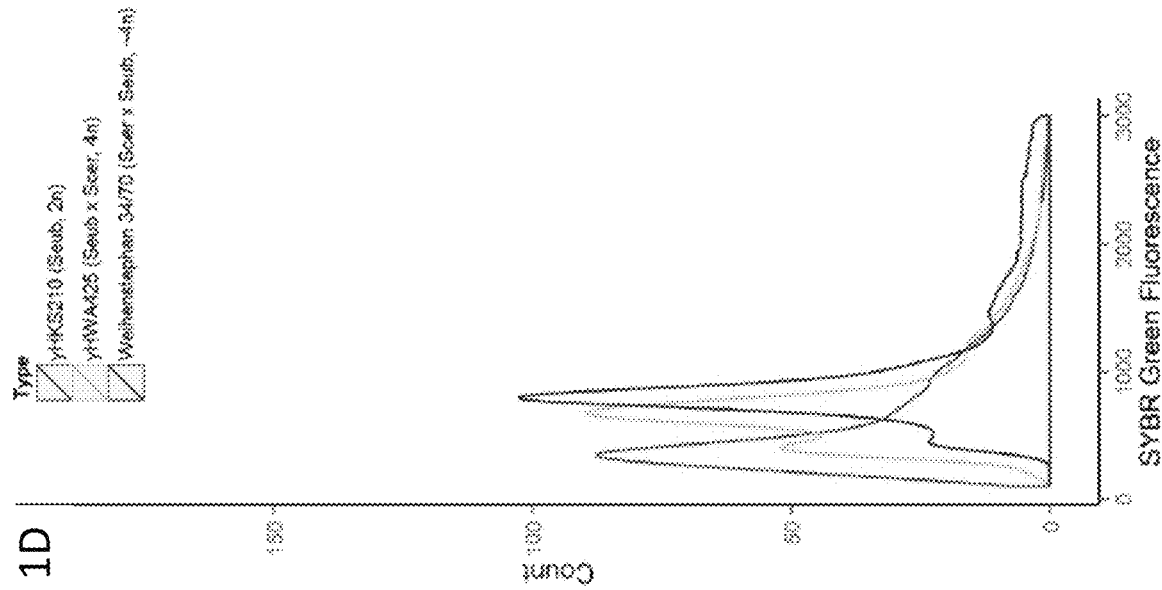
Figure 1C:
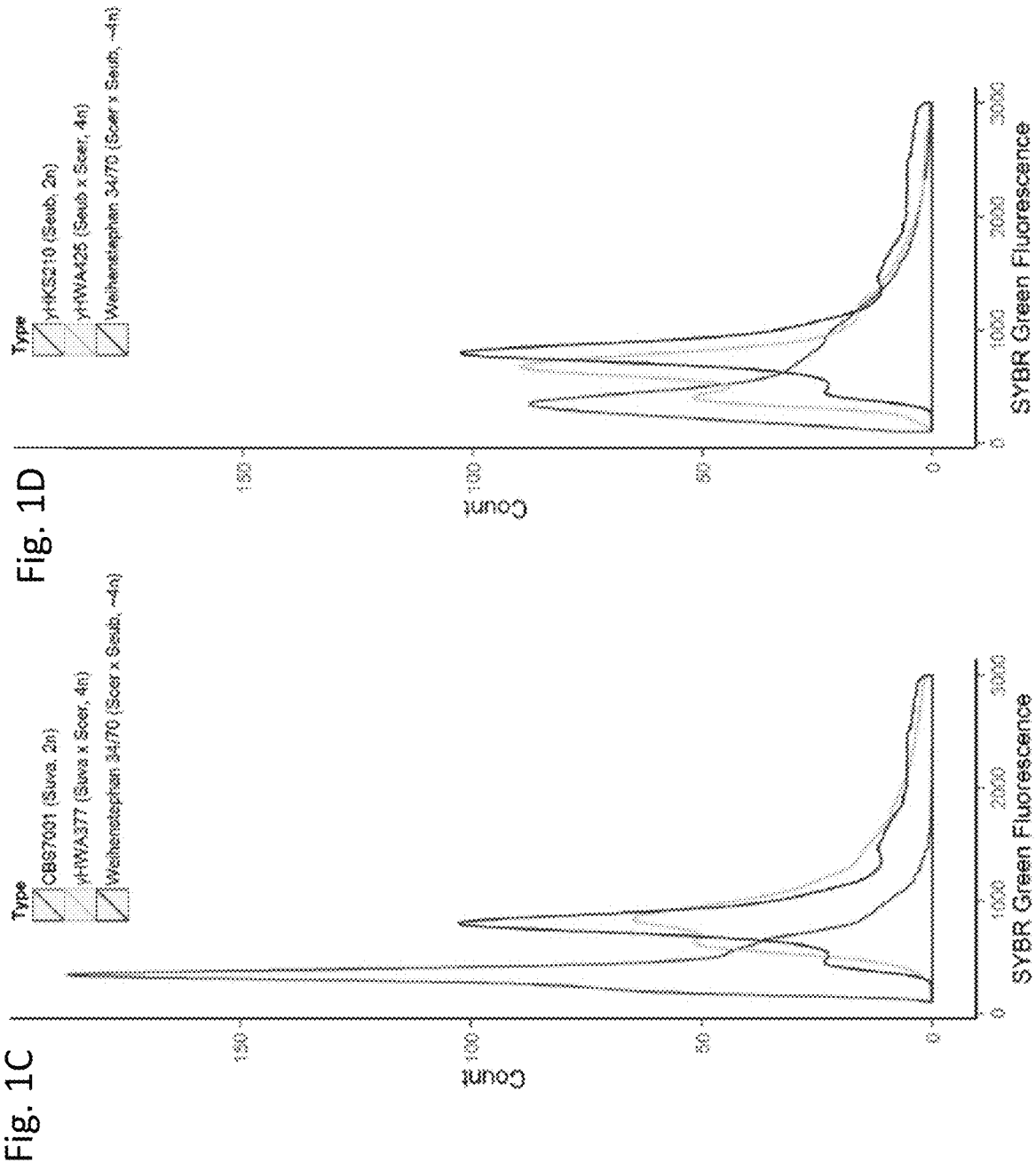

Here, the inventors describe new methods for the efficient production of designer yeast strains based on two expression plasmids. These plasmids may include complementary dominant drug-resistance cassettes, a promoter operably connected to an HO polynucleotide encoding a yeast Ho protein, and a generalized replication origin that provides functionality across *Saccharomyces* and many other yeasts.

In the non-limiting Examples, the inventors demonstrate that the methods disclosed herein efficiently produce allo-tetraploid and autotetraploid strains of *Saccharomyces*, as well as new *Saccharomyces* strains including more than 4 sets of chromosomes. The resulting strains can be rapidly screened for plasmid loss, providing an efficient route towards meeting the Generally Recognized As Safe (GRAS) standards of the United States Department of Agriculture and Food and Drug Administration. These methods and strains also provide a valuable and general research tool for basic and applied research on prototrophic hybrids and polyploids of yeasts.

The methods disclosed herein also provide an alternative method for optimization via hybridization of yeast chassis strains to be used in a variety of synthetic biology applications. For example, the methods disclosed herein can be used to create chassis strains de novo from two yeast strains with desirable traits, producing a new chassis strain with both desired characteristics without sporulation. Importantly, chassis strains made by the disclosed methods may lack drug resistance cassettes and auxotrophies, both of which are desirable qualities in beverage and biofuel strains.

Methods of making synthetic yeast cells are provided. The methods may be directed to mating together two diploid (or higher ploidy) yeast species or hybrids. The two yeast species or hybrids may be the same or different strains of a yeast species or hybrid or may be different yeast species or hybrids entirely. For example, the methods may include i) introducing a first polynucleotide comprising a first promoter operably connected to an HO polynucleotide encoding a yeast Ho protein, a first selectable marker cassette, and a first yeast origin of replication into a first yeast cell from a first yeast species or hybrid to produce a first transformed yeast cell, ii) introducing a second polynucleotide comprising a second promoter operably connected to an HO polynucleotide encoding a yeast Ho protein, a second selectable marker cassette, and a second yeast origin of replication into a second yeast cell from a second yeast species or hybrid to produce a second transformed yeast cell, and iii) co-culturing the first transformed yeast cell with the second transformed yeast cell to produce a mating mixture.

Alternatively, the methods of the present invention may also be directed to mating a diploid (or higher ploidy) yeast species with a haploid yeast species. The haploid yeast species may be the same or a different yeast strain as the diploid (or higher ploidy) yeast species or may be a different yeast species entirely. Such methods include i) introducing a first polynucleotide comprising a first promoter operably connected to an HO polynucleotide encoding a yeast Ho protein, a first selectable marker cassette, and a first yeast origin of replication into a first yeast cell from a first yeast species or hybrid to produce a first transformed yeast cell, ii) introducing a second polynucleotide comprising a second selectable marker cassette, and a second yeast origin of replication into a second yeast cell from a second haploid yeast species to produce a second transformed yeast cell, and iii) co-culturing the first transformed yeast cell with the second transformed yeast cell to produce a mating mixture.

A "yeast species," as used herein, may refer to a substantially pure yeast species or to a yeast strain that is a mixed yeast species. A substantially pure yeast species may contain greater than 95%, 96%, 97%, 98%, 99%, or 99.9% chromosomal content from a single yeast species. For example, strains of *Saccharomyces cerevisiae* that contain greater than 95%, 96%, 97%, 98%, 99%, or 99.9% *Saccharomyces cerevisiae* chromosomal content may be considered a substantially pure yeast species and would be considered to be a *Saccharomyces cerevisiae* species. A mixed yeast species may contain substantial chromosomal content from 2 or more different yeast species. For example, a particular yeast strain may have 90% chromosomal content from *Saccharomyces uvarum* and 5% chromosomal content from *Saccharomyces cerevisiae* and 5% chromosomal content from *Saccharomyces eubayanus*. In the case of mixed species, and in accordance with the present invention, the yeast species of a yeast cell from a mixed yeast species is determined by which species contributes the majority of the chromosomal content in the cell. Thus, in the preceding mixed species example, the exemplary yeast strain would be considered a *Saccharomyces uvarum* species.

The yeast species or hybrids of the present invention may be ascomycetes. Suitable yeast species or hybrids of the present invention may be from the family Saccharomycetaceae. In some embodiments, the yeast species or hybrids are from the genus *Saccharomyces*. Suitable *Saccharomyces* species may include, without limitation, *Saccharomyces cerevisiae, Saccharomyces paradoxus, Saccharomyces mikatae, Saccharomyces jurei, Saccharomyces arboricola, Saccharomyces kudriavzevii, Saccharomyces uvarum,* and *Saccharomyces eubayanus*. Suitable *Saccharomyces* hybrids may include, without limitation, *Saccharomyces* hybrids having at least one parent selected from the group consisting of *Saccharomyces cerevisiae, Saccharomyces paradoxus, Saccharomyces mikatae, Saccharomyces jurei, Saccharomyces arboricola, Saccharomyces kudriavzevii, Saccharomyces uvarum,* and *Saccharomyces eubayanus*. Suitable *Saccharomyces* species may also include any taxonomic synonyms of these species or any newly discovered species to be members of the genus *Saccharomyces*.

Figure 11B:
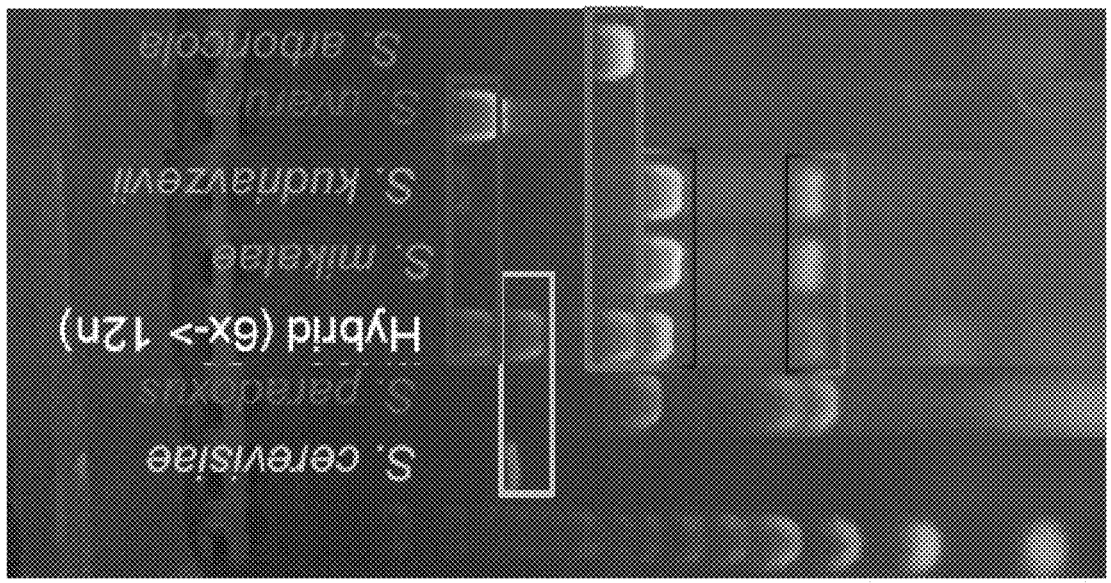
FIG. 11B is a photograph of a Restriction Fragment Length Polymorphism (RFLP) analysis used to confirm the 6 species hybrid contained genetic material derived from the parental strains of yeast. This RFLP analysis confirms the presence of at least 5 of the parental lines.
Figure 11A:
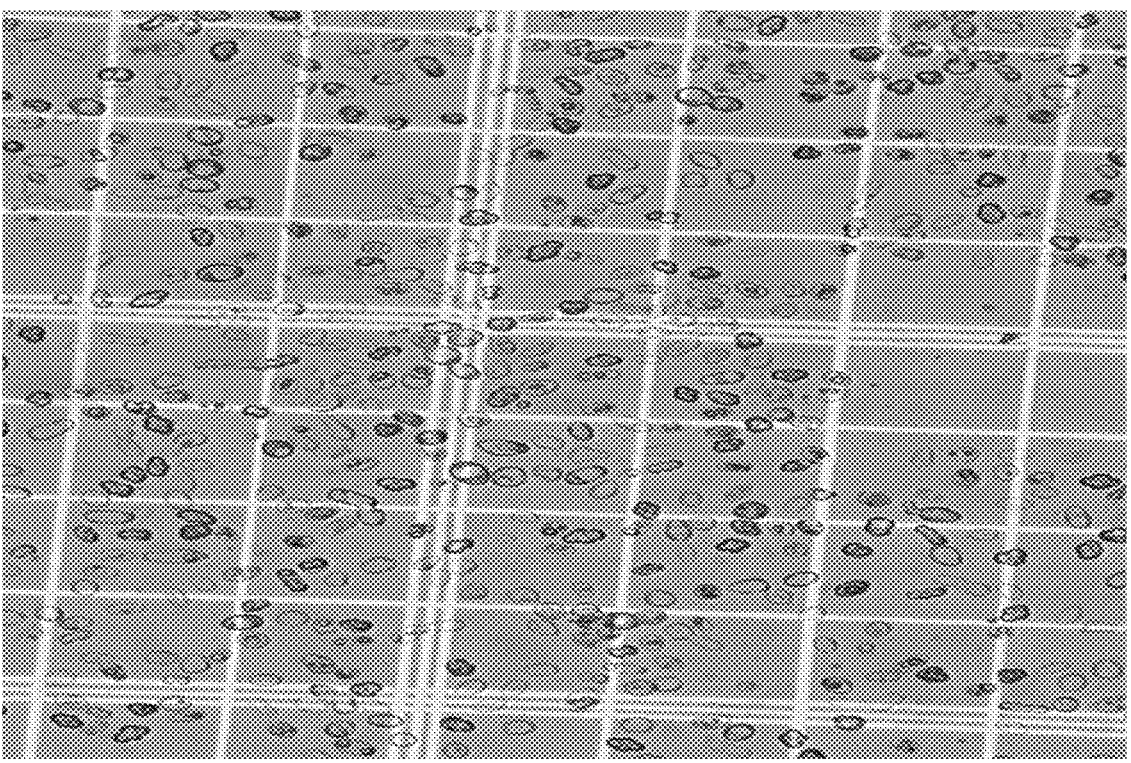
FIG. 11A is a photograph of the 6 species hybrids showing the range of yeast morphology found in the allododecaploid yeast.

The yeast species of the present methods may be haploid (1N), diploid (2N), triploid (3N), tetraploid (4N), pentaploid (5N), hexaploid (6N), heptaploid (7N), octaploid (8N), nonaploid (9N), decaploid (10N), 11N, 12N, 13N, 14N, 15N, 16N or more. The yeast hybrids of the present methods may be diploid (2N), triploid (3N), tetraploid (4N), pentaploid (5N), hexaploid (6N), heptaploid (7N), octaploid (8N), nonaploid (9N), decaploid (10N), 11N, 12N, 13N, 14N, 15N, 16N or more. In some embodiments, the first yeast species or hybrid and the second yeast species or hybrid of the present methods are diploid. In other embodiments, they may be tetraploid or higher ploidy, such as the embodiment shown to create hexaploids (FIG. 8) and 12N yeasts (FIG. 11B).

Suitable yeast species that may used in accordance with the present invention include, without limitation, species of the genera *Candida, Saccharomyces, Kazachstania, Nakaseomyces, Kluyveromyces, Lachancea, Naumovozyma, Vanderwaltozyma, Tetrapisispora, Yueomyces, Zygosaccharomyces, Torulaspora, Zygotorulaspora, Eremothecium*, and *Ashbya*. In general, we expect the present invention to work on genera whose life cycle, mating-type locus, and silent mating cassettes are sufficiently similar to *Saccharomyces*, especially with respect to Ho protein binding to and cutting the MAT locus to enable mating-type switching.

As used herein, a "yeast hybrid" refers to a yeast cell having at least one set of chromosomes from at least two different yeast species. The present methods may not only be performed using two yeast cells from either the same or different yeast species, but may also be used with yeast hybrids. A yeast hybrid may be a naturally occurring hybrid yeast strain, such as the *Saccharomyces cerevisiae×Saccharomyces eubayanus* hybrids commonly used to produce lager beers. A yeast hybrid may also be a hybrid yeast strain developed synthetically in the lab using, for example, the methods disclosed herein.

The present methods may be performed through 1, 2, 3, 4, 5, 6, 7, 8, 9, 10, or more rounds of mating. Thus, the polyploid yeast cells created using the present methods may be used as starting materials for performing subsequent rounds of the present methods. In the Examples, the inventors use 2 rounds of mating to produce a hexaploid yeast cell having 2 sets of chromosomes from three different yeast species. The inventors were further able to combine two tetraploid species to generate an 8N yeast and then use this 8N yeast to mate with another 4N yeast to generate a 12N yeast. See, e.g., Example 2 and FIGS. 8-11. The inventors also conjecture that the hexploid yeast cell could be mated with a tetraploid using the methods described herein to produce a decaploid (10N) yeast cell. It thus is particularly envisioned that the present methods may be performed reiteratively to create synthetic yeast strains that have large sets of chromosomes (ploidy) and/or chromosomes or chromosomal segments from multiple yeast species.

In some embodiments of the present methods, the first yeast species or hybrid and the second yeast species or hybrid are different yeast species or hybrids. As used herein, a "different yeast species or hybrid" refers to yeast species or hybrids that are not the same as determined in view of the "yeast species" and "yeast hybrid" definitions provided herein. For example, if the first yeast species or hybrid was a yeast strain having 90% chromosomal content from *Saccharomyces uvarum* and 5% chromosomal content from *Saccharomyces cerevisiae* and 5% chromosomal content from *Saccharomyces eubayanus* and the second yeast species was a substantially pure *Saccharomyces uvarum* strain, the first yeast species or hybrid and the second yeast species or hybrid would be considered the same—*Saccharomyces uvarum*. Examples of embodiments where the first yeast species or hybrid and the second yeast species or hybrid would be considered different might include the first yeast species or hybrid being *Saccharomyces cerevisiae* and the second yeast species or hybrid being *Saccharomyces eubayanus*.

As used herein, the terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases may refer to DNA or RNA of natural or synthetic origin (which may be single-stranded or double-stranded and may represent the sense or the antisense strand). Polynucleotides may also include modified nucleotides that permit correct read-through by a polymerase and do not alter expression of, for example, the HO polypeptide encoded by polynucleotides described herein. Preferably, the polynucleotides described herein are DNA.

The polynucleotides of the present invention may further include a promoter. The terms "promoter," "promoter region," or "promoter sequence" refer generally to transcriptional regulatory regions of a gene, which may be found at the 5' or 3' side of the HO polynucleotide, or within the coding region of the HO polynucleotide. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In some embodiments, the promoters within the polynucleotides of the present invention may be operably connected to the HO polynucleotide. As used herein, a promoter is "operably connected to" or "operably linked to" when it is placed into a functional relationship with a second polynucleotide sequence. For instance, a promoter is operably connected to an HO polynucleotide if the promoter is connected to the HO polynucleotide such that it may effect transcription of the HO polynucleotide coding sequence. In various embodiments, the HO polynucleotides may be operably linked to at least 1, at least 2, at least 3, at least 4, at least 5, or at least 10 promoters.

Promoters useful in the practice of the present invention include, but are not limited to, constitutive, inducible, temporally-regulated, and chemically regulated promoters. Preferably, the promoters are inducible. Suitable inducible promoters for expression in yeast include, without limitation, galactose inducible promoters (i.e., GAL1) and doxycycline-inducible promoters. Those of skill in the art are familiar with a wide variety of additional promoters for use in various yeast species.

In the present methods, the first and second promoters may be the same promoter or may be different promoters. In some embodiments, the first and second promoters are the same inducible promoter. In embodiments where the first and second promoters are inducible promoters, the present methods may further include inducing the first and second inducible promoters prior to co-culturing the first transformed yeast cell with the second transformed yeast cell (step (iii) of the present methods).

The polynucleotides of the present invention may include an HO polynucleotide encoding a yeast Ho protein. Yeast Ho proteins are site-specific endonucleases that produce a double-strand break in the MAT locus. The double-strand break is followed by a unidirectional gene conversion event that replaces the information at the MAT locus by information copied from either of the two homologous loci (HMR and HML). Yeast Ho proteins may be any of the Ho proteins found in any yeast species including, without limitation, those yeast species closely related to *Candida glabrata*. The *S. cerevisiae* Ho recognition site in MATa (TTTCCGCAACAGT; SEQ ID NO: 13) and MATα (TTCGCGCAACAGT; SEQ ID NO: 14) differs from *C. glabrata* by one nucleotide, but MATα Ho recognition site is recognized by ScerHo. The presence of the HO locus may extend to all genera classified in the family Saccharomycetaceae because *Kluyveromyces lactis* has a relic of HO, but it is absent from other species, such as *Kluyveromyces waltii*. Suitably, the protein sequence of an exemplary yeast Ho protein from *Saccharomyces cerevisiae* is indicated in SEQ ID NO: 11. In some embodiments, the yeast Ho protein comprises SEQ ID NO: 11 or a mutant, variant, derivative, or fragment thereof.

As used herein, a "protein," "polypeptide," or "peptide" may be used interchangeably to refer to a polymer of amino acids. A "protein" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine).

A yeast Ho protein may include "mutant" proteins, variants, and derivatives thereof. As used herein the term "wild-type" is a term of the art understood by skilled persons and means the typical form of an organism, strain, gene or characteristic as it occurs in nature as distinguished from mutant or variant forms. As used herein, a "variant, mutant," or "derivative" refers to a polypeptide molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a yeast Ho protein mutant or variant protein may have one or more insertions, deletions, or substitution of at least one amino acid residue relative to the yeast Ho "wild-type" protein. The protein sequences of a "wild-type" yeast Ho protein from *Saccharomyces cerevisiae* is presented as SEQ ID NO: 11. This sequence may be used as a reference sequence.

A yeast Ho protein may be a full-length protein or may be fragments of the full-length protein. As used herein, a "fragment" is a portion of an amino acid sequence, which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference protein, respectively. In some embodiments, a fragment may comprise at least 5, 10, 15, 20, 25, 30, 40, 50, 60, 70, 80, 90, 100, 150, 250, or 500 contiguous amino acid residues of a reference protein. Fragments may be preferentially selected from certain regions of a molecule. The term "at least a fragment" encompasses the full-length polypeptide. A fragment may include an N-terminal truncation, a C-terminal truncation, or both truncations relative to the full-length yeast Ho protein. Preferably, a fragment of a yeast Ho protein includes amino acid residues required for recognition and cleavage of the MAT locus site.

A "deletion" in a yeast Ho protein refers to a change in the amino acid sequence resulting in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide).

"Insertions" and "additions" in a yeast Ho protein refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant of a yeast Ho protein may have N-terminal insertions, C-terminal insertions, internal insertions, or any combination of N-terminal insertions, C-terminal insertions, and internal insertions.

Regarding proteins, the phrases "percent identity," "% identity," and "% sequence identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases. As described herein, variants, mutants, or fragments (e.g., a yeast Ho protein variant, mutant, or fragment thereof) may have 99%, 98%, 97%, 96%, 95%, 94%, 93%, 92%, 91%, 90%, 80%, 70%, 60%, or 50% amino acid sequence identity relative to a reference molecule (e.g., relative to a full-length yeast Ho protein (SEQ ID NO: 11)).

Protein sequence identity may be measured over the length of an entire defined protein sequence, for example, as defined by a particular SEQ ID number, or may be measured over a shorter length, for example, over the length of a fragment taken from a larger, defined protein sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

The amino acid sequences of the yeast Ho protein variants, mutants, or derivatives as contemplated herein may include conservative amino acid substitutions relative to a reference amino acid sequence. For example, a variant, mutant, or derivative polypeptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The HO polynucleotides encoding the yeast Ho proteins, fragments, variants, mutants, or derivatives thereof may be any polynucleotide encoding the appropriate yeast Ho protein amino acid sequence. Those of skill in the art also understand the degeneracy of the genetic code and that a variety of polynucleotides can encode the same polypeptide. In some embodiments, the polynucleotides may be codon-optimized for expression in a particular yeast cell. While particular nucleotide sequences which are found in *Saccharomyces cerevisiae* (i.e., SEQ ID NO: 12) are disclosed herein any nucleotide sequences may be used which encode a desired form of the yeast Ho proteins described herein. Thus non-naturally occurring sequences may be used. These may be desirable, for example, to enhance expression in a particular yeast species. Computer programs for generating degenerate coding sequences are available and can be used for this purpose as well as other means.

The polynucleotides of the present invention may also include a selectable marker cassette. In the Examples, the selectable marker cassettes used in the exemplary HyPr pHCT2 and pHMK34 plasmids conferred resistance to nourseothricin (natMX4) and hygromycin (hphMX), respectively. Two additional plasmids were generated for use in the methods provided herein including pHRW32 (SEQ ID NO: 16), which includes zeocin resistance and pHRW40 (SEQ ID NO: 15), which includes G418 resistance. Other selectable markers conferring resistance to other antibiotics such as, kanMX, amdS, TK, Sh ble or ble, which confer resistance to G418, fluoroacetamide, antifolates, Zeocin or phleomycin, respectively could also be used. Those of skill in the art will appreciate that additional combinations of selectable markers can be used as well. Other forms of selectable markers may be used such as markers that provide a growth advantage or colorimetric selection other than antibiotic resistance. The selectable marker cassettes include a polynucleotide encoding the selectable marker operably connected to a promoter capable of inducing transcription of the selectable marker.

Suitably, the first selectable marker cassette and the second selectable marker cassette encode different selectable markers. By encoding different complementary selectable marker cassettes, the disclosed methods readily select for mating events between the first yeast cell and the second yeast cell.

The polynucleotides of the present invention may also include a yeast origin of replication to allow replication of the polynucleotides in a particular yeast species. Suitably, the first yeast origin of replication and the second yeast origin of replication are functional across many yeast species including, without limitation, all *Saccharomyces* species. In the Examples, the yeast origin of replication used in the exemplary HyPr pHCT2 and pHMK34 plasmids included KARS101 from *Kluyveromyces lactis* and *S. cerevisiae* CEN and ARS sequences to improve stability in multiple yeast species.

As used herein, "introducing" describes a process by which exogenous polynucleotides (e.g., DNA or RNA) are introduced into a recipient yeast cell. Methods of introducing polynucleotides into a yeast cell are known in the art and may include, without limitation, transformation methods such as electroporation and lithium acetate/single-stranded carrier DNA/PEG methods. Transformation may occur under natural or artificial conditions according to various methods well known in the art, and may rely on any known method for the insertion of foreign nucleic acid sequences into a yeast cell. The method for transformation may be selected based on the type of yeast cell being transformed and may include, but is not limited to, electroporation, heat shock, chemical transformation methods such as lithium acetate/single-stranded carrier DNA/PEG methods.

As used herein, a "transformed" yeast cell refers to a yeast cell carrying an exogenous polynucleotide that was introduced into the yeast cell using the transformation methods described herein.

As used herein, "co-culturing" refers to growing at least two yeast cells in an appropriate media. Common yeast growth media are well known in the art and include, without limitation, YPD media. In some embodiments, the present methods may include co-culturing the first transformed yeast cell with the second transformed yeast cell to produce a mating mixture. A "mating mixture" refers to a mixture of at least two yeast cells, which will likely have at least one yeast cell having a MATa mating type and at least one yeast cell having a MATα mating type. Suitably, in some embodiments, the mating mixture is introduced onto plates to facilitate mating of the yeast cells.

In some embodiments, the present methods may further include selecting at least a portion of the mating mixture for the first selectable marker and the second selectable marker to select for a synthetic yeast cell. A "synthetic yeast cell" refers to a yeast that may be made using the present methods. The "selecting at least a portion of the mating mixture" may be performed by simply adding the appropriate agents (i.e., antibiotics) to the growth media to select for cells harboring the first selectable marker and/or the second selectable marker.

The present methods may further include culturing the synthetic yeast cell in non-selective media to produce a synthetic yeast cell lacking the first polynucleotide and/or the second polynucleotide. Such embodiments of the present methods may provide an efficient route towards meeting the Generally Recognized As Safe (GRAS) standards of the United States Department of Agriculture and Food and Drug Administration.

In some embodiments, the present methods may further include selecting the synthetic yeast cell under conditions to optimize the synthetic yeast cell for a fermentation process. As used herein, a "fermentation process" may involve any fermentation process involved in beer making, wine making, cider, sake and traditional alcoholic beverages (mezcal, chicha, mudai, among others), biofuel production, or other commercially valuable process. Extensive prior work has shown that yeast polyploid strains, for example, are relatively unstable, rapidly losing chromosomes to form aneuploid strains. This loss occurs rapidly with genome content reduction to near-diploid levels in 200 to 800 generations. The inventors expect that synthetic yeast cells made via the methods disclosed herein to behave in a similar manner. This could, in fact, be a desirable trait for many applications, as placing an unstable polyploid strain in a selective condition will influence which components of the genome are retained or lost from which parent, allowing for more rapid adaptation to that condition. The inventors expect that synthetic yeast cells made by the methods disclosed herein will also evolve aneuploidy given enough time, but again, many of these aneuploidies may be advantageous in the conditions where they are evolved.

Synthetic yeast cells are provided. The synthetic yeast cells may include 5, 6, 7, 8, 9, 10, 11, 12, 13, 14, 15, 16, or more sets of yeast chromosomes. As used herein, a "set of chromosomes" refers to a complete or substantially complete set of chromosomes. The sets of chromosomes may all come from the same yeast species or may come from 2, 3, 4, 5, 6, 7, 8, or more different yeast species.

The synthetic yeast cells of the present invention may also include chromosomes or chromosomal segments from 3, 4, 5, 6, 7, 8, or more yeast species.

The synthetic yeast cells may be an ascomycete including, without limitation, a yeast species from the family Saccharomycetaceae or a *Saccharomyces*. In some embodiments, the chromosomes or chromosomal segments in the synthetic yeast cells are from an ascomycete, including, without limitation, *Saccharomyces*. Suitable *Saccharomyces* species include, without limitation, *Saccharomyces cerevisiae, Saccharomyces paradoxus, Saccharomyces mikatae, Saccharomyces jurei, Saccharomyces arboricola, Saccharomyces kudriavzevii, Saccharomyces uvarum*, and *Saccharomyces eubayanus*.

The synthetic yeast cells may be selected from the strains consisting of yHWA358, yHWA375, yHWA377, yHWA425, yHWA439, yHWA451, yHWA452, yHWA455, and yHWA456, yHWA457, yHWA458, yHWA459, yHWA460, any of the strains identified in Table 1 or any other yeast strain developed using the methods provided herein.

Methods of using the synthetic yeast cells described herein are provided. The methods of use may include using any one of synthetic yeast cells described herein or any one of the synthetic yeast cells made by the methods disclosed herein in a fermentation process. In some embodiments, the fermentation process may be involved in beer making, wine making, biofuel production, or another commercially valuable process.

Kits are provided. The kits may include a first polynucleotide comprising a first promoter operably connected to an HO polynucleotide encoding a yeast Ho protein, a first selectable marker cassette, and a first yeast origin of replication, and a second polynucleotide comprising a second promoter operably connected to an HO polynucleotide encoding a yeast Ho protein, a second selectable marker cassette, and a second yeast origin of replication. In some embodiments, the first selectable marker cassette and the second selectable marker cassette encode different selectable markers.

Optionally, the first promoter and/or the second promoter may be an inducible promoter. The first yeast origin of replication and the second yeast origin of replication may also be functional across all *Saccharomyces* species or other yeast species.

The kits may further include nourseothricin, hygromycin, G418, fluoroacetamide, antifolates, Zeocin, phleomycin, doxycycline, at least two different *Saccharomyces* species and/or instructions for performing any one of the methods of disclosed herein.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Efficient Engineering of Marker-Free Synthetic Allotetraploids of *Saccharomyces*

*Saccharomyces* interspecies hybrids are critical biocatalysts in the fermented beverage industry, including in the production of lager beers, Belgian ales, ciders, and cold-fermented wines. Current methods for making synthetic interspecies hybrids are cumbersome and/or require genome modifications. We have developed a simple, robust, and efficient method for generating allotetraploid strains of prototrophic *Saccharomyces* without sporulation or nuclear genome manipulation. *S. cerevisiae*×*S. eubayanus*, *S. cerevisiae*×*S. kudriavzevii*, and *S. cerevisiae*×*S. uvarum* designer hybrid strains were created as synthetic lager, Belgian, and cider strains, respectively. The ploidy and hybrid nature of the strains were confirmed using flow cytometry and PCR-RFLP analysis, respectively. This method provides an efficient means for producing novel synthetic hybrids for beverage and biofuel production, as well as for constructing tetraploids to be used for basic research in evolutionary genetics and genome stability.

Many eukaryotic organisms are able to reproduce sexually, wherein meiosis serves to both increase genetic diversity and to repair genetic material (Kohl and Sekelsky, 2013). As with other eukaryotes, fungal meiosis generally initiates in diploid cells (John, 1990). Regulation of this process involves specialized genetic loci called the mating-type (MAT) loci (Kronstad and Staben, 1997). While basidiomycetes may possess thousands of different mating types, ascomycetes possess only two (Casselton and Olesnicky, 1998). Ascomycete MAT loci contain between one and three genes. The mating-type genes are not recently diverged homologs, and are thus described as idiomorphs, rather than alleles. These mating-type genes encode transcription factors that regulate the expression of meiosis-specific genes (Van Heeckeren et al., 1998), as well as other genes that function in self recognition (Glass et al., 2000), pheromone production (Bardwell, 2004), and non-homologous end joining (Frank-Vaillant and Marcand, 2001). Heterothallic ascomycetes, such as *Neurospora crassa*, require two individuals of different mating types to contribute haploid nuclei towards a transient diploid meiotic precursor cell (Glass et al., 1990; Staben and Yanofsky, 1990).

The genus *Saccharomyces* is composed of unicellular diploid ascomycete fungi (Hittinger, 2013). The *S. cerevisiae* MAT idiomorphs are termed MATa and MATα, and both possess two genes (Haber, 2012). Unlike many other ascomycetes where vegetative haploid nuclei give rise to a transient diploid cell, *Saccharomyces* haploid spores of a single mating type rapidly give rise to stable diploid cells possessing both mating-type loci by way of mating-type switching (Haber, 2012). When a newly germinated haploid cell divides, the mother cell expresses HO, producing an endonuclease that specifically targets the mating-type locus. The resulting DNA double-strand break (DSB) is repaired using information from silenced copies of either mating-type idiomorph found on the same chromosome as the MAT locus (designated HML and HMR). Repairing the DSB lesion occurs by replacing the existing MAT idiomorph with the silenced copy of the other MAT idiomorph, resulting in the mother cell switching to the opposite mating type. As the daughter cell retains the initial idiomorph, mating-type switching ensures two haploid cells of opposite mating-types are adjacent to one another for schmooing and the formation of a diploid zygote. Deletion of HO prevents mating types from being switched, forming stable haploid strains, such as those typically used in laboratory research (Walker et al., 2003). Indeed, the plasticity of *Saccharomyces* ploidy is a major component of the awesome power of yeast genetics. Induced HO expression from plasmids in hoΔ strains triggers mating-type switching, resulting in diploidization of otherwise stable haploid strains (Herskowitz and Jensen, 1991; Jensen and Herskowitz, 1984). This diploid yeast cell can then be sporulated by standard methods, dissected, and the progeny screened for their mating type. The resulting haploids are isogenic to the original haploid strain save for their mating types, which can then be used in downstream genetic crosses. In addition to long-standing use to control mating type and ploidy in lab strains of *S. cerevisiae*, induction of HO expression has also been used to enable crosses between a fertile strain of *S. uvarum* and a sterile strain whose genome was predominantly *S. uvarum*, allowing a trait to be mapped using standard meiotic techniques (Schwartz et al., 2012).

All seven known species of *Saccharomyces* yeasts possess the same mating-type locus organization and a predominantly diploid or diplontic lifestyle. Only limited prezygotic speciation barriers exist between *Saccharomyces* species (Maclean and Greig, 2008), making hybridization a trivial process with marked heterothallic haploids (Bullard et al., 2010; Hebly et al., 2015; Hittinger, 2013; Piotrowski et al., 2012; Scannell et al., 2011; Swain Lenz et al., 2014; Tirosh et al., 2009). Hybridization events also happen in the wild, though at a very low frequency (Mortimer, 2000). These hybrids arise when a cell of one species mates with a cell from another. Interspecies hybridization can either occur between two haploids, as is typically done in the laboratory, or through "rare mating" when one or both parents are diploid. Rare mating diploids can gain mating competency by simply inactivating one idiomorph to become hemizygous or undergoing spontaneous gene conversion at the MAT locus and becoming MATa/MATa or MATα/MATα diploids (Gunge and Nakatomi, 1972).

Interspecies hybrids spontaneously arising in this manner have found purchase in the conditions created by humans during industrial fermentations, such as brewing; indeed, hybrids produce many commercially important fermented beverages. For example, *Saccharomyces cerevisiae*×*Saccharomyces eubayanus* hybrids are used to produce lager beer, the most common fermented beverage on the planet (Corran, 1975; Libkind et al., 2011). Two major lineages are used in lager production (Dunn and Sherlock, 2008; Nakao et al., 2009; Walther et al., 2014), and recent evidence indicates that these two lineages arose from independent hybridization events, suggesting that genetic diversity from the parental populations may be one contributor to the phenotypic differences seen in modern industrial strains (Baker et al., 2015). Many other fermented beverages also make use of *Saccharomyces* hybrids: *S. cerevisiae*×*Saccharomyces uvarum* hybrids are used in production of some ciders and cold-fermented wines (Le Jeune et al., 2007; Masneuf et al., 1998; Pérez-Través et al., 2014b), while many Belgian ale and some European wine yeasts are *S. cerevisiae*×*Saccharomyces* kudriavzevii hybrids (Peris et al., 2012a, 2012b).

The discovery of the wild genetic stocks related to the constituent species of industrial interspecies hybrids (Almeida et al., 2014; Libkind et al., 2011; Sampaio and Gonçalves, 2008), as well as the discovery of several more divergent lineages that do not seem to have contributed to the production of fermented beverages (Bing et al., 2014; Hittinger et al., 2010; Leducq et al., 2014; Liti et al., 2009, 2005; Peris et al., 2014; Wang et al., 2012), has raised interest in synthetic interspecies hybrids that may possess novel properties and allow for strain improvement. New hybrid brewing strains have been generated by a laborious process of isolating auxotrophic mutants, which arise spontaneously at low frequency, followed by crossing to obtain hybrids (Krogerus et al., 2015; Pérez-Través et al., 2012). Although this method lacks markers, which would likely streamline approval for food and beverage applications, the strains contain mutations in important biosynthetic pathways. An easier method is to first generate stable heterothallic haploids for one or both parents, for example by replacing HO with drug markers, followed by interspecies crosses (Bullard et al., 2010; Swain Lenz et al., 2014; Tirosh et al., 2009). Variations of this strategy have used complementary drug markers and auxotrophic mutants in one species and spore dissection of wild-type diploids from another (Hebly et al., 2015; Piatkowska et al., 2013). However, the persistence of drug markers in the latter hybrids raises legitimate concerns about their safety that would need to be addressed prior to introducing them into the food and beverage industry.

Here we describe a generalized method for the efficient production of designer hybrid strains of *Saccharomyces* based on a series of inducible expression plasmids named HyPr (for Hybrid Production). These plasmids contain complementary dominant drug-resistance markers, a doxycycline-inducible HO cassette, and a generalized replication origin that provides functionality across *Saccharomyces* and many other yeasts. HyPr efficiently produces allotetraploid and autotetraploid strains of *Saccharomyces*, as well as allohexaploid strains and strains of higher ploidies. The resulting strains can be rapidly screened for plasmid loss, providing an efficient route towards meeting the standards that the United States Department of Agriculture and Food and Drug Administration have previously applied to a wine strain of *S. cerevisiae*, which is Generally Recognized As Safe (GRAS) (Husnik et al., 2006). These techniques also provide a valuable and general research tool for basic and applied research on prototrophic hybrids and polyploids of *Saccharomyces*.

Materials and Methods
Strains, Culture Conditions, and Media

Strains used in this work are found in Table 1. *S. cerevisiae* strains were cultured at 30° C., except when they were being co-cultured with another species. All other *Saccharomyces* species were cultured at room temperature (22-23° C.). Routine cultures were maintained in YPD (1% yeast extract, 2% peptone, 2% glucose). Hygromycin was added to YPD at a concentration of 200 mg/L to make YPD+hyg. Nourseothricin was added to YPD at a concentration of 100 mg/L to make YPD+nat. All liquid media was solidified when needed by the addition of 1.8% agar.

TABLE 1

Strains used in this work

| Identifier | Species | Genotype | Source |
|---|---|---|---|
| RM11-1a | Saccharomyces cerevisiae | MATa leu2-Δ ura3-Δ hoΔ::KanMX | Brem et al. (2002) |
| Ethanol Red | Saccharomyces cerevisiae | MATa/MATα | Fermentis |
| NRRL YB-210 | Saccharomyces cerevisiae | MATa/MATα | Mortimer and Johnston (1986) |
| Wyeast #1007, German Ale | Saccharomyces cerevisiae | MATa/MATα | Wyeast |
| ZP 591 | Saccharomyces kudriavzevii | MATa/MATα | Sampaio and Gonçalves (2008) |
| CBS 7001 | Saccharomyces uvarum | MATa/MATα | Scannell et al. (2011) |
| yHKS210 | Saccharomyces eubayanus | MATa/MATα | Peris et al. (2014) |
| White Labs WLP830, German Lager, Weihenstephan 34/70 | Saccharomyces cerevisiae × Saccharomyces eubayanus | MATa/MATa/MATα/MATα | White Labs |
| yHWA338 | Saccharomyces cerevisiae | RM11-1a [pHCT2] | This work |
| yHWA340 | Saccharomyces cerevisiae | Ethanol Red [pHCT2] | This work |
| yHWA341 | Saccharomyces cerevisiae | NRRL YB-210 [pHMK34] | This work |
| yHWA348 | Saccharomyces uvarum | CBS 7001 [pHMK34] | This work |
| yHWA350 | Saccharomyces cerevisiae | Wyeast #1007 [pHCT2] | This work |
| yHWA352 | Saccharomyces eubayanus | yHKS210 [pHMK34] | This work |
| yHWA354 | Saccharomyces kudriavzevii | ZP 591 [pHMK34] | This work |
| yHWA358 | Saccharomyces cerevisiae | Ethanol Red [pHCT2] × NRRL YB-210 [pHMK34] | This work |
| yHWA375 | Saccharomyces cerevisiae × Saccharomyces kudriavzevii | Wyeast #1007 [pHCT2] × ZP 591 [pHMK34] | This work |
| yHWA377 | Saccharomyces cerevisiae × Saccharomyces uvarum | Wyeast #1007 [pHCT2] × CBS 7001 [pHMK34] | This work |
| yHWA425 | Saccharomyces cerevisiae × Saccharomyces eubayanus | Wyeast #1007 [pHCT2] × yHKS210 [pHMK34] | This work |
| yHWA439 | Saccharomyces cerevisiae × Saccharomyces eubayanus | Wyeast #1007 × yHKS210 | This work |

| Identifier | Species | Genotype | Source/Comments |
|---|---|---|---|
| yHWA 451 | S. cerevisiae/ S. eubayanus/ S. kudravzevii | MATa/MATa/MATa/ MATα/MATα/MATα [pHCT2][pHMK34] | putative hexaploid with PCR-RFLP confirmed Scer, Seub, and Skud genomes present; grown on SCGly to confirm respiration capability |
| yHWA 452 | S. cerevisiae/ S. eubayanus/ S. kudravzevii | MATa/MATa/MATa/ MATα/MATα/MATα [pHCT2][pHMK34] | putative hexaploid with PCR-RFLP confirmed Scer, Seub, and Skud genomes present; grown on SCGly to confirm respiration capability |

TABLE 1-continued

Strains used in this work

| | | | |
|---|---|---|---|
| yHWA 453 | S. mikatae | MATa/MATα [pHCT2] | Contains pHCT2, transformed by and obtained from Ryan Moriarty |
| yHWA 454 | S. arboricola | MATa/MATα [pHMK34] | Contains pHMK34, transformed by and obtained from Ryan Moriarty |
| yHWA 455 | S. cerevisiae/ S. eubayanus/ S. kudriavzevii | MATa/MATa/MATa/ MATα/MATα/MATα | putative hexaploid hybrid between yHWA450 and yHWA354, presence of Scer Skud and Seub genomes confirmed with PCR-RFLP; cured of both plasmids |
| yHWA 456 | S. cerevisiae/ S. eubayanus/ S. kudriavzevii | MATa/MATa/MATa/ MATα/MATα/MATα | putative hexaploid hybrid between yHWA450 and yHWA354, presence of Scer Skud and Seub genomes confirmed with PCR-RFLP; cured of both plasmids |
| yHWA 457 | S. cerevisiae/ S. eubayanus/ S. kudriavzevii | MATa/MATa/MATa/ MATα/MATα/MATα [pHCT2] | putative hexaploid hybrid between yHWA450 and yHWA354, presence of Scer Skud and Seub genomes confirmed with PCR-RFLP |
| yHWA 458 | S. cerevisiae/ S. eubayanus/ S. kudriavzevii | MATa/MATa/MATa/ MATα/MATα/MATα [pHCT2] | putative hexaploid hybrid between yHWA450 and yHWA354, presence of Scer Skud and Seub genomes confirmed with PCR-RFLP |
| yHWA 459 | S. cerevisiae/ S. eubayanus/ S. kudriavzevii | MATa/MATa/MATa/ MATα/MATα/MATα [pHMK34] | putative hexaploid hybrid between yHWA450 and yHWA354, presence of Scer Skud and Seub genomes confirmed with PCR-RFLP |
| yHWA 460 | S. cerevisiae/ S. eubayanus/ S. kudriavzevii | MATa/MATa/MATa/ MATα/MATα/MATα [pHMK34] | putative hexaploid hybrid between yHWA450 and yHWA354, presence of Scer Skud and Seub genomes confirmed with PCR-RFLP |
| yHRVM 349 | S. cerevisiae | | yHAB335; Nat resistant |
| yHRVM 346 | S. paradoxus | | CBS432; Hyg resistant |
| yHRVM 359 | S. arboricola | | CBS 10644; Nat resistant |
| yHRVM 356 | S. uvarum | | yHCT77; Hyg resistant |
| yHDPN 405 | S. mikatae | | IFO1815; Hyg resistant |
| yHRVM 371 | S. kudriavzevii | | yHAB407; Nat resistant |
| yHRVM 456 | S. cerevisiae × S. paradoxus | | yHAB335 × CBS432; Nat + Hyg resistant; confirmed by RFLP |
| yHRVM 461 | S. uvarum × S. arboricola | | yHCT77 × CBS 10644; Nat + Hyg resistant; confirmed by RFLP |
| yHRVM 501 | S. mikatae × S. kudriavzevii | | IFO1815 × yHAB407; Nat + Hyg resistant; confirmed by RFLP |
| yHRVM 495 | S. cerevisiae × S. paradoxus × S. uvarum × S. arboricola | | yHRVM491 (=yHRVM456 without [HYG]) × yHRVM492 (=yHRVM461 without [NAT]); confirmed by RFLP |
| yHRVM 548 | S. cerevisiae × S. paradoxus × S. uvarum × S. arboricola × S. mikatae × S. kudriavzevii | | yHRVM534 (=yHRVM501 without [HYG]) × yHRVM540 (=yHRVM495 without [NAT]); confirmed by RFLP |

Saccharomyces Transformation

Transformation of yeast strains was done using the lithium acetate/PEG-4000/carrier DNA method as previously described (Gietz and Woods, 2002) with the following modifications: S. cerevisiae was heat shocked at 42° C. for 30 minutes, S. uvarum and S. eubayanus were heat shocked at 37° C. for 30 minutes, and S. kudriavzevii was heat shocked at 34° C. for 30 minutes. Cells were suspended in YPD, followed by incubation at optimal temperature for three hours before being plated to selective media.

PCR

Primers used in this work are found in Table 2. Plasmid components were amplified using the Phusion PCR Kit (New England Biolabs, Ipswich, MA) as directed by the product insert. Mating-type screening and PCR-RFLP analysis used the Standard Taq Polymerase (New England Biolabs, Ipswich, MA) system as directed by the product insert for amplification.

TABLE 2

Oligonucleotides used in this work.

| Name | Sequence | Use |
| --- | --- | --- |
| MATa F | CTCCACTTCAAGTAAGAGTTTGGGT (SEQ ID NO: 1) | mating type screening |
| MATalpha F | TTACTCACAGTTTGGCTCCGGTGT (SEQ ID NO: 2) | mating type screening |
| Common MAT R | GAACCGCATGGGCAGTTTACCTTT (SEQ ID NO: 3) | mating type screening |
| oHDP022 | TGATTATAGCCACGGGTGARATGTTYT (SEQ ID NO: 4) | amplifies fragment of BRE5 for PCR-RFLP analysis |
| oHDP023 | TGATTATAGCCACKGGTGARATGTTTT (SEQ ID NO: 5) | amplifies fragment of BRE5 for PCR-RFLP analysis |
| oHDP024 | TTCAKTCATCAAYTTTGAGGCCCATGT (SEQ ID NO: 6) | amplifies fragment of BRE5 for PCR-RFLP analysis |
| oHWA230 | AAACGCTCCCCTCACAGACG (SEQ ID NO: 7) | amplifies MX-driven drug markers for marker exchange |
| oHWA231 | CTGGGCAGATGATGTCGAGG (SEQ ID NO: 8) | amplifies MX-driven drug markers for marker exchange |
| CTH993 | caaatacacacactaaattaccggatcaattcgg gggaAAAATGCTTTCTGAAAACACGA (SEQ ID NO: 9) | amplifies S. cerevisiae HO from YCp50-HO-D6, clones into pBM5155 over NotI site by gap repair |
| CTH994 | cctccacctccaccgttaattaacccggggatcc gGCAGATGCGCGCACCT (SEQ ID NO: 10) | amplifies S. cerevisiae HO from YCp50-HO-D6, clones into pBM5155 over NotI site by gap repair |

Figure 4A:
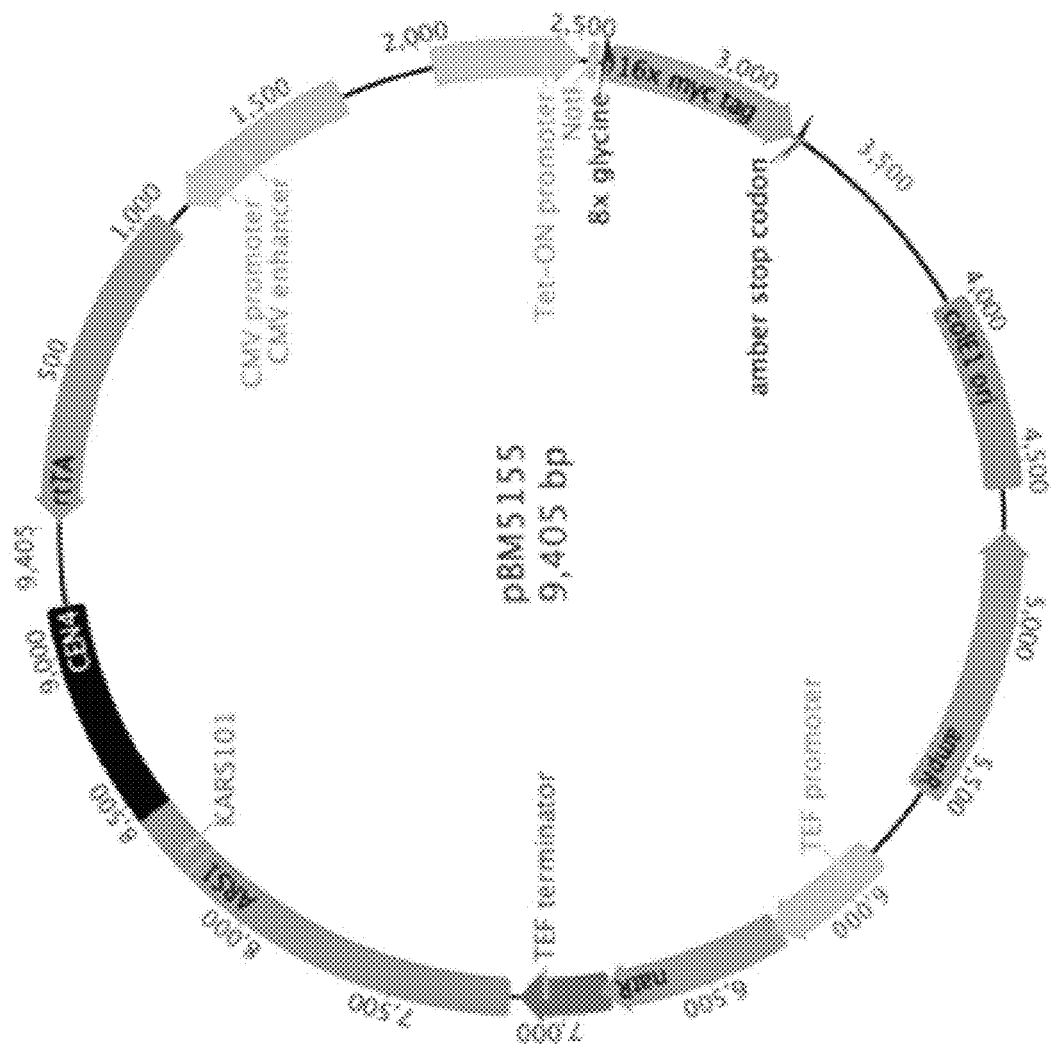
FIGS. 4A-4C shows vector maps of pBM5155 (FIG. 4A), pHCT2 (FIG. 4B), and pHMK34 (FIG. 4C). Sequences for these vectors have been deposited in GenBank under the accession numbers KT725394, KT725395, and KT781077, respectively. Vector maps were drawn in Geneious 4.7.4.
Figure 4B:
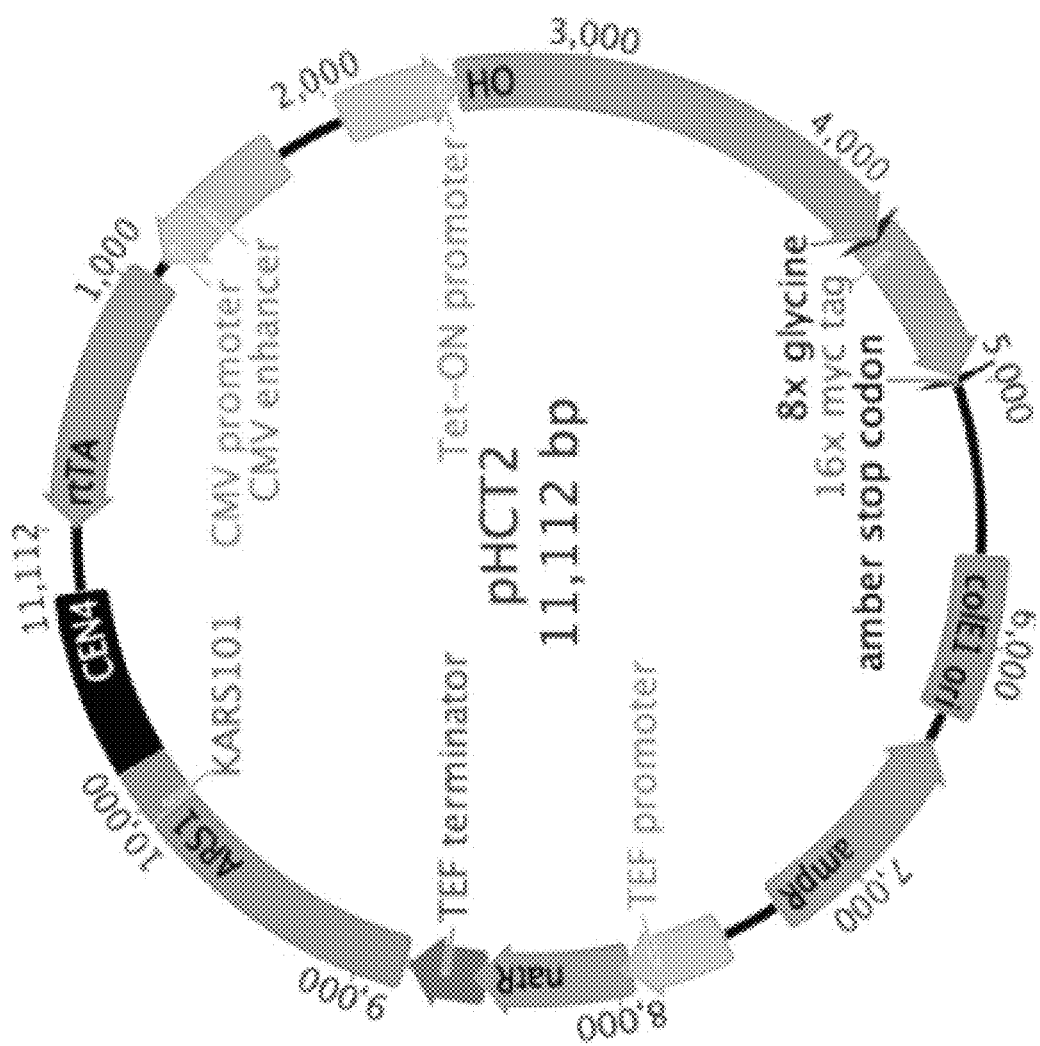
Figure 4C:
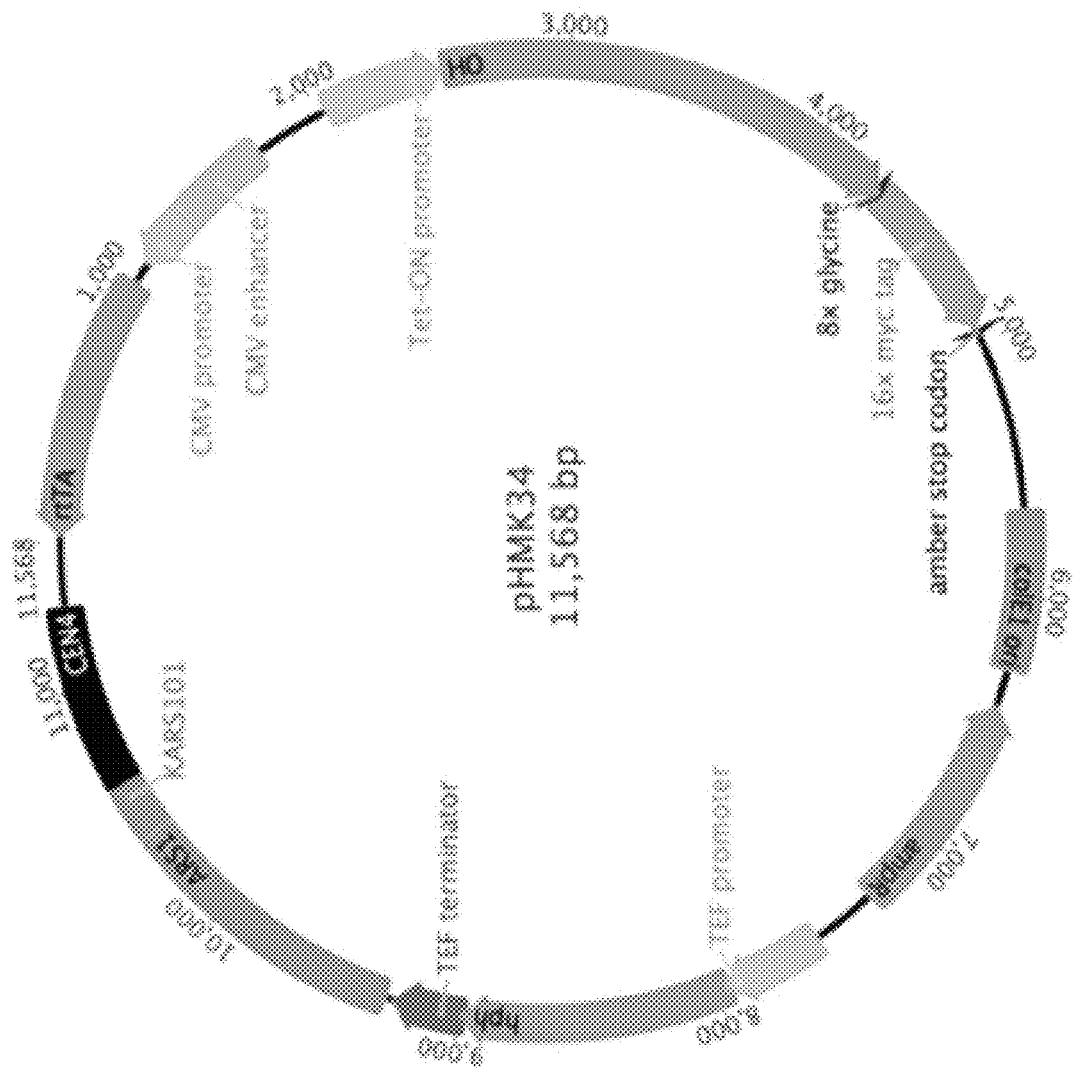
Figure 12:
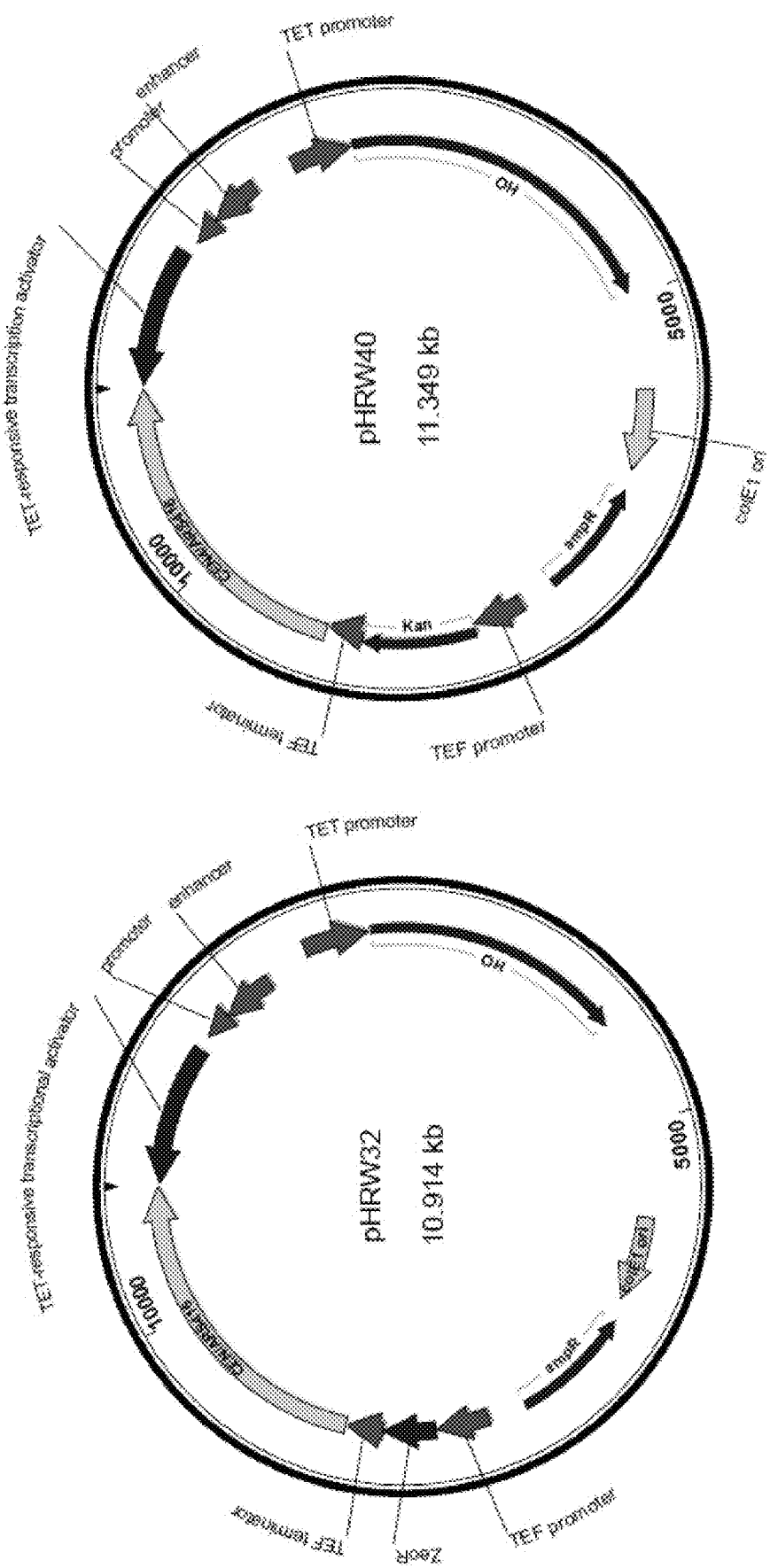
FIG. 12 shows the plasmid maps for a second set of HyPr plasmids pHRW32 with Zeocin resistance, the sequence of which is provided as SEQ ID NO: 16 and pHRW40 with Kanamycin resistance, the sequence of which is provided as SEQ ID NO: 15.

Construction of pBM5155, pHCT2, and pHMK34 pBM5155 (FIG. 4A) has been previously published and shown to facilitate the doxycycline-inducible gene expression in S. cerevisiae (Sabina and Johnston, 2009), but its sequence and the details of its construction by co-author CTH were not previously documented. pBM5155 was built using the backbone of pCM186 (Garí et al., 1997), which is a CEN plasmid containing all of the heterologous machinery for doxycycline-inducible expression of genes that are cloned into its NotI site, through several consecutive rounds of gap repair cloning in S. cerevisiae, followed by recovery and amplification in Escherichia coli by selection on LB+carbenicillin (or +ampicillin). Modifications of parts were introduced during PCR using oligonucleotides. The original rtTA transcription factor of pCM186, which is driven by a cytomegalovirus promoter, was excised and replaced with rtTA-M2 (Urlinger et al., 2000). The URA3 marker was replaced with a natMX4 marker (Goldstein and McCusker, 1999). An 8× glycine linker was added immediately downstream of the doxcyline-inducible promoter and immediately upstream of a 16× myc tag created from a 13× myc tag (Longtine et al., 1998) plus a 3× myc duplication created during gap repair. To improve stability in other yeast species, KARS101 from Kluyveromyces lactis (Fabiani et al., 2001) was added in addition to the S. cerevisiae CEN and ARS sequences already present. Modifications were made sequentially and confirmed by Sanger sequencing. The complete sequence of pBM5155 has been deposited in GenBank under accession KT725394.

pHCT2 (FIG. 4B) was built by PCR-amplifying S. cerevisiae HO using YCp50-HO-D6 (Russell et al., 1986) as a template, co-transforming that fragment with NotI-digested pBM5155 into S. cerevisiae, selecting on YPD+nat media, and recovering the resulting plasmid into E. coli. The natMX gene in pHCT2 was switched to the hphMX gene (Goldstein and McCusker, 1999) by amplifying the hph gene with oHWA230 and oHWA231, co-transforming the PCR product with AgeI-digested pHCT2 into *S. cerevisiae*, and selecting on YPD+hyg media. The resulting plasmid was recovered from yeast into bacteria, yielding pHMK34 (FIG. 4C). The sequence of pHCT2 was confirmed by 36-bp single-end Illumina sequencing, followed by assembly with VELVET (Zerbino and Birney, 2008). The manipulated region of pHMK34 was confirmed by PCR analysis and drug resistance. pHCT2 and pHMK34 sequences were deposited in GenBank under the accession numbers KT725395 and KT781077, respectively. Two additional plasmids, pHRW32 and pHRW40 with maps shown in FIG. 12 and sequences provided in SEQ ID NOs: 15 and 16 were also generated and have zeocin and G418 resistance to allow for further selection options. The pHRW40 plasmid is generally selected for on YPD plates with 400 ug/mL G418. The pHRW32 plasmid is generally selected for on YPD plates with 100 ug/mL Zeocin. In some cases, including for pHCT2 and pHMK34, drug concentrations must be optimized for the strains and species being used.

Induction of HO Expression and Mating

Plasmid-bearing cells were grown to saturation over 12-36 hours in 3 mL liquid YPD+drug. 1.5 mL of culture was discarded and replaced with 1.5 mL fresh liquid YPD+drug, and 3 μL of 10 mg/mL of filter-sterilized doxycycline dissolved in water was added. The culture was incubated for four hours to induce HO expression. Induced cells were pelleted, washed with YPD, and 5 μL each of two separate induced cultures were mixed in an Eppendorf tube and patched to a small area of a YPD agar plate to allow mating between newly formed MATa/MATa or MATα/MATα diploids. After 12-36 hours of incubation, a small amount of the patch was struck to or plated on YPD+hyg+nat agar.

Determination of Ploidy Via Flow Cytometry

Overnight cultures of putative tetraploids were used to inoculate fresh YPD. These cultures were grown until cultures reached exponential phase, then fixed with 70% ethanol and stained with SYBR Green (Thermo Fisher Scientific, Waltham, MA) as previously described (Fortuna et al., 1997); due to possible degradation issues encountered with the normal fixation protocol, the NRRL YB-210 and Wyeast #1007 strains were not heated, nor were they treated with Proteinase K. DNA content was determined with a Guava easyCyte (EMD Millipore, Darmstadt, Germany). Data were processed, analyzed, and visualized in R 2.14.

Confirmation of Hybridization with PCR-Based RFLP

Putative tetraploid hybrids had their genomic DNA extracted, and BRE5 was amplified using primers oHDP022 (González et al., 2008), oHDP023, and oHDP024. Resulting PCR products were digested with HaeIII (New England Biolabs, Ipswich, MA). Undigested PCR products were visualized on a 1.5% agarose gel, while digested PCR products were visualized on a 3% agarose gel.

Results

Figure 5:
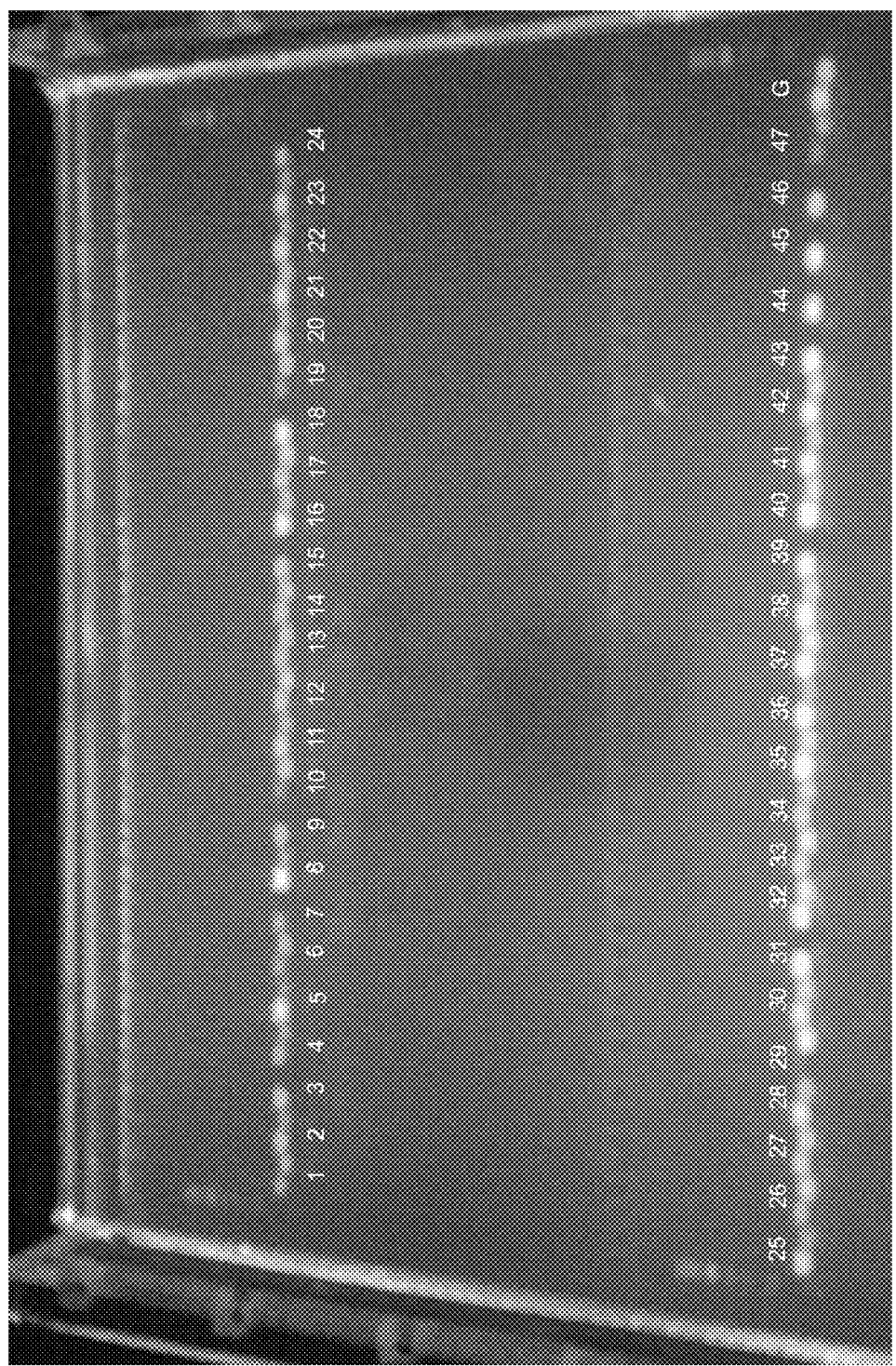
FIG. 5 shows pHCT2 facilitates MAT locus switching in hoΔ haploid strains of *Saccharomyces*. 47 numbered colonies had genomic DNA extracted by yeast colony PCR, and their mating-type locus analyzed by PCR as described in Table 2; the Wyeast #1007 German Ale strain was included as a diploid control (G). MATa produced the larger PCR product (left band for each colony), while MATα produced the smaller PCR product (right band for each colony). Presence of a band for only one of the strains' PCR reactions indicates a haploid cell. Colonies 3, 7, 9, 15, 18, 24, 31, 39, 43, 44, 45, and 46 only contained MATa, indicating that mating-type switching and subsequent autodiploidization did not occur in these colonies.

Doxycycline-Inducible Expression of HO in *Saccharomyces* pHCT2 was transformed into the stable haploid *S. cerevisiae* strain RM11-1a, and HO expression was induced with doxycycline. The induced culture was struck onto YPD+nat plates, and 47 colonies were screened by PCR of the mating-type locus (Gerstein et al., 2006); the Wyeast #1007 German Ale strain was included as a diploid control. 35 colonies produced bands consistent with the presence of both mating-type loci, while 12 colonies only produced one band from primers targeting MATα, the original mating type. The presence of both MATα and MATa are characteristic of a diploid cell, indicating that successful induction of HO by doxycycline, followed by mother-daughter or clonemate selfing, had occurred in the cell lineage to give rise to approximately 75% of the colonies (FIG. 5). Since HO was applied for an extended period of time during this experiment, rather than the normal tightly regulated process, it is formally possible (although highly unlikely) that a fraction of the remaining 25% of the cells could be MATα/MATα diploids rather than haploids.

Intraspecies Tetraploids are Selectable from Co-Cultured, HO-Induced Diploids

Figure 6:
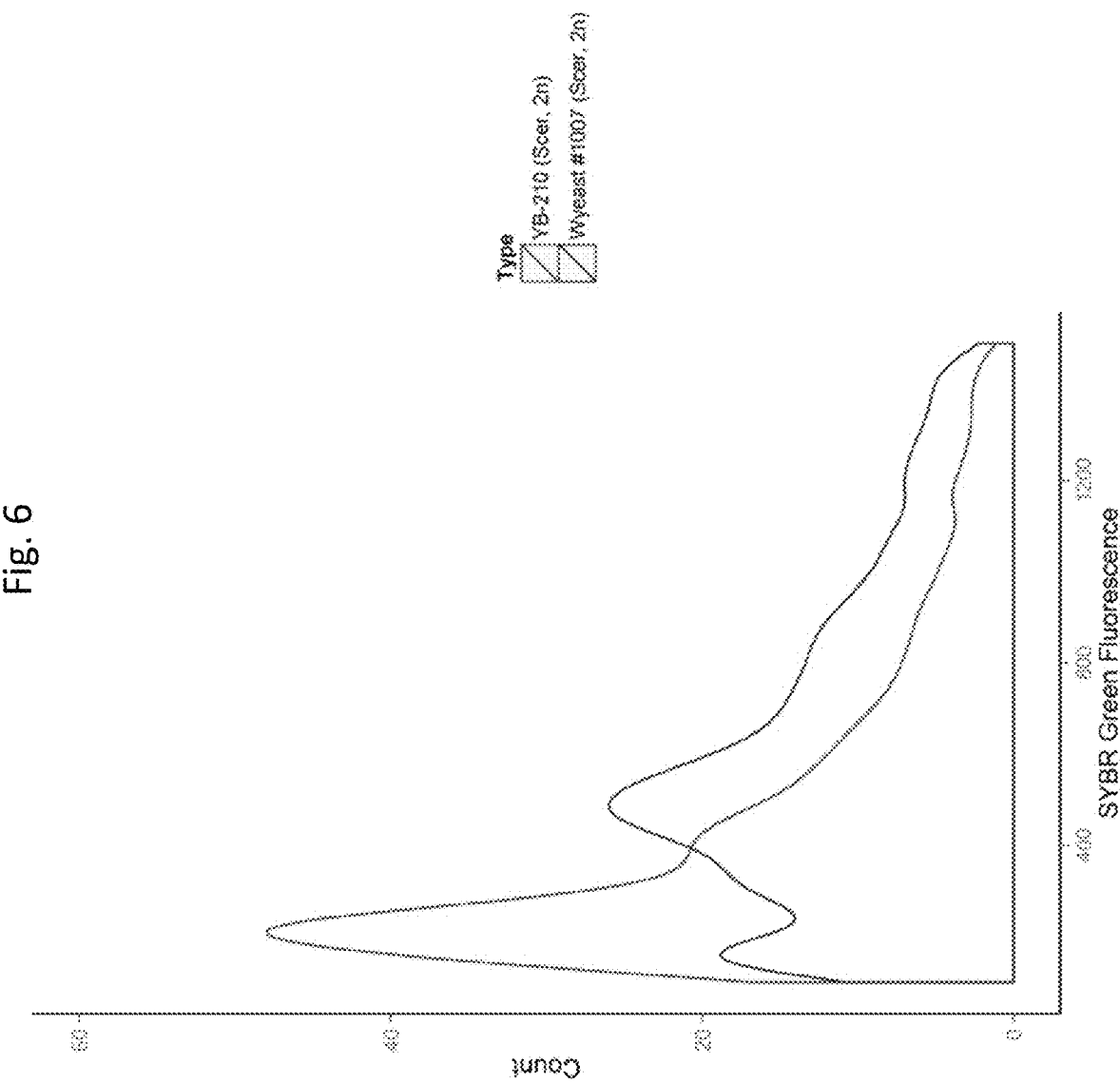
FIG. 6 shows NRRL YB-210 and Wyeast #1007 are approximately diploids. The standard fixation and staining procedure led to cellular degradation of both NRRL YB-210 and Wyeast #1007. Removing the heating and Proteinase K treatments prevented this degradation. NRRL YB-210 is known to be approximately diploid based on genome sequencing and tetrad dissection (Wolhbach et al, 2014). Different ratios of cells in two cell cycle phases (G1 and G2) are apparent in the figure; NRRL YB-210 has more cells in G1 of the cell cycle, while Wyeast #1007 has more cells in G2 of the cell cycle.

*S. cerevisiae* strains NRRL YB-210 and Ethanol Red are of biofuel interest due to their natural stress tolerance and routine use in ethanol production, respectively (Wohlbach et al., 2014). Strains containing pHMK34 and pHCT2 (Table 1), respectively, had HO expression induced with doxycycline and were co-cultured on YPD overnight at 30° C. The co-cultured patch was suspended in liquid YPD, and a $10^{-4}$ dilution was made with fresh YPD. 200 μL of dilution was plated onto each of three YPD+hyg+nat plates, while 2 μL was plated onto each of three YPD plates to estimate the frequency of hybridization (Table 3). We recovered an average of 9.67 double-drug-resistant tetraploids out of a calculated 6100 average viable cells per plate, or 0.158%. Flow cytometry of representative putative hybrids indicates DNA content consistent with tetraploidy when compared against known standards (FIG. 1A, FIG. 6). We note that induction of HO in diploids produces several possible genotypes by gene conversion, including MATa/MATa, MATα/MATα, and MATa/MATα diploids, but the HyPr method is expected to only select for those progeny that result from the mating of MATa/MATa diploids with MATα/MATα diploids that contain complementary marked plasmids. The HyPr method does not control which mating type is contributed by which parent.

TABLE 3

Recovery of double-drug-resistant colonies from induced, co-cultured *S. cerevisiae* strains

| Replicate | YPD + hyg + nat | YPD[1] |
| --- | --- | --- |
| A | 12 | 5200 |
| B | 7 | 6900 |
| C | 10 | 6200 |
| Mean ± SD | 9.67 ± 2.52 | 6100 ± 850 |

[1]Total YPD colonies were calculated from actual colony counts using dilution factors.

Interspecies Tetraploids are Selectable from Co-Cultured, HO-Induced Diploids

A German Ale strain of *S. cerevisiae* was transformed with pHCT2, while strains of *S. kudrivzevii*, *S. uvarum*, and *S. eubayanus* were transformed with pHMK34 (Table 1). HO expression was induced with doxycycline, and strains possessing complementary plasmids were co-cultured on YPD for up to 36 hours at room temperature. Patches were struck to YPD+hyg+nat, and resulting single double-drug-resistant colonies were grown in liquid YPD. Flow cytometry indicated a DNA content consistent with tetraploidy (FIGS. 1B-D, FIG. 6), and PCR-RFLP analysis confirmed these strains were hybrids between *S. cerevisiae* and the intended *Saccharomyces* species (FIG. 2).

Plasmids are Rapidly Lost in Non-Selective Media

Figure 3:
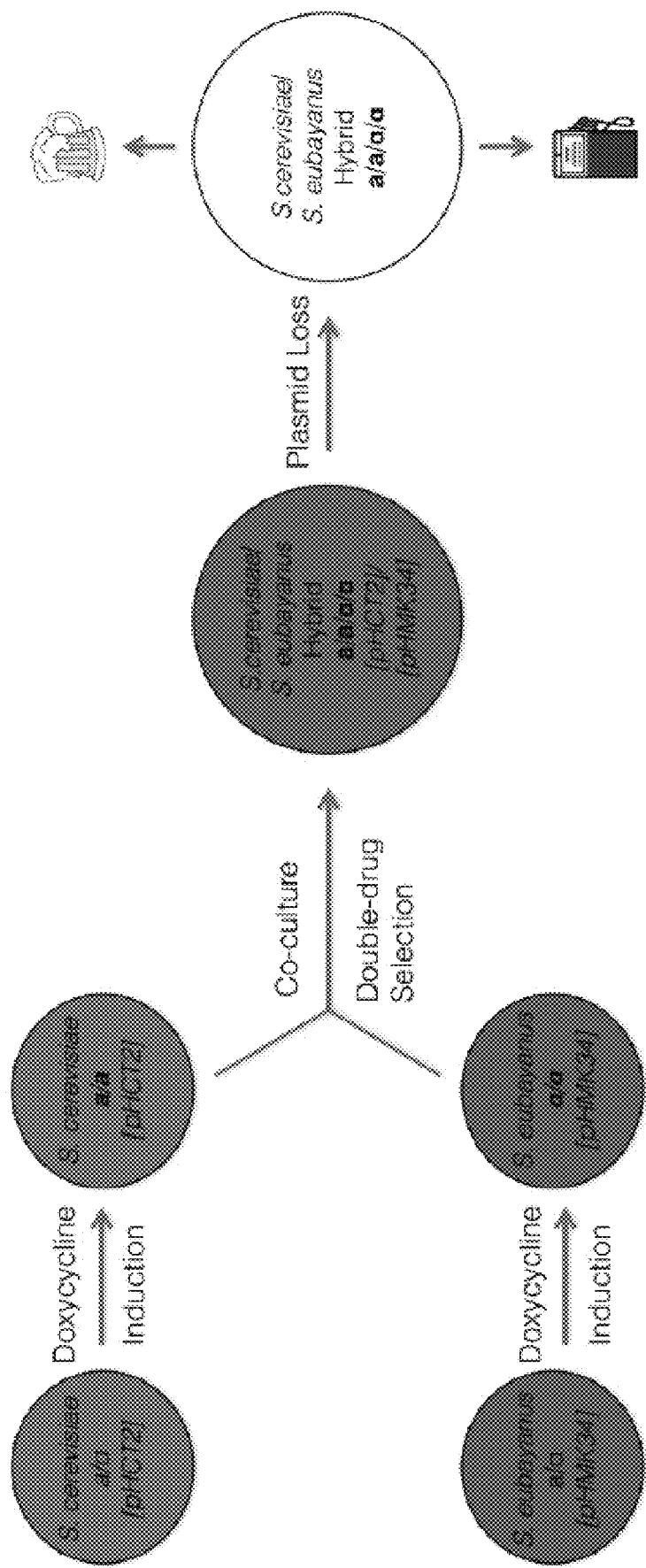
FIG. 3 shows an overview of the Hybrid Production (HyPr) method. Induction of HO expression by a doxycycline-inducible promoter in two diploid cultures, followed by co-culture and subsequent double-drug selection, will produce hybrids at a rate approaching 1 out of 1000 cells plated. Plasmids can then be easily cured or spontaneously lost to produce strains without genome modifications.
Figure 7:
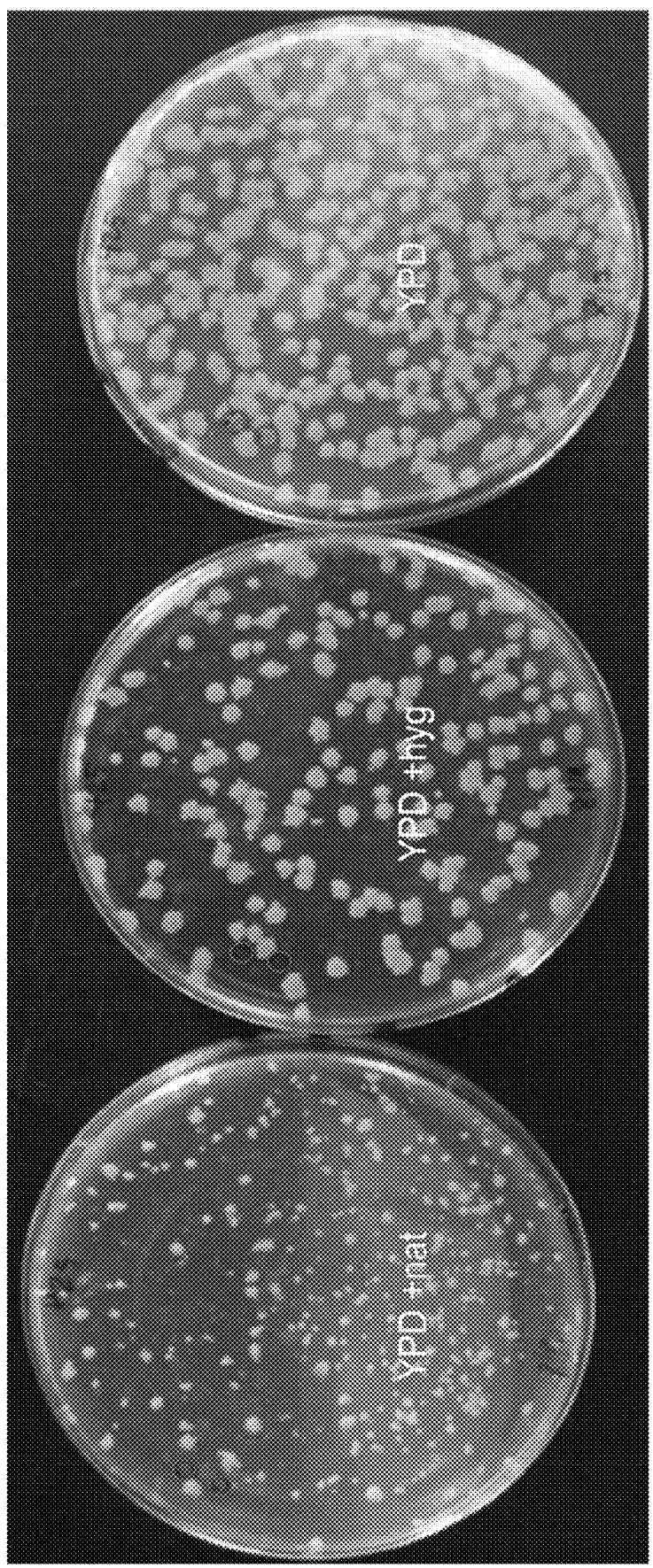
FIG. 7 shows HyPr hybrids without plasmids can be easily isolated. A saturated yHWA425 culture was diluted $10^{-2}$, and 10 μL of the dilution was plated to YPD (right). After three days of growth at room temperature, the plate was replicated to YPD+nat (left) and YPD +hyg (center). After two more days of growth, two colonies were picked on the basis of their drug sensitivity (circled colonies).

A saturated liquid non-selective culture of yHWA425, the synthetic *S. cerevisiae*×*S. eubayanus* hybrid (Table 1), was diluted $10^{-4}$, and 1 μL was plated onto each of three YPD plates. After incubation at room temperature for two days, these plates were replicated to YPD+hyg and YPD+nat plates. 54.9% of colonies lost pHMK34, while 63.8% of colonies lost pHCT2. Some colonies grew on YPD and were sensitive to both drugs (FIG. 7). These colonies were harvested from the YPD plate and were successfully struck for single colonies on YPD but not on YPD+hyg and YPD+nat (yHWA439), indicating that plasmid-free interspecies hybrids containing unmarked nuclear genomes can be readily obtained by this method.

pHCT2 and pHMK34 function similarly to previously constructed vectors that drive HO expression with the galactose-inducible promoter of GAL1 (Jensen and Herskowitz, 1984) and are valuable tools for researchers working with stable haploid prototrophic strains of Saccharomyces. More interestingly, pHCT2 and pHMK34 can be used together in a method called HyPr, which produces allotetraploid and autotetraploid Saccharomyces yeasts (FIG. 3). The HyPr success rate is high (around 1 out of 1000 plated cells) relative to the corresponding rate of rare mating between two diploids in a population, which has been estimated to be between 1 out of 1 million to 100 million cells (Gunge and Nakatomi, 1972). Moreover, the complementary markers on the plasmids themselves also provide the means to easily select allotetraploids. The high success rate, the ease of use in prototrophs, the lack of permanent genomic modification, and the capability of plasmid loss together make HyPr the ideal method for production of new designer hybrid strains for industrial fermentations, such as beer, wine, cider, and biofuel production. To introduce the utility of this approach, we have created novel S. cerevisiae×S. eubayanus, S. cerevisiae×S. kudriavzevii, and S. cerevisiae×S. uvarum strains, which are designed as synthetic lager, Belgian, and cider strains, respectively. We also created novel allohexaploid strains of S. cerevisiae×S. eubayanus×S. kudriavzevii, as well as six-species hybrids of S. cerevisiae×S. paradoxus×S. arboricola×S. uvarum×S. kudriavzevii×S. mikatae inferred to have 12 sets of chromosomes.

HyPr may also provide an alternative method for optimization via hybridization of Saccharomyces chassis strains to be used in a variety of synthetic biology applications. Selection of an appropriate chassis strain prior to the installation of genetic and metabolic modifications is a sound strategy, but prior work has often focused on screening existing strain libraries to find a chassis strain that fit a set of criteria (Jin et al., 2013). The meiotic sterility of many industrial strains of interest complicates the production of new Saccharomyces chassis strains because many strains do not produce viable spores. HyPr can be used to create chassis strains de novo from two strains with desirable traits, producing a new chassis strain with both desired characteristics without sporulation. As with a previous case where HO was induced in a sterile strain whose genome was predominantly S. uvarum (Schwartz et al., 2012), HyPr is expected to even enable hybridization of strains whose defect is in sporulation or chromosome segregation, rather than mating per se. This new chassis strain could then undergo optimization via selective conditions, further enhancing desired phenotypes of the chassis strain through aneuploidy and other mutations or through modification using various genome-editing techniques (Alexander et al., 2014; DiCarlo et al., 2013; Ryan et al., 2014).

Chassis strains made by HyPr lack drug markers and auxotrophies, both of which are desirable qualities in beverage and biofuel strains. Note that, while integration of any portion of the plasmid into the Saccharomyces genome is highly unlikely, it is formally possible that fragments of the plasmid could have integrated and conferred no detectable phenotype. Depending on the desired applications and safety regulations, any hybrids made using HyPr could have their genomes sequenced to ensure that all plasmid DNA had been eliminated from the strain, or other routine molecular approaches, such as PCR or Southern blots, could be taken to verify the absence of specific parts of the plasmid that were of concern.

Extensive prior work has shown that S. cerevisiae autotetraploid strains are relatively unstable, rapidly losing chromosomes to form aneuploid strains (Storchova, 2014). This loss occurs rapidly with genome content reduction to near-diploid levels in 200 to 800 generations (Gerstein et al., 2006). We expect autotetraploids made via HyPr to behave in a similar manner. This could, in fact, be a desirable trait for many applications, as placing an unstable tetraploid strain in a selective condition will influence which components of the genome are retained or lost from which parent, allowing for more rapid adaptation to that condition (Selmecki et al., 2015). Allopolyploids between Saccharomyces species have been identified from many different sources, including the isolation of lager beer strains (Dunn and Sherlock, 2008; Nakao et al., 2009; Walther et al., 2014). The reduction of genomic components has been observed in many cases. For example, S. cerevisiae×S. kudriavzevii hybrids isolated from brewing environments have selectively lost components of the S. kudriavzevii genome (Penis et al., 2012c), while certain S. cerevisiae×S. eubayanus hybrids used in lager beer production have lost whole S. cerevisiae chromosomes (Walther et al., 2014). We expect that allotetraploids made by HyPr will also evolve aneuploidy given enough time, but again, many of these aneuploidies may be advantageous in the conditions where they are evolved. A recent evolution experiment using interspecies hybrids demonstrated that genomic stability was reached within 30-50 generations (Pérez-Través et al., 2014a). Even though allopolyploid strains are less stable than diploid Saccharomyces strains, we note that the allopolyploid strains that form the backbone of the brewing industry are sufficiently stable for routine application in large-scale fermentations.

Finally, interspecies hybrids are also useful to address a variety of basic research questions in genetics and evolutionary biology. For example, interspecies hybrids have been especially useful for examining the relative effects of cis and trans variation on gene expression (Bullard et al., 2010; Swain Lenz et al., 2014; Tirosh et al., 2009; Wittkopp et al., 2004). In Saccharomyces, these studies have traditionally mated haploids with integrated complementary markers to make $F_1$ diploid hybrids. Our plasmid-based strategy may be preferable in strain backgrounds where gene targeting is inefficient or for high-throughput experiments. When diploidy is required, allotetraploid Saccharomyces that have not yet evolved aneuploidy or sterility can readily be sporulated readily to recover diploids (Greig et al., 2002; Gunge, 1966). In conclusion, this straightforward, robust approach allows the efficient construction of designer hybrids of Saccharomyces allotetraploids and autotetraploids, as well as strains with higher order ploidy, for numerous basic and applied uses.

REFERENCES

Alexander, W. G., Doering, D. T., Hittinger, C. T., 2014. High-efficiency genome editing and allele replacement in prototrophic and wild strains of Saccharomyces. Genetics 198, 859-866. doi:10.1534/genetics.114.170118

Almeida, P., Gonçalves, C., Teixeira, S., Libkind, D., Bontrager, M., Masneuf-Pomarède, I., Albertin, W., Durrens, P., Sherman, D. J., Marullo, P., Hittinger, C. T., Gonçalves, P., Sampaio, J. P., 2014. A Gondwanan imprint on global diversity and domestication of wine and cider yeast *Saccharomyces uvarum*. Nat. Commun. 5, 4044. doi: 10.1038/ncomms5044

Baker, E., Wang, B., Bellora, N., Peris, D., Hulfachor, A. B., Koshalek, J. A., Adams, M., Libkind, D., Hittinger, C. T., 2015. The genome sequence of *Saccharomyces eubayanus* and the domestication of lager-brewing yeasts. Mol. Biol. Evol. msv168-. doi:10.1093/molbev/msv168

Bardwell, L., 2004. A walk-through of the yeast mating pheromone response pathway. Peptides 25, 1465-1476. doi:10.1016/j.peptides.2003.10.022

Bing, J., Han, P.-J., Liu, W.-Q., Wang, Q.-M., Bai, F.-Y., 2014. Evidence for a Far East Asian origin of lager beer yeast. Curr. Biol. 24, R380-1. doi:10.1016/j.cub.2014.04.031

Brem, R. B., Yvert, G., Clinton, R., Kruglyak, L., 2002. Genetic dissection of transcriptional regulation in budding yeast. Science 296, 752-755. doi:10.1126/science.1069516

Bullard, J. H., Mostovoy, Y., Dudoit, S., Brem, R. B., 2010. Polygenic and directional regulatory evolution across pathways in *Saccharomyces*. Proc. Natl. Acad. Sci. U.S.A 107, 5058-63. doi:10.1073/pnas.0912959107

Casselton, L. A., Olesnicky, N. S., 1998. Molecular genetics of mating recognition in basidiomycete fungi. Microbiol. Mol. Biol. Rev. 62, 55-70.

Corran, H. S., 1975. A history of brewing. David & Charles.

DiCarlo, J. E., Norville, J. E., Mali, P., Rios, X., Aach, J., Church, G. M., 2013. Genome engineering in *Saccharomyces cerevisiae* using CRISPR-Cas systems. Nucleic Acids Res. 41, 4336-43. doi:10.1093/nar/gkt135

Dunn, B., Sherlock, G., 2008. Reconstruction of the genome origins and evolution of the hybrid lager yeast *Saccharomyces pastorianus*. Genome Res. 18, 1610-1623. doi: 10.1101/gr.076075.108

Fabiani, L., Irene, C., Aragona, M., Newlon, C. S., 2001. A DNA replication origin and a replication fork barrier used in vivo in the circular plasmid pKD1. Mol. Genet. Genomics 266, 326-35.

Fortuna, M., Joao Sousa, M., Corte-Real, M., Leao, C., 1997. UNIT 11.13 Cell cycle analysis of yeasts, in: Current Protocols in Cytometry.

Frank-Vaillant, M., Marcand, S., 2001. NHEJ regulation by mating type is exercised through a novel protein, Lif2p, essential to the ligase IV pathway. Genes Dev. 15, 3005-12. doi:10.1101/gad.206801

Garí, E., Piedrafita, L., Aldea, M., Herrero, E., 1997. A set of vectors with a tetracycline-regulatable promoter system for modulated gene expression in *Saccharomyces cerevisiae*. Yeast 13, 837-48. doi:10.1002/(SICI)1097-0061(199707)13:9<837::AID-YEA145>3.0.CO; 2-T Gerstein, A. C., Chun, H.-J. E., Grant, A., Otto, S. P., 2006. Genomic convergence toward diploidy in *Saccharomyces cerevisiae*. PLoS Genet. 2, e145. doi:10.1371/journal.pgen.0020145

Gietz, R. D., Woods, R. A., 2002. Transformation of yeast by lithium acetate/single-stranded carrier DNA/polyethylene glycol method. Methods Enzymol. 350, 87-96.

Glass, N. L., Grotelueschen, J., Metzenberg, R. L., 1990. *Neurospora crassa* A mating-type region. Proc. Natl. Acad. Sci. U.S.A 87, 4912-4916.

Glass, N. L., Jacobson, D. J., Shiu, P. K. T., 2000. The genetics of hyphal fusion and vegetative incompatibility in filamentous ascomycete fungi. Annu. Rev. Genet. 34, 165-186.

Goldstein, A. L., McCusker, J. H., 1999. Three new dominant drug resistance cassettes for gene disruption in *Saccharomyces cerevisiae*. Yeast 15, 1541-53. doi: 10.1002/(SICI)1097-0061(199910)15:14<1541::AID-YEA476>3.0.CO; 2-K González, S. S., Barrio, E., Querol, A., 2008. Molecular characterization of new natural hybrids of *Saccharomyces cerevisiae* and *S. kudriavzevii* in brewing. Appl. Environ. Microbiol. 74, 2314-2320. doi:10.1128/AEM.01867-07

Greig, D., Borts, R. H., Louis, E. J., Travisano, M., 2002. Epistasis and hybrid sterility in *Saccharomyces*. Proc. Biol. Sci. 269, 1167-71. doi:10.1098/rspb.2002.1989

Gunge, N., 1966. Breeding of bakers' yeast-Determination of the ploidy and an attempt to improve practical properties. Japanese J. Genet. 41, 203-214. doi:10.1266/jjg.41.203

Gunge, N., Nakatomi, Y., 1972. Genetic mechanisms of rare matings of the yeast *Saccharomyces cerevisiae* heterozygous for mating type. Genetics 70, 41-58.

Haber, J. E., 2012. Mating-type genes and MAT switching in *Saccharomyces cerevisiae*. Genetics 191, 33-64. doi: 10.1534/genetics.111.134577

Hebly, M., Brickwedde, A., Bolat, I., Driessen, M. R. M., de Hulster, E. A. F., van den Broek, M., Pronk, J. T., Geertman, J.-M., Daran, J.-M., Daran-Lapujade, P., 2015. *S. cerevisiae×S. eubayanus* interspecific hybrid, the best of both worlds and beyond. FEMS Yeast Res. 15. doi: 10.1093/femsyr/fov005

Herskowitz, I., Jensen, R. E., 1991. Putting the HO gene to work: practical uses for mating-type switching. Methods Enzymol. 194, 132-46.

Hittinger, C. T., 2013. *Saccharomyces* diversity and evolution: a budding model genus. Trends Genet. 29, 309-17. doi:10.1016/j.tig.2013.01.002

Hittinger, C. T., Gonçalves, P., Sampaio, J. P., Dover, J., Johnston, M., Rokas, A., 2010. Remarkably ancient balanced polymorphisms in a multi-locus gene network. Nature 464, 54-8. doi:10.1038/nature08791

Husnik, J. I., Volschenk, H., Bauer, J., Colavizza, D., Luo, Z., van Vuuren, H. J. J., 2006. Metabolic engineering of malolactic wine yeast. Metab. Eng. 8, 315-23. doi: 10.1016/j.ymben.2006.02.003

Jensen, R. E., Herskowitz, I., 1984. Directionality and regulation of cassette substitution in yeast. Cold Spring Harb. Symp. Quant. Biol. 49, 97-104. doi:10.1101/SQB.1984.049.01.013

Jin, M., Sarks, C., Gunawan, C., Bice, B. D., Simonett, S. P., Avanasi Narasimhan, R., Willis, L. B., Dale, B. E., Balan, V., Sato, T. K., 2013. Phenotypic selection of a wild *Saccharomyces cerevisiae* strain for simultaneous saccharification and co-fermentation of AFEX™ pretreated corn stover. Biotechnol. Biofuels 6, 108. doi:10.1186/1754-6834-6-108

John, B., 1990. Meiosis, Developmental and Cell Biology Series.

Kohl, K. P., Sekelsky, J., 2013. Meiotic and mitotic recombination in meiosis. Genetics 194, 327-34. doi:10.1534/genetics.113.150581

Krogerus, K., Magalhaes, F., Vidgren, V., Gibson, B., 2015. New lager yeast strains generated by interspecific hybridization. J. Ind. Microbiol. Biotechnol. 42, 769-78. doi: 10.1007/s10295-015-1597-6

Kronstad, J. W., Staben, C., 1997. Mating type in filamentous fungi. Annu. Rev. Genet. 31, 245-76. doi:10.1146/annurev.genet.31.1.245

Le Jeune, C., Lollier, M., Demuyter, C., Erny, C., Legras, J.-L., Aigle, M., Masneuf-Pomarède, I., 2007. Characterization of natural hybrids of *Saccharomyces cerevisiae* and *Saccharomyces bayanus* var. *uvarum*. FEMS Yeast Res. 7, 540-9. doi:10.1111/j.1567-1364.2007.00207.x Leducq, J.-B., Charron, G., Samani, P., Dubé, A. K., Sylvester, K., James, B., Almeida, P., Sampaio, J. P., Hittinger, C. T., Bell, G., Landry, C. R., 2014. Local climatic adaptation in a widespread microorganism. Proc. Biol. Sci. 281, 20132472. doi:10.1098/rspb.2013.2472

Libkind, D., Hittinger, C. T., Valério, E., Gonçalves, C., Dover, J., Johnston, M., Gonçalves, P., Sampaio, J. P., 2011. Microbe domestication and the identification of the wild genetic stock of lager-brewing yeast. Proc. Natl. Acad. Sci. U.S.A 108, 14539-44. doi:10.1073/pnas.1105430108

Liti, G., Carter, D. M., Moses, A. M., Warringer, J., Parts, L., James, S. a, Davey, R. P., Roberts, I. N., Burt, A., Koufopanou, V., Tsai, U., Bergman, C. M., Bensasson, D., O'Kelly, M. J. T., van Oudenaarden, A., Barton, D. B. H., Bailes, E., Nguyen, A. N., Jones, M., Quail, M. a, Goodhead, I., Sims, S., Smith, F., Blomberg, A., Durbin, R., Louis, E. J., 2009. Population genomics of domestic and wild yeasts. Nature 458, 337-41. doi:10.1038/nature07743

Liti, G., Peruffo, A., James, S. a, Roberts, I. N., Louis, E. J., 2005. Inferences of evolutionary relationships from a population survey of LTR-retrotransposons and telomeric-associated sequences in the *Saccharomyces* sensu stricto complex. Yeast 22, 177-92. doi:10.1002/yea.1200

Longtine, M. S., Mckenzie III, A., Demarini, D. J., Shah, N. G., Wach, A., Brachat, A., Philippsen, P., Pringle, J. R., 1998. Additional modules for versatile and economical PCR-based gene deletion and modification in *Saccharomyces cerevisiae*. Yeast 14, 953-961.

Maclean, C. J., Greig, D., 2008. Prezygotic reproductive isolation between *Saccharomyces cerevisiae* and *Saccharomyces paradoxus*. BMC Evol. Biol. 8, 1. doi:10.1186/1471-2148-8-1

Masneuf, I., Hansen, J., Groth, C., Piskur, J., Dubourdieu, D., 1998. New hybrids between *Saccharomyces* sensu stricto yeast species found among wine and cider production strains. Appl. Envir. Microbiol. 64, 3887-3892.

Mortimer, R. K., 2000. Evolution and variation of the yeast (*Saccharomyces*) genome. Genome Res. 10, 403-409. doi:10.1101/gr.10.4.403

Mortimer, R. K., Johnston, J. R., 1986. Genealogy of principal strains of the yeast genetic stock center. Genetics 113, 35-43.

Nakao, Y., Kanamori, T., Itoh, T., Kodama, Y., Rainieri, S., Nakamura, N., Shimonaga, T., Hattori, M., Ashikari, T., 2009. Genome sequence of the lager brewing yeast, an interspecies hybrid. DNA Res. 16, 115-29. doi:10.1093/dnares/dsp003

Pérez-Través, L., Lopes, C. A., Barrio, E., Querol, A., 2014a. Stabilization process in *Saccharomyces* intra and interspecific hybrids in fermentative conditions. Int. Microbiol. 17, 213-24. doi:10.2436/20.1501.01.224

Pérez-Través, L., Lopes, C. A., Barrio, E., Querol, A., 2012. Evaluation of different genetic procedures for the generation of artificial hybrids in *Saccharomyces* genus for winemaking. Int. J. Food Microbiol. 156, 102-11. doi:10.1016/j.ijfoodmicro.2012.03.008

Pérez-Través, L., Lopes, C. A., Querol, A., Barrio, E., 2014b. On the complexity of the *Saccharomyces bayanus* taxon: hybridization and potential hybrid speciation. PLoS One 9, e93729. doi:10.1371/journal.pone.0093729

Peris, D., Belloch, C., Lopandić, K., Álvarez-Pérez, J. M., Querol, A., Barrio, E., 2012a. The molecular characterization of new types of *Saccharomyces cerevisiae*×*S. kudriavzevii* hybrid yeasts unveils a high genetic diversity. Yeast 29, 81-91. doi:10.1002/yea.2891

Peris, D., Lopes, C. A., Arias, A., Barrio, E., 2012b. Reconstruction of the evolutionary history of *Saccharomyces cerevisiae*×*S. kudriavzevii* hybrids based on multilocus sequence analysis. PLoS One 7, e45527. doi:10.1371/journal.pone.0045527

Peris, D., Lopes, C. A., Belloch, C., Querol, A., Barrio, E., 2012c. Comparative genomics among *Saccharomyces cerevisiae*×*Saccharomyces* kudriavzevii natural hybrid strains isolated from wine and beer reveals different origins. BMC Genomics. doi:10.1186/1471-2164-13-407

Peris, D., Sylvester, K., Libkind, D., Gonçalves, P., Sampaio, J. P., Alexander, W. G., Hittinger, C. T., 2014. Population structure and reticulate evolution of *Saccharomyces eubayanus* and its lager-brewing hybrids. Mol. Ecol. 23, 2031-45. doi:10.1111/mec.12702

Piatkowska, E. M., Naseeb, S., Knight, D., Delneri, D., 2013. Chimeric protein complexes in hybrid species generate novel phenotypes. PLoS Genet. 9, e1003836. doi:10.1371/journal.pgen.1003836

Piotrowski, J. S., Nagarajan, S., Kroll, E., Stanbery, A., Chiotti, K. E., Kruckeberg, A. L., Dunn, B., Sherlock, G., Rosenzweig, F., 2012. Different selective pressures lead to different genomic outcomes as newly-formed hybrid yeasts evolve. BMC Evol. Biol. 12, 46. doi:10.1186/1471-2148-12-46

Russell, D. W., Jensen, R., Zoller, M. J., Burke, J., Errede, B., Smith, M., Herskowitz, I., 1986. Structure of the *Saccharomyces cerevisiae* HO gene and analysis of its upstream regulatory region. Mol. Cell. Biol. 6, 4281-94.

Ryan, O. W., Skerker, J. M., Maurer, M. J., Li, X., Tsai, J. C., Poddar, S., Lee, M. E., DeLoache, W., Dueber, J. E., Arkin, A. P., Cate, J. H. D., 2014. Selection of chromosomal DNA libraries using a multiplex CRISPR system. Elife e03703. doi:10.7554/eLife.03703

Sabina, J., Johnston, M., 2009. Asymmetric signal transduction through paralogs that comprise a genetic switch for sugar sensing in *Saccharomyces cerevisiae*. J. Biol. Chem. 284, 29635-29643. doi:10.1074/jbc.M109.032102

Sampaio, J. P., Gonçalves, P., 2008. Natural populations of *Saccharomyces* kudriavzevii in Portugal are associated with oak bark and are sympatric with *S. cerevisiae* and *S. paradoxus*. Appl. Environ. Microbiol. 74, 2144-2152. doi:10.1128/AEM.02396-07

Scannell, D. R., Zill, O. A., Rokas, A., Payen, C., Dunham, M. J., Eisen, M. B., Rine, J., Johnston, M., Hittinger, C. T., 2011. The awesome power of yeast evolutionary genetics: new genome sequences and strain resources for the *Saccharomyces* sensu stricto genus. G3 1, 11-25. doi:10.1534/g3.111.000273

Schwartz, K., Wenger, J. W., Dunn, B., Sherlock, G., 2012. APJ1 and GRE3 homologs work in concert to allow growth in xylose in a natural *Saccharomyces* sensu stricto hybrid yeast. Genetics 191, 621-32. doi:10.1534/genetics.112.140053

Selmecki, A. M., Maruvka, Y. E., Richmond, P. A., Guillet, M., Shoresh, N., Sorenson, A. L., De, S., Kishony, R., Michor, F., Dowell, R., Pellman, D., 2015. Polyploidy can drive rapid adaptation in yeast. Nature 519, 349-52. doi:10.1038/nature14187

Staben, C., Yanofsky, C., 1990. *Neurospora crassa* a mating-type region. Proc. Natl. Acad. Sci. U.S.A 87, 4917-21.

Storchova, Z., 2014. Ploidy changes and genome stability in yeast. Yeast 31, 421-30. doi:10.1002/yea.3037

Swain Lenz, D., Riles, L., Fay, J. C., 2014. Heterochronic meiotic misexpression in an interspecific yeast hybrid. Mol. Biol. Evol. 31, 1333-1342. doi:10.1093/molbev/msu098

Tirosh, I., Reikhav, S., Levy, A. A., Barkai, N., 2009. A yeast hybrid provides insight into the evolution of gene expression regulation. Science 324, 659-62. doi:10.1126/science.1169766

Urlinger, S., Baron, U., Thellmann, M., Hasan, M. T., Bujard, H., Hillen, W., 2000. Exploring the sequence space for tetracycline-dependent transcriptional activators: novel mutations yield expanded range and sensitivity. Proc. Natl. Acad. Sci. U.S.A 97, 7963-8. doi:10.1073/pnas.130192197

Van Heeckeren, W. J., Dorris, D. R., Struhl, K., 1998. The mating-type proteins of fission yeast induce meiosis by directly activating mei3 transcription. Mol. Cell. Biol. 18, 7317-26.

Walker, M. E., Gardner, J. M., Vystavelova, A., McBryde, C., Lopes, M. D. B., Jiranek, V., 2003. Application of the reuseable, KanMX selectable marker to industrial yeast: Construction and evaluation of heterothallic wine strains of *Saccharomyces cerevisiae*, possessing minimal foreign DNA sequences. FEMS Yeast Res. 4, 339-347. doi:10.1016/S1567-1356(03)00161-2

Walther, A., Hesselbart, A., Wendland, J., 2014. Genome sequence of *Saccharomyces carlsbergensis*, the world's first pure culture lager yeast. G3 4, 783-793. doi:10.1534/g3.113.010090

Wang, Q.-M., Liu, W.-Q., Liti, G., Wang, S.-A., Bai, F.-Y., 2012. Surprisingly diverged populations of *Saccharomyces cerevisiae* in natural environments remote from human activity. Mol. Ecol. 21, 5404-17. doi:10.1111/j.1365-294X.2012.05732.x Wittkopp, P. J., Haerum, B. K., Clark, A. G., 2004. Evolutionary changes in cis and trans gene regulation. Nature 430, 85-8. doi:10.1038/nature02698

Wohlbach, D. J., Rovinskiy, N., Lewis, J. A., Sardi, M., Schackwitz, W. S., Martin, J. A., Deshpande, S., Daum, C. G., Lipzen, A., Sato, T. K., Gasch, A. P., 2014. Comparative genomics of *Saccharomyces cerevisiae* natural isolates for bioenergy production. Genome Biol. Evol. 6, 2557-66.

Zerbino, D. R., Birney, E., 2008. Velvet: algorithms for de novo short read assembly using de Bruijn graphs. Genome Res. 18, 821-9. doi:10.1101/gr.074492.107

Example 2—Generation of Higher Order Polyploid Synthetic Yeast Cells

Figure 8:
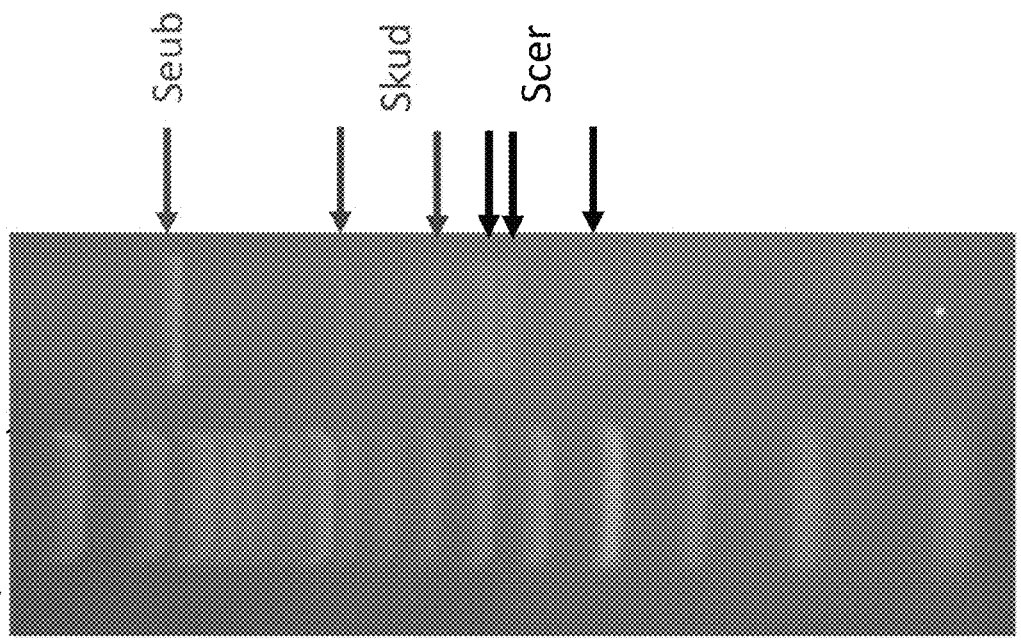
FIG. 8 shows how PCR and Restriction Fragment Long Polymorphism confirm the presence of three different genomes (*S. cerevisiae*×*S. kudriavzevii*×*S. eubayanus*) in a synthetic higher ploidy hybrid (likely an allohexaploid). The BRE5 PCR product was digested with HaeIII producing a pattern for each species contributing to this gene/genome, as described in FIG. 2.

Hybrid strain yHWA425 (*S. cerevisiae*×*S. eubayanus*) was passaged as described above such that it lost pHMK34 but retained pHCT2 (i.e. screening for nourseothricin-resistant but hygromycin-sensitive colonies by replica-plating). Strain yHWA425 was then crossed to strain yHWA354 (*S. kudriavzevii*), and triple hybrids resistant to both nourseothricin and hygromycin were selected using the protocols described above to generate allohexaploid strains yHWA451 and yHWA452 (*S. cerevisiae*×*S. eubayanus*×*S. kudriavzevii*). See Table 1. These triple hybrids were then passaged as described above such that both plasmids were lost, yielding yHWA455 and yHWA456 (*S. cerevisiae*×*S. eubayanus*×*S. kudriavzevii*). See Table 1. PCR and Restriction Fragment Long Polymorphism (RFLP) were used to confirm the presence of three different genomes (*S. cerevisiae*×*S. kudriavzevii*×*S. eubayanus*) in a synthetic higher ploidy hybrid (likely an allohexaploid) as shown in FIG. 8. The BRE5 PCR product was digested with HaeIII producing a pattern for each species contributing to this gene/genome, as described in FIG. 2 above.

Figure 9:
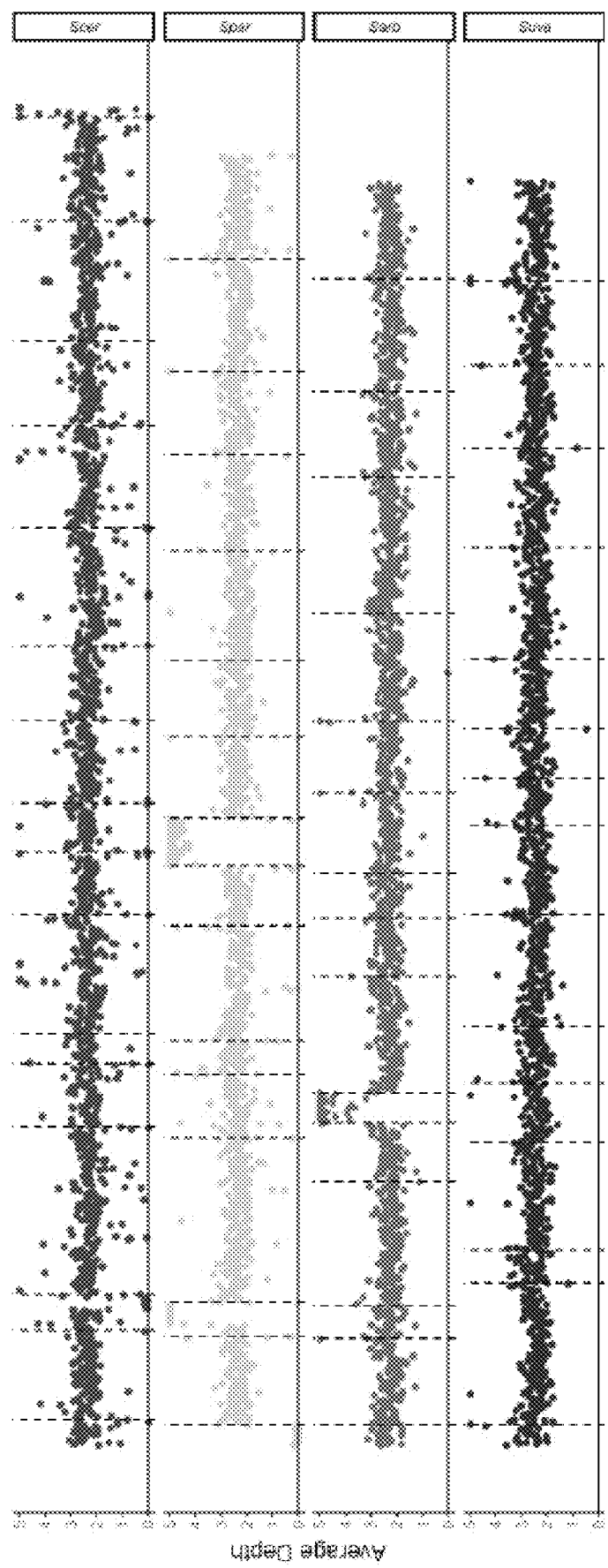
FIG. 9 is a set of sequencing analyses showing that the four species hybrid contains DNA sequences associated with each of the four parent species (*S. cerevisiae, S. paradoxus, S. arboricola* and *S. uvarum*, respectively from top to bottom in the figure). Notably the selected hybrid had increased read coverage for one parent and decreased read coverage for at least one parent on some of the chromosomes.
Figure 10:
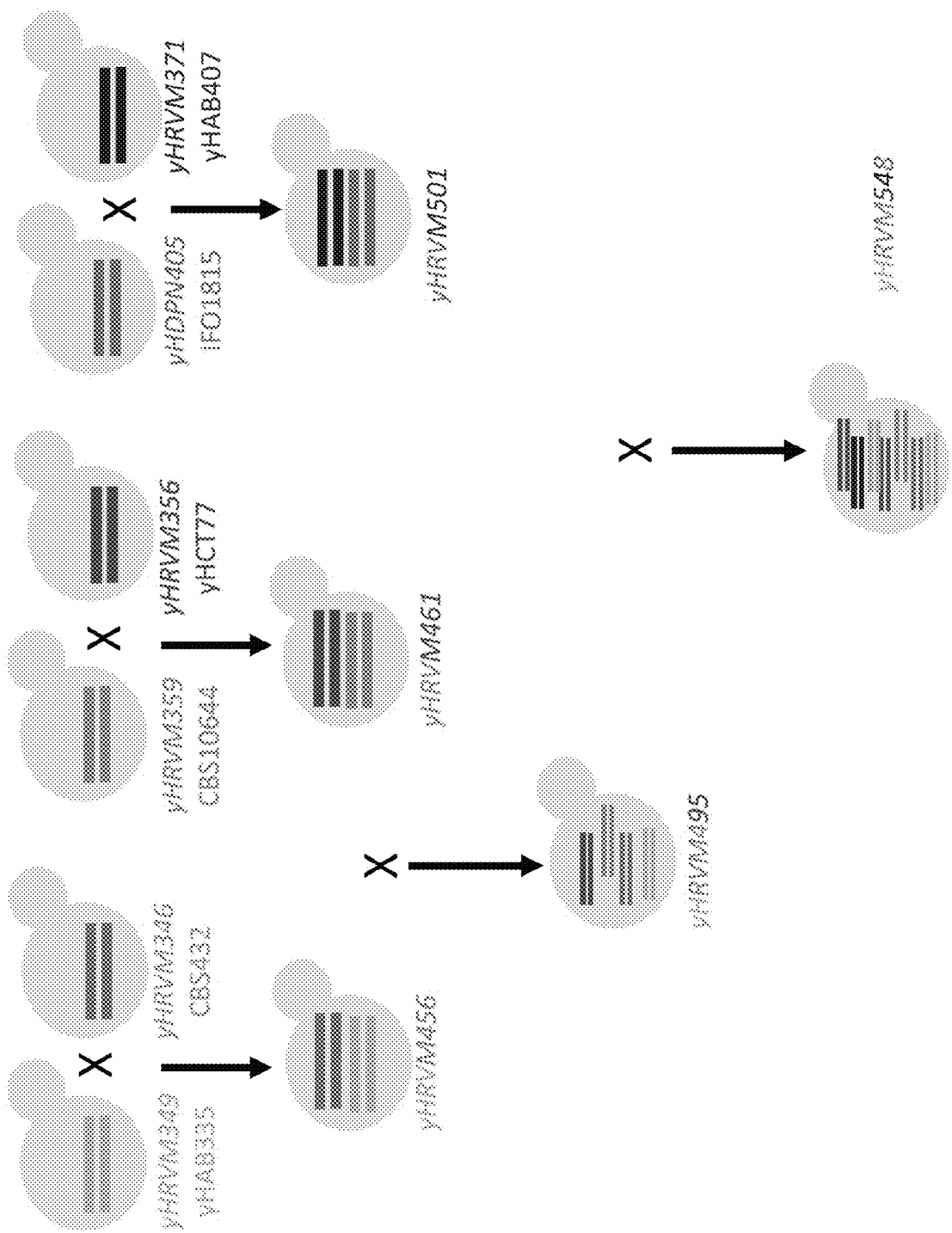
FIG. 10 is a schematic depiction of the scheme for making the 6 species hybrid indicating the strains used in the hybrid production scheme and the resulting allododecaploid yeast.

In addition to the hybrids described above, we were able to make higher order hybrids and have demonstrated both four and six species hybrids. These higher order hybrids were generated by taking two species hybrids such as those made above and further combining them. We generated several two-species hybrids, including *S. cerevisiae*×*S. paradoxus*, *S. arboricola*×*S. uvarum* and *S. mikatae*×*S. kudriavzevii*. Two of these two-species hybrids were then crossed and a four-species hybrid was selected. The four-species hybrid was confirmed by Illumina sequencing and analysis (as previously described in Peris et al. 2017 Biotechnol Biofuels 10:78) by comparison to the parents as shown in FIG. 9. As shown in FIG. 10, the four-species hybrid is a hybrid containing genetic material from *S. cerevisiae, S. paradoxus, S. arboricola, S. uvarum*. This four-species hybrid (*S. cerevisiae*×*S. paradoxus*×*S. arboricola*×*S. uvarum*) was then crossed with the two-species hybrid (*S. mikatae*×*S. kudriavzevii*) and a six-species hybrid was selected for and screened using Restriction Fragment Length Polymorphism analysis as shown in FIG. 11B to demonstrate that the hybrid was a 6-species hybrid (*S. cerevisiae*×*S. paradoxus*×*S. arboricola*×*S. uvarum*×*S. mikatae*×*S. kudriavzevii*). A photograph showing the diverse morphology of the 6 species hybrid is provided as FIG. 11A. This suggest chromosome instability, but work is continuing to demonstrate the variation within and ability to select for traits from these higher order hybrids. Thus, higher order hybrids can be made using the techniques described herein.

We claim:

1. A method of making a synthetic polyploid yeast cell comprising:
   i) introducing a first polynucleotide comprising a first promoter operably connected to an HO polynucleotide encoding a yeast Ho protein, a first selectable marker cassette, and a first yeast origin of replication into a first yeast cell from a first yeast hybrid to produce a first transformed yeast cell, wherein the first yeast hybrid and the first transformed yeast cell have a ploidy of at least 4N,
   ii) introducing a second polynucleotide comprising a second promoter operably connected to an HO polynucleotide encoding a yeast Ho protein, a second selectable marker cassette, and a second yeast origin of replication into a second yeast cell from a second yeast species or hybrid to produce a second transformed yeast cell,
   iii) co-culturing the first transformed yeast cell with the second transformed yeast cell to produce a mating mixture and allow for mating of the first transformed yeast cell and the second transformed yeast cell, and
   iv) selecting at least a portion of the mating mixture for the first selectable marker cassette and the second selectable marker cassette to select for a synthetic polyploid yeast cell produced by the mating of step iii,
   wherein the first selectable marker cassette and the second selectable marker cassette encode different selectable markers, wherein the first yeast cell and the second yeast cell are from different species of the same genus, and wherein the resulting synthetic polyploid yeast cell has a ploidy of at least 6N and comprises whole genomes from at least three different yeast species.

2. The method of claim 1, further comprising culturing the synthetic polyploid yeast cell in non-selective media to produce a synthetic polyploid yeast cell lacking the first polynucleotide and/or the second polynucleotide.

3. The method of claim 1, further comprising selecting the synthetic polyploid yeast cell under fermentation conditions to optimize the synthetic polyploid yeast cell for a fermentation process.

4. The method of claim 1, wherein the first promoter and/or the second promoter comprise an inducible promoter.

5. The method of claim 4, further comprising inducing the inducible promoter prior to step (iii).

6. The method of claim 1, wherein the at least three different yeast species are in the family Saccharomycetaceae.

7. The method of claim 1, wherein at least one of the at least three different yeast species are selected from the group consisting of *Saccharomyces cerevisiae*, *Saccharomyces paradoxus*, *Saccharomyces mikatae*, *Saccharomyces arboricola*, *Saccharomyces jurei*, *Saccharomyces kudriavzevii*, *Saccharomyces uvarum*, and *Saccharomyces eubayanus*.

8. The method of claim 1, wherein the synthetic polyploid yeast cell comprises chromosomes from 4 to 8 yeast species.

9. The method of claim 8, wherein the selected synthetic polyploid yeast cell comprises chromosomes from 5-6 yeast species.

10. The method of claim 1, wherein at least one of the first yeast cell or the second yeast cell is an ascomycete and the selected polyploid yeast cell comprises chromosomes from an ascomycete.

11. A kit for performing the method of claim 1 comprising:
    a first polynucleotide comprising a first promoter operably connected to an HO polynucleotide encoding a yeast Ho protein, a first selectable marker cassette, and a first yeast origin of replication, and
    a second polynucleotide comprising a second promoter operably connected to an HO polynucleotide encoding a yeast Ho protein, a second selectable marker cassette, and a second yeast origin of replication, and
    instructions for performing the method of claim 1,
    wherein the first selectable marker cassette and the second selectable marker cassette encode different selectable markers,
    and wherein the kit further comprises at least two different Saccharomycetaceae species at least one of which is a yeast hybrid having a ploidy of at least 4N.

12. The kit of claim 11, wherein the first promoter and/or the second promoter comprise an inducible promoter.

13. The kit of claim 11, further comprising doxycycline, nourseothricin, hygromycin, G418, fluoroacetamide, antifolates, Zeocin, or phleomycin.

14. The method of claim 1, wherein the first yeast hybrid comprises chromosomes from more than two different yeast species.

15. The method of claim 1, wherein at least one of the first yeast cell and the second yeast cell includes a *Saccharomyces eubayanus*.

16. A method of making a synthetic polyploid yeast cell comprising:
    i) introducing a first polynucleotide comprising a first promoter operably connected to an HO polynucleotide encoding a yeast Ho protein, a first selectable marker cassette, and a first yeast origin of replication into a first yeast cell from a first yeast hybrid to produce a first transformed yeast cell, wherein the first yeast hybrid and the first transformed yeast cell have a ploidy of at least 4N,
    ii) introducing a second polynucleotide comprising a second selectable marker cassette, and a second yeast origin of replication into a second yeast cell from a second haploid yeast species to produce a second transformed yeast cell, and
    iii) co-culturing the first transformed yeast cell with the second transformed yeast cell to produce a mating mixture and allow for mating of the first transformed yeast cell and the second transformed yeast cell, and
    iv) selecting at least a portion of the mating mixture for the first selectable marker cassette and the second selectable marker cassette to select for a synthetic polyploid yeast cell produced by the mating of step iii,
    wherein the first selectable marker cassette and the second selectable marker cassette encode different selectable markers, wherein the first yeast cell and the second yeast cell are from different species of the same genus, and wherein the resulting synthetic polyploid yeast cell has a ploidy of at least 6N and comprises whole genomes from at least three different yeast species.

17. The method of claim 16, wherein the first yeast hybrid comprises chromosomes from more than two different yeast species.

18. A method of making a synthetic polyploid yeast cell comprising:
    i) introducing a first polynucleotide comprising a first promoter operably connected to an HO polynucleotide encoding a yeast Ho protein, a first selectable marker cassette, and a first yeast origin of replication into a first yeast cell from a first yeast species or hybrid to produce a first transformed yeast cell,
    ii) introducing a second polynucleotide comprising a second promoter operably connected to an HO polynucleotide encoding a yeast Ho protein, a second selectable marker cassette, and a second yeast origin of replication into a second yeast cell from a second yeast species or hybrid to produce a second transformed yeast cell, iii) co-culturing the first transformed yeast cell with the second transformed yeast cell to produce a mating mixture and allow for mating of the first transformed yeast cell and the second transformed yeast cell, and iv) selecting at least a portion of the mating mixture for the first selectable marker cassette and the second selectable marker cassette to select for a first synthetic polyploid yeast cell produced by the mating of step iii, v) selecting for loss of one of the first selectable marker cassette or the second selectable marker cassette to produce a single marker first synthetic polyploidy yeast cell, vi) introducing a third polynucleotide comprising a third promoter operably connected to an HO polynucleotide encoding a yeast Ho protein, a third selectable marker cassette, and a third yeast origin of replication into a third yeast cell from a third yeast species or hybrid to produce a third transformed yeast cell, wherein the third selectable marker cassette is specific for a marker not found in the single marker first synthetic polyploidy yeast cell, vii) co-culturing the single marker first synthetic polyploid yeast cell selected in step v with the third transformed yeast cell of step vi to produce a mating mixture and allow for mating of the single marker first synthetic polyploid yeast cell and the third transformed yeast cell, and viii) selecting at least a portion of the mating mixture for the selectable marker cassette of the single marker first synthetic polyploidy yeast cell and the third selectable marker cassette to select for a second synthetic polyploid yeast cell produced by the mating of step vii, wherein the first selectable marker cassette and the second selectable marker cassette encode different selectable markers, wherein the first yeast cell, the second yeast cell, and the third yeast cell are each from different species of the same genus, and wherein the second synthetic polyploid yeast comprises whole genomes from at least three different yeast species and has a ploidy of at least 6N.

* * * * *

UNITED STATES PATENT AND TRADEMARK OFFICE
CERTIFICATE OF CORRECTION

| | | |
|---|---|---|
| PATENT NO. | : 11,913,016 B2 | Page 1 of 1 |
| APPLICATION NO. | : 15/805950 | |
| DATED | : February 27, 2024 | |
| INVENTOR(S) | : William Gerald Alexander et al. | |

It is certified that error appears in the above-identified patent and that said Letters Patent is hereby corrected as shown below:

In the Specification

Column 1, Line 66, "(Conan, 1975;" should be --(Corran, 1975;--.

In the Claims

Column 64, Line 1, "fora marker" should be --for a marker--.

Signed and Sealed this
Twenty-third Day of April, 2024

Katherine Kelly Vidal
*Director of the United States Patent and Trademark Office*

SEQUENCE LISTING

```
<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: Synthetic: MATa F primer

<400> SEQUENCE: 1
```

```
ctccacttca agtaagagtt tgggt                                                25

<210> SEQ ID NO 2
<211> LENGTH: 24
<212> TYPE: DNA
<213> ORGANISM: Artificial Sequence
<220> FEATURE:
<223> OTHER INFORMATION: Synthetic: MATalpha F primer

<400> SEQUENCE: 2
ttactcacag tttggctccg gtgt                                                 24

<210> SEQ ID NO 3
<211> LENGTH: 24
<212> TYPE: DNA
<213> ORGANISM: Artificial Sequence
<220> FEATURE:
<223> OTHER INFORMATION: Synthetic: Common MAT R primer

<400> SEQUENCE: 3
gaaccgcatg ggcagtttac cttt                                                 24

<210> SEQ ID NO 4
<211> LENGTH: 27
<212> TYPE: DNA
<213> ORGANISM: Artificial Sequence
<220> FEATURE:
<223> OTHER INFORMATION: Synthetic: oHDP022 primer

<400> SEQUENCE: 4
tgattatagc cacgggtgar atgttyt                                              27

<210> SEQ ID NO 5
<211> LENGTH: 27
<212> TYPE: DNA
<213> ORGANISM: Artificial Sequence
<220> FEATURE:
<223> OTHER INFORMATION: Synthetic: oHDP023 primer

<400> SEQUENCE: 5
tgattatagc cackggtgar atgtttt                                              27

<210> SEQ ID NO 6
<211> LENGTH: 27
<212> TYPE: DNA
<213> ORGANISM: Artificial Sequence
<220> FEATURE:
<223> OTHER INFORMATION: Synthetic: oHDP024 primer

<400> SEQUENCE: 6
ttcaktcatc aaytttgagg cccatgt                                              27

<210> SEQ ID NO 7
<211> LENGTH: 20
<212> TYPE: DNA
<213> ORGANISM: Artificial Sequence
<220> FEATURE:
<223> OTHER INFORMATION: Synthetic: oHWA230 primer

<400> SEQUENCE: 7
aaacgctccc ctcacagacg                                                      20

<210> SEQ ID NO 8
<211> LENGTH: 20
<212> TYPE: DNA
<213> ORGANISM: Artificial Sequence
```

```
<220> FEATURE:
<223> OTHER INFORMATION: Synthetic: oHWA231 primer

<400> SEQUENCE: 8
ctgggcagat gatgtcgagg                                                   20

<210> SEQ ID NO 9
<211> LENGTH: 60
<212> TYPE: DNA
<213> ORGANISM: Artificial Sequence
<220> FEATURE:
<223> OTHER INFORMATION: Synthetic: CTH993 primer

<400> SEQUENCE: 9
caaatacaca cactaaatta ccggatcaat tcgggggaaa aatgctttct gaaaacacga       60

<210> SEQ ID NO 10
<211> LENGTH: 51
<212> TYPE: DNA
<213> ORGANISM: Artificial Sequence
<220> FEATURE:
<223> OTHER INFORMATION: Synthetic: CTH994 primer

<400> SEQUENCE: 10
cctccacctc caccgttaat taacccgggg atccggcaga tgcgcgcacc t                51

<210> SEQ ID NO 11
<211> LENGTH: 586
<212> TYPE: PRT
<213> ORGANISM: Saccharomyces cerevisiae
<220> FEATURE:
<221> NAME/KEY: misc_feature
<222> LOCATION: (1)..(586)
<223> OTHER INFORMATION: Saccharomyces cerevisiae HO protein

<400> SEQUENCE: 11
```

Met Leu Ser Glu Asn Thr Thr Ile Leu Met Ala Asn Gly Glu Ile Lys
1               5                   10                  15

Asp Ile Ala Asn Val Thr Ala Asn Ser Tyr Val Met Cys Ala Asp Gly
            20                  25                  30

Ser Ala Ala Arg Val Ile Asn Val Thr Gln Gly Tyr Gln Lys Ile Tyr
        35                  40                  45

Asn Ile Gln Gln Lys Thr Lys His Arg Ala Phe Glu Gly Glu Pro Gly
    50                  55                  60

Arg Leu Asp Pro Arg Arg Thr Val Tyr Gln Arg Leu Ala Leu Gln
65                  70                  75                  80

Cys Thr Ala Gly His Lys Leu Ser Val Arg Val Pro Thr Lys Pro Leu
                85                  90                  95

Leu Glu Lys Ser Gly Arg Asn Ala Thr Lys Tyr Lys Val Arg Trp Arg
            100                 105                 110

Asn Leu Gln Gln Cys Gln Thr Leu Asp Gly Arg Ile Ile Ile Pro
        115                 120                 125

Lys Asn His His Lys Thr Phe Pro Met Thr Val Glu Gly Glu Phe Ala
    130                 135                 140

Ala Lys Arg Phe Ile Glu Glu Met Glu Arg Ser Lys Gly Glu Tyr Phe
145                 150                 155                 160

Asn Phe Asp Ile Glu Val Arg Asp Leu Asp Tyr Leu Asp Ala Gln Leu
                165                 170                 175

Arg Ile Ser Ser Cys Ile Arg Phe Gly Pro Val Leu Ala Gly Asn Gly
            180                 185                 190

Val Leu Ser Lys Phe Leu Thr Gly Arg Ser Asp Leu Val Thr Pro Ala
            195                 200                 205

Val Lys Ser Met Ala Trp Met Leu Gly Leu Trp Leu Gly Asp Ser Thr
    210                 215                 220

Thr Lys Glu Pro Glu Ile Ser Val Asp Ser Leu Asp Pro Lys Leu Met
225                 230                 235                 240

Glu Ser Leu Arg Glu Asn Ala Lys Ile Trp Gly Leu Tyr Leu Thr Val
                245                 250                 255

Cys Asp Asp His Val Pro Leu Arg Ala Lys His Val Arg Leu His Tyr
            260                 265                 270

Gly Asp Gly Pro Asp Glu Asn Arg Lys Thr Arg Asn Leu Arg Lys Asn
        275                 280                 285

Asn Pro Phe Trp Lys Ala Val Thr Ile Leu Lys Phe Lys Arg Asp Leu
    290                 295                 300

Asp Gly Glu Lys Gln Ile Pro Glu Phe Met Tyr Gly Glu His Ile Glu
305                 310                 315                 320

Val Arg Glu Ala Phe Leu Ala Gly Leu Ile Asp Ser Asp Gly Tyr Val
                325                 330                 335

Val Lys Lys Gly Glu Gly Pro Glu Ser Tyr Lys Ile Ala Ile Gln Thr
            340                 345                 350

Val Tyr Ser Ser Ile Met Asp Gly Ile Val His Ile Ser Arg Ser Leu
        355                 360                 365

Gly Met Ser Ala Thr Val Thr Thr Arg Ser Ala Arg Glu Glu Ile Ile
    370                 375                 380

Glu Gly Arg Lys Val Gln Cys Gln Phe Thr Tyr Asp Cys Asn Val Ala
385                 390                 395                 400

Gly Gly Thr Thr Ser Gln Asn Val Leu Ser Tyr Cys Arg Ser Gly His
                405                 410                 415

Lys Thr Arg Glu Val Pro Pro Ile Ile Lys Arg Glu Pro Val Tyr Phe
            420                 425                 430

Ser Phe Thr Asp Asp Phe Gln Gly Glu Ser Thr Val Tyr Gly Leu Thr
        435                 440                 445

Ile Glu Gly His Lys Asn Phe Leu Leu Gly Asn Lys Ile Glu Val Lys
    450                 455                 460

Ser Cys Arg Gly Cys Cys Val Gly Glu Gln Leu Lys Ile Ser Gln Lys
465                 470                 475                 480

Lys Asn Leu Lys His Cys Val Ala Cys Pro Arg Lys Gly Ile Lys Tyr
                485                 490                 495

Phe Tyr Lys Asp Trp Ser Gly Lys Asn Arg Val Cys Ala Arg Cys Tyr
            500                 505                 510

Gly Arg Tyr Lys Phe Ser Gly His His Cys Ile Asn Cys Lys Tyr Val
        515                 520                 525

Pro Glu Ala Arg Glu Val Lys Lys Ala Lys Asp Lys Gly Glu Lys Leu
    530                 535                 540

Gly Ile Thr Pro Glu Gly Leu Pro Val Lys Gly Pro Glu Cys Ile Lys
545                 550                 555                 560

Cys Gly Gly Ile Leu Gln Phe Asp Ala Val Arg Gly Pro His Lys Ser
                565                 570                 575

Cys Gly Asn Asn Ala Gly Ala Arg Ile Cys
            580                 585

<210> SEQ ID NO 12
<211> LENGTH: 1758
<212> TYPE: DNA

<213> ORGANISM: Saccharomyces cerevisiae
<220> FEATURE:
<221> NAME/KEY: misc_feature
<222> LOCATION: (1)..(1758)
<223> OTHER INFORMATION: Saccharomyces cerevisiae HO polynucleotide
      sequence

<400> SEQUENCE: 12

```
atgctttctg aaaacacgac tattctgatg gctaacggtg aaattaaaga catcgcaaac      60
gtcacggcta actcttacgt tatgtgcgca gatggctccg ctgcccgcgt cataaatgtc     120
acacagggct atcagaaaat ctataatata cagcaaaaaa ccaaacacag agcttttgaa     180
ggtgaacctg gtaggttaga tcccaggcgt agaacagttt atcagcgtct tgcattacaa     240
tgtactgcag gtcataaatt gtcagtcagg gtccctacca aaccactgtt ggaaaaaagt     300
ggtagaaatg ccaccaaata taagtgaga tggagaaatc tgcagcaatg tcagacgctt      360
gatggtagga taataataat tccaaaaaac catcataaga cattcccaat gacagttgaa     420
ggtgagtttg ccgcaaaacg cttcatgaaa gaaatggagc gctctaaagg agaatatttc     480
aactttgaca ttgaagttag agatttggat tatcttgatg ctcaattgag aatttctagc     540
tgcataagat ttggtccagt actcgcagga atggtgtttt atctaaatt tctcactgga      600
cgtagtgacc ttgtaactcc tgctgtaaaa agtatggctt ggatgcttgg tctgtggtta     660
ggtgacagta caacaaaaga gccagaaatc tcagtagata gcttggatcc taagctaatg     720
gagagtttaa gagaaaatgc gaaaatctgg ggtctctacc ttacggtttg tgacgatcac     780
gttccgctac gtgccaaaca tgtaaggctt cattatggag atggtccaga tgaaaacagg     840
aagacaagga atttgaggaa aaataatcca ttctggaaag ctgtcacaat tttaaagttt     900
aaaagggatc ttgatggaga gaagcaaatc cctgaattta tgtacggcga gcatatagaa     960
gttcgtgaag cattcttagc cggcttgatc gactcagatg ggtacgttgt gaaaaagggc    1020
gaaggccctg aatcttataa aatagcaatt caaactgttt attcatccat tatggacgga    1080
attgtccata tttcaagatc tcttggtatg tcagctactg tgacgaccag gtcagctagg    1140
gaggaaatca ttgaaggaag aaaagtccaa tgtcaattta catacgactg taatgttgct    1200
gggggaacaa cttcacagaa tgttttgtca tattgtcgaa gtggtcacaa acaagagaa     1260
gttccgccaa ttataaaaag gaacccgta tatttcagct tcacggatga tttccagggt     1320
gagagtactg tatatgggct tacgatagaa ggccataaaa atttcttgct ggcaacaaa     1380
atagaagtga atcatgtcg aggctgctgt gtgggagaac agcttaaaat atcacaaaaa    1440
aagaatctaa acactgtgt tgcttgtccc agaaagggaa tcaagtatt ttataaagat     1500
tggagtggta aaaatcgagt atgtgctaga tgctatggaa gatacaaatt cagcggtcat    1560
cactgtataa attgcaagta tgtaccagaa gcacgtgaag tgaaaaaggc aaaagacaaa    1620
ggcgaaaaat tgggcattac gcccgaaggt ttgccagtta aaggaccaga gtgtataaaa    1680
tgtggcggaa tcttcagttt tgatgctgtc cgcgggcctc ataagagttg tggtaacaac   1740
gcaggtgcgc gcatctgc                                                  1758
```

<210> SEQ ID NO 13
<211> LENGTH: 13
<212> TYPE: DNA
<213> ORGANISM: Saccharomyces cerevisiae
<220> FEATURE:
<221> NAME/KEY: misc_feature
<222> LOCATION: (1)..(13)
<223> OTHER INFORMATION: S. cerevisiae Ho recognition site in MATa

```
<400> SEQUENCE: 13
tttccgcaac agt                                                        13

<210> SEQ ID NO 14
<211> LENGTH: 13
<212> TYPE: DNA
<213> ORGANISM: Saccharomyces cerevisiae
<220> FEATURE:
<221> NAME/KEY: misc_feature
<222> LOCATION: (1)..(13)
<223> OTHER INFORMATION: S. cerevisiae Ho recognition site in MATa

<400> SEQUENCE: 14
ttcgcgcaac agt                                                        13

<210> SEQ ID NO 15
<211> LENGTH: 11349
<212> TYPE: DNA
<213> ORGANISM: Artificial Sequence
<220> FEATURE:
<223> OTHER INFORMATION: Synthetic: pHRW40(Kan), artificial plasmid
      sequence

<400> SEQUENCE: 15
gaattcttat tacgatcctc gcgcccccta cccaccgtac tcgtcaattc caagggcatc       60
ggtaaacatc tgctcaaact cgaagtcggc catatccaga gcgccgtagg gggcggagtc      120 gtgggggggta atcccggac ccggggaatc cccgtcccccc aacatgtcca gatcgaaatc    180
gtctagcgcg tcggcatgcg ccatcgccac gtcctcgccg tctaagtgga gctcgtcccc     240
caggctgaca tcggtcgggg gggccgtcga cagtctgcgc gtgtgtcccg cggggagaaa     300
ggacaggcgc ggagccgcca gccccgcctc ttcgggggcg tcgtcgtccg ggagatcgag     360
caggccctcg atggtagacc cgtaattgtt tttcgtacgc gcgcggctgt acgcggaccc     420
actttcacat ttaagttgtt tttctaatcc gcatatgatc aattcaaggc cgaataagaa     480
ggctggctct gcaccttggc gatcaaataa ttcgatagct tgtcgtaata atggcggcat     540
actatcagta gtaggtgttt ccctttcttc tttagcgact tgatgctctt gttcttccaa     600
tacgcaacct aaagtaaagt gccccacagc gctgagtgca tataatgcat tctctagtga     660
aaaaccttgt tggcataaaa aggctaattg attttcgaga gtttcatact gttttttctgt    720 aggccgtgta cctaaatgta cttttgctcc atcgcgatga cttagtaaag cacatctaaa     780
acttttagcg ttattacgta aaaaatcttg ccagctttcc ccttctaaag gcaaaagtg     840 agtatggtgc ctatctaaca tctcaatggg taaggcgtcg agcaaagccc gcttattttt    900
tacatgccaa tacaatgtag gctgctctac acctagcttc tgggcgagtt tacgggttgt    960
taaaccttcg attccgaccc cattaagcag ctctaatgcg ccgttaatca ctttactttt     1020
atctaatcta gacatatgaa ttaattcggg ccgcggaggc tggatcggtc ccggtgtctt    1080
ctatggaggt caaaacagcg tggatggcgt ctccaggcga tctgacggtt cactaaacga    1140
gctctgctta tatagacctc ccaccgtaca cgcctaccgc ccatttgcgt caatggggcg    1200
gagttgttac gacattttgg aaagtcccgt tgattttggt gccaaaacaa actcccattg    1260
acgtcaatgg ggtggagact tggaaatccc cgtgagtcaa accgctatcc acgcccattg    1320
atgtactgcc aaaaccgcat caccatggta atagcgatga ctaatacgta gatgtactgc    1380
caagtaggaa agtcccataa ggtcatgtac tgggcataat gccaggcggg ccatttaccg    1440
tcattgacgt caatagggggg cgtacttggc atatgataca cttgatgtac tgccaagtgg    1500
```

```
gcagtttagc gtaaatactc cacccattga cgtcaatgga aagtccctat ggcgttact   1560 atgggaacat acgtcattat tgacgtcaat gggcggggt cgttgggcgg tcagccaggc   1620
gggccattta ccgtaagtta tgtaacgcgg aactccatat atgggctatg aactaatgac   1680
cccgtaattg attactatta ataactagtc aataatcaat gtcaacatgg cggtaatgtt   1740
ggacatgagc caatataaat gtacatatta tgatatggat acaacgtatg caatgggcca   1800
agctcctcga gtaattgcgc ccacttctaa ataagcgaat ttcttatgat ttatgatttt   1860
tattattaaa taagttataa aaaaaataag tgtatacaaa ttttaaagtg actcttaggt   1920
tttaaaacga aaattcttgt tcttgagtaa ctctttcctg taggtcaggt tgctttctca   1980
ggtatagcat gaggtcgctc ttattgacca cacctctacc ggcagatcaa ttcctcgatc   2040
gagtttacca ctccctatca gtgatagaga aagtgaaag tcgagtttac cactccctat   2100
cagtgataga gaaaagtgaa agtcgagttt accactccct atcagtgata gagaaaagtg   2160
aaagtcgagt ttaccactcc ctatcagtga tagagaaaag tgaaagtcga gtttaccact   2220
ccctatcagt gatagagaaa agtgaaagtc gagtttacca ctccctatca gtgatagaga   2280
aaagtgaaag tcgagtttac cactccctat cagtgataga gaaagtgaa agtcgagctc   2340 ggtaccctat ggcatgcatg tgctctgtat gtatataaaa ctcttgtttt cttcttttct   2400
ctaaatattc tttccttata cattaggtcc tttgtagcat aaattactat acttctatag   2460
acacgcaaac acaaatacac acactaaatt accggatcaa ttcggggaa tgctttctga   2520 aaacacgact attctgatgg ctaacggtga aattaaagac atcgcaaacg tcacggctaa   2580
ctcttacgtt atgtgcgcag atggctccgc tgcccgcgtc ataaatgtca cacagggcta   2640
tcagaaaatc tataatatac agcaaaaaac caaacacaga gcttttgaag gtgaacctgg   2700
taggttagat cccaggcgta gaacagttta tcagcgtctt gcattacaat gtactgcagg   2760
tcataaattg tcagtcaggg tccctaccaa accactgttg gaaaaagtg gtagaaatgc   2820 caccaaatat aaagtgagat ggagaaatct gcagcaatgt cagacgcttg atggtaggat   2880
aataataatt ccaaaaaacc atcataagac attcccaatg acagttgaag gtgagtttgc   2940
cgcaaaacgc ttcatagaag aaatggagcg ctctaaagga gaatatttca actttgacat   3000
tgaagttaga gatttggatt atcttgatgc tcaattgaga atttctagct gcataagatt   3060
tggtccagta ctcgcaggaa atggtgtttt atctaaattt ctcactggac gtagtgacct   3120
tgtaactcct gctgtaaaaa gtatggcttg gatgcttggt ctgtggttag gtgacagtac   3180
aacaaaagag ccagaaatct cagtagatag cttggatcct aagctaatgg agagtttaag   3240
agaaaatgcg aaaatctggg gtctctacct tacggtttgt gacgatcacg ttccgctacg   3300
tgccaaacat gtaaggcttc attatggaga tggtccagat gaaaacagga agacaaggaa   3360
tttgaggaaa aataatccat tctggaaagc tgtcacaatt ttaaagttta aagggatct   3420 tgatggagag aagcaaatcc ctgaatttat gtacggcgag catatagaag ttcgtgaagc   3480
attcttagcc ggcttgatcg actcagatgg gtacgttgtg aaaaagggcg aaggccctga   3540
atcttataaa atagcaattc aaactgttta ttcatccatt atggacggaa ttgtccatat   3600
ttcaagatct cttggtatgt cagctactgt gacgaccagg tcagctaggg aggaaatcat   3660
tgaaggaaga aaagtccaat gtcaatttac atacgactgt aatgttgctg ggggaacaac   3720
ttcacagaat gttttgtcat attgtcgaag tggtcacaaa acaagagaag ttccgccaat   3780
tataaaaagg gaacccgtat atttcagctt cacggatgat ttccagggtg agagtactgt   3840
atatgggctt acgatagaag gccataaaaa tttcttgctt ggcaacaaaa tagaagtgaa   3900
```

```
atcatgtcga ggctgctgtg tgggagaaca gcttaaaata tcacaaaaaa agaatctaaa    3960
acactgtgtt gcttgtccca gaaagggaat caagtatttt tataaagatt ggagtggtaa    4020
aaatcgagta tgtgctagat gctatggaag atacaaattc agcggtcatc actgtataaa    4080
ttgcaagtat gtaccagaag cacgtgaagt gaaaaaggca aaagacaaag gcgaaaaatt    4140
gggcattacg cccgaaggtt tgccagttaa aggaccagag tgtataaaat gtggcggaat    4200
cttacagttt gatgctgtcc gcgggcctca taagagttgt ggtaacaacg caggtgcgcg    4260
catctgccgg atccccgggt taattaacgg tggaggtgga ggtggaggtg gaggtgaaca    4320
aaagctaatc tccgaggaag acttgaacgg tgaacaaaaa ttaatctcag aagaagactt    4380
gaacggactc gacggtgaac aaaagttgat ttctgaagaa gatttgaacg gtgaacaaaa    4440
gctaatctcc gaggaagact tgaacggtga acaaaaatta atctcagaag aagacttgaa    4500
cggactcgac ggtgaacaaa agttgatttc tgaagaagat ttgaacggtg aacaaaagct    4560
aatctccgag gaagacttga acggtgaaca aaaattaatc tcagaagaag acttgaacgg    4620
actcgacggt gaacaaaagt tgatttctga agaagatttg aacggtgaac aaaagctaat    4680
ctccgaggaa gacttgaacg gtgaacaaaa attaatctca gaagaagact tgaacggact    4740
cgacggtgaa caaaagttga tttctgaaga agatttgaac ggtgaacaaa agctaatctc    4800
cgaggaagac ttgaacggtg aacaaaaatt aatctcagaa gaagacttga acggactcga    4860
cggtgaacaa agttgatttc tgaagaaga tttgaacggt gaacaaaagc taatctccga    4920
ggaagacttg aacggtgaac aaaaattaat caatcactag tgaattcgcg ccacttctaa    4980
ataagcgaat tcttgagggt ccgcatcatg taattagtta tgtcacgctt acattcacgc    5040
cctcccccca tccgctctct aaccgaaaag aaggagttta gacaaacctga agtctaggtc    5100 cctatttatt tttttatagt tatgttagta ttaagaacgt tatttatatt tcaaattttt    5160
cttttttttc tgtacagacg cgtgtacgca tgtaacatta tactgaaaac cttgcttgag    5220
aaggttttgg gacgctcgaa ggctttaatt tgcggccaag cttggcgtaa tcatggtcat    5280
agctgtttcc tgtgtgaaat tgttatccgc tcacaattcc acacaacata cgagccggaa    5340
gcataaagtg taaagcctgg ggtgcctaat gagtgagcta actcacatta attgcgttgc    5400
gctcactgcc cgctttccag tcgggaaacc tgtcgtgcca gctgcattaa tgaatcggcc    5460
aacgcgcggg gagaggcggt ttgcgtattg ggcgctcttc cgcttcctcg ctcactgact    5520
cgctgcgctc ggtcgttcgg ctgcggcgag cggtatcagc tcactcaaag gcggtaatac    5580
ggttatccac agaatcaggg gataacgcag gaaagaacat gtgagcaaaa ggccagcaaa    5640
aggccaggaa ccgtaaaaag gccgcgttgc tggcgttttt ccataggctc cgcccccctg    5700
acgagcatca caaaaatcga cgctcaagtc agaggtggcg aaacccgaca ggactataaa    5760
gataccaggc gtttccccct ggaagctccc tcgtgcgctc tcctgttccg accctgccgc    5820
ttaccggata cctgtccgcc tttctccctt cgggaagcgt ggcgctttct catagctcac    5880
gctgtaggta tctcagttcg gtgtaggtcg ttcgctccaa gctgggctgt gtgcacgaac    5940 ccccgttca gcccgaccgc tgcgccttat ccggtaacta tcgtcttgag tccaacccgg    6000
taagacacga cttatcgcca ctggcagcag ccactggtaa caggattagc agagcgaggt    6060
atgtaggcgg tgctacagag ttcttgaagt ggtggcctaa ctacggctac actagaagga    6120
cagtatttgg tatctgcgct ctgctgaagc cagttacctt cggaaaaaga gttggtagct    6180
cttgatccgg caaacaaacc accgctggta gcggtggttt ttttgtttgc aagcagcaga    6240
```

```
ttacgcgcag aaaaaaagga tctcaagaag atcctttgat cttttctacg ggtctgacg   6300
ctcagtggaa cgaaaactca cgttaaggga ttttggtcat gagattatca aaaaggatct   6360
tcacctagat cctttttaaat taaaaatgaa gttttaaatc aatctaaagt atatatgagt   6420
aaacttggtc tgacagttac caatgcttaa tcagtgaggc acctatctca gcgatctgtc   6480
tatttcgttc atccatagtt gcctgactcc ccgtcgtgta gataactacg atacgggagg   6540
gcttaccatc tggccccagt gctgcaatga taccgcgaga cccacgctca ccggctccag   6600
atttatcagc aataaaccag ccagccggaa gggccgagcg cagaagtggt cctgcaactt   6660
tatccgcctc catccagtct attaattgtt gccgggaagc tagagtaagt agttcgccag   6720
ttaatagttt gcgcaacgtt gttgccattg ctacaggcat cgtggtgtca cgctcgtcgt   6780
ttggtatggc ttcattcagc tccggttccc aacgatcaag gcgagttaca tgatccccca   6840
tgttgtgcaa aaaagcggtt agctccttcg gtcctccgat cgttgtcaga agtaagttgg   6900
ccgcagtgtt atcactcatg gttatggcag cactgcataa ttctcttact gtcatgccat   6960
ccgtaagatg cttttctgtg actggtgagt actcaaccaa gtcattctga aatagtgta   7020
tgcggcgacc gagttgctct tgcccggcgt caatacggga taataccgcg ccacatagca   7080
gaactttaaa agtgctcatc attggaaaac gttcttcggg gcgaaaactc tcaaggatct   7140
taccgctgtt gagatccagt tcgatgtaac ccactcgtgc acccaactga tcttcagcat   7200
cttttacttt caccagcgtt tctgggtgag caaaaacagg aaggcaaaat gccgcaaaaa   7260
agggaataag ggcgacacgg aaatgttgaa tactcatact cttccttttt caatattatt   7320
gaagcattta tcagggttat tgtctcatga gcggatacat atttgaatgt atttagaaaa   7380
ataaacaaat aggggttccg cgcacatttc cccgaaaagt gccacctgac gtctaagaaa   7440
ccattattat catgacatta acctataaaa ataggcgtat cacgaggccc tttcgtcttc   7500
aagaattcag ctgaagcttc gtacgctgca ggtcgacgga tccccgggtt aattaaggcg   7560
cgccagatct gtttagcttg ccttgtcccc gccgggtcac ccggccagcg acatggaggc   7620
ccagaatacc ctccttgaca gtcttgacgt gcgcagctca ggggcatgat gtgactgtcg   7680
cccgtacatt tagcccatac atccccatgt ataatcattt gcatccatac attttgatgg   7740
ccgcacggcg cgaagcaaaa attacggctc ctcgctgcag acctgcgagc agggaaacgc   7800
tccccctcaca gacgcgttga attgtcccca cgccgcgccc ctgtagagaa atataaaagg   7860
ttaggatttg ccactgaggt tcttctttca tacttcct tttaaaatct tgctaggata   7920
cagttctcac atcacatccg aacataaaca accatgggta aggaaaagac tcacgtttcg   7980
aggccgcgat tgaattccaa catggatgct gatttatatg ggtataaatg gctcgcgat   8040
aatgtcgggc aatcaggtgc gacaatctat cgattgtatg ggaagcccga tgcgccagag   8100
ttgtttctga acatggcaa aggtagcgtt gccaatgatg ttacagatga gatggtcaga   8160
ctaaactggc tgacggaatt catgcctctt ccgaccatca agcattttat ccgtactcct   8220
gatgatgcat ggttactcac cactgcgatc cccggcaaaa cagcattcca ggtattagaa   8280
gaatatcctg attcaggtga aaatattgtt gatgcgctgg cagtgttcct gcgccggttg   8340
cattcgattc ctgtttgtaa ttgtcctttt aacagcgatc gcgtatttcg tctcgctcag   8400
gcgcaatcac gaatgaataa cggtttggtt gatgcgagtg attttgatga cgagcgtaat   8460
ggctggcctg ttgaacaagt ctggaaagaa atgcataagc ttttgccatt ctcaccggat   8520
tcagtcgtca ctcatggtga tttctcactt gataaccta ttttttgacga ggggaaatta   8580
ataggttgta ttgatgttgg acgagtcgga atcgcagacc gataccagga tcttgccatc   8640
```

```
ctatggaact gcctcggtga gttttctcct tcattacaga aacggctttt tcaaaaatat    8700
ggtattgata atcctgatat gaataaattg cagtttcatt tgatgctcga tgagttttc    8760 taatcagtac tgacaataaa aagattcttg ttttcaagaa cttgtcattt gtatagtttt    8820
tttatattgt agttgttcta ttttaatcaa atgttagcgt gatttatatt ttttttcgcc    8880
tcgacatcat ctgcccagat gcgaagttaa gtgcgcagaa agtaatatca tgcgtcaatc    8940
gtatgtgaat gctggtcgct atactgctgt cgattcgata ctaacgccgc catccagtgt    9000
cgaaaacgag ctcgaattca tcgatgatat cagatccact agtggcctat gcaattctca    9060
tgtttgacag cttatcatcg atcgtccaac tgcatggaga tgagtcgtgg caagaatacc    9120
aagagttcct cggtttgcca gttattaaaa gactcgtatt tccaaaagac tgcaacatac    9180
tactcagtgc agcttcacag aaacctcatt cgtttattcc cttgtttgat tcagaagcag    9240
gtgggacagg tgaactttg gattggaact cgatttctga ctgggttgga aggcaagaga    9300
gccccgagag cttacatttt atgttagctg gtggactgac gccagaaaat gttggtgatg    9360
cgcttagatt aaatggcgtt attggtgttg atgtaagcgg aggtgtggag acaaatggtg    9420
taaaagactc taacaaaata gcaaatttcg tcaaaaatgc taagaaatag gttattactg    9480
agtagtattt atttaagtat tgtttgtgca cttgcctgca agccttttga aaagcaagca    9540
taaaagatct aaacataaaa tctgtaaaat aacaagatgt aaagataatg ctaaatcatt    9600 tggcttttg attgattgta caggaaaata tacatcgcag ggggttgact tttaccattt    9660
caccgcaatg gaatcaaact tgttgaagag aatgttcaca ggcgcatacg ctacaatgac    9720
ccgattcttg ctagcctttt ctcggtcttg caaacaaccg ccggcagctt agtatataaa    9780
tacacatgta catacctctc tccgtatcct cgtaatcatt tcttgtatt tatcgtcttt    9840 tcgctgtaaa aactttatca cacttatctc aaatacactt attaaccgct tttactatta    9900
tcttctacgc tgacagtaat atcaaacagt gacacatatt aaacacgtg gtttctttgc    9960 ataaacacca tcagcctcaa gtcgtcaagt aaagatttcg tgttcatgca gatagataac   10020
aatctatatg ttgataatta gcgttgcctc atcaatgcga gatccgttta accggaccct   10080
agtgcactta ccccacgttc ggtccactgt gtgccgaaca tgctccttca ctatttaac   10140 atgtggaatt atcgatgccg gtgttattct tgctatgata ggccatcgaa tgttaaaggg   10200
aagatttatt gttttgccct ttaaagacga atttggaccg tgaatgttta ataattctc   10260 atgtttgaca gcttatcatc gaactctaag aggtgatact tatttactgt aaaactgtga   10320
cgataaaacc ggaaggaaga ataagaaaac tcgaactgat ctataatgcc tattttctgt   10380
aaagagttta agctatgaaa gcctcggcat tttggccgct cctaggtagt gctttttttc   10440
caaggacaaa acagtttctt tttcttgagc aggttttatg tttcggtaat cataaacaat   10500
aaataaatta tttcatttat gtttaaaaat aaaaaataaa aagtattttt aattttaa    10560 aaaagttgat tataagcatg tgaccttttg caagcaatta aattttgcaa tttgtgattt   10620
taggcaaaag ttacaatttc tggctcgtgt aatatatgta tgctaaagtg aacttttaca   10680
aagtcgatat ggacttagtc aaaagaaatt ttcttaaaaa tatatagcac tagccaattt   10740
agcacttctt tatgagatat attatagact ttattaagcc agatttgtgt attatatgta   10800
tttacccggc gaatcatgga catacattct gaaataggta atattctcta tggtgagaca   10860
gcatagataa cctaggatac aagttaaaag ctagtactgt tttgcagtaa ttttttttctt   10920 ttttataaga atgttaccac ctaaataagt tataaagtca atagttaagt ttgatatttg   10980
```

| | |
|---|---|
| attgtaaaat accgtaatat atttgcatga tcaaaaggct caatgttgac tagccagcat | 11040 |
| gtcaaccact atattgatca ccgatatatg gacttccaca ccaactagta atatgacaat | 11100 |
| aaattcaaga tattcttcat gagaatggcc cagcgatata tgcggtgtga ataccgcac | 11160 |
| agatgcgtaa ggagaaaata ccgcatcagg cgccattcgc cattcaggct gcgcaactgt | 11220 |
| tgggaagggc gatcggtgcg ggcctcttcg ctattacgcc agctggcgaa aggggggatgt | 11280 |
| gctgcaaggc gattaagttg ggtaacgcca gggttttccc agtcacgacg ttgtaaaacg | 11340 |
| acggccagt | 11349 |

<210> SEQ ID NO 16
<211> LENGTH: 10914
<212> TYPE: DNA
<213> ORGANISM: Artificial Sequence
<220> FEATURE:
<223> OTHER INFORMATION: Synthetic: pHRW32(Zeo), Artificial plasmid sequence

<400> SEQUENCE: 16

| | |
|---|---|
| gaattcttat tacgatcctc gcgcccccta cccaccgtac tcgtcaattc caagggcatc | 60 |
| ggtaaacatc tgctcaaact cgaagtcggc catatccaga cgccgtagg gggcggagtc | 120 |
| gtgggggggta atcccggac ccggggaatc ccgtccccc aacatgtcca gatcgaaatc | 180 |
| gtctagcgcg tcggcatgcg ccatcgccac gtcctgccg tctaagtgga gctcgtcccc | 240 |
| caggctgaca tcggtcgggg gggccgtcga cagtctgcgc gtgtgtcccg cggggagaaa | 300 |
| ggacaggcgc ggagccgcca gccccgcctc ttcgggggcg tcgtcgtccg ggagatcgag | 360 |
| caggccctcg atggtagacc cgtaattgtt tttcgtacgc gcgcggctgt acgcggaccc | 420 |
| actttcacat ttaagttgtt tttctaatcc gcatatgatc aattcaaggc cgaataagaa | 480 |
| ggctggctct gcaccttggc gatcaaataa ttcgatagct tgtcgtaata atggcggcat | 540 |
| actatcagta gtaggtgttt ccctttcttc tttagcgact tgatgctctt gttcttccaa | 600 |
| tacgcaacct aaagtaaagt gccccacagc gctgagtgca tataatgcat tctctagtga | 660 |
| aaaaccttgt tggcataaaa aggctaattg attttcgaga gtttcatact gttttttctgt | 720 |
| aggccgtgta cctaaatgta cttttgctcc atcgcgatga cttagtaaag cacatctaaa | 780 |
| acttttagcg ttattacgta aaaaatcttg ccagctttcc ccttctaaag ggcaaaagtg | 840 |
| agtatggtgc ctatctaaca tctcaatggg taaggcgtcg agcaaagccc gcttattttt | 900 |
| tacatgccaa tacaatgtag gctgctctac acctagcttc tgggcgagtt tacgggttgt | 960 |
| taaaccttcg attccgaccc cattaagcag ctctaatgcg ccgttaatca ctttactttt | 1020 |
| atctaatcta gacatatgaa ttaattcggg ccgcggaggc tggatcggtc ccggtgtctt | 1080 |
| ctatggaggt caaaacagcg tggatggcgt ctccaggcga tctgacggtt cactaaacga | 1140 |
| gctctgctta tatagacctc ccaccgtaca cgcctaccgc ccatttgcgt caatggggcg | 1200 |
| gagttgttac gacattttgg aaagtccgt tgatttggt gccaaaacaa actcccattg | 1260 |
| acgtcaatgg ggtggagact tggaaatccc cgtgagtcaa accgctatcc acgcccattg | 1320 |
| atgtactgcc aaaaccgcat caccatggta tagcgatga ctaatacgta gatgtactgc | 1380 |
| caagtaggaa agtcccataa ggtcatgtac tgggcataat gccaggcggg ccatttaccg | 1440 |
| tcattgacgt caatagggg cgtacttggc atatgataca cttgatgtac tgccaagtgg | 1500 |
| gcagtttagc gtaaatactc caccccattga cgtcaatgga aagtccctat tggcgttact | 1560 |
| atgggaacat acgtcattat tgacgtcaat gggcgggggt cgttgggcgg tcagccaggc | 1620 |

-continued

```
gggccattta ccgtaagtta tgtaacgcgg aactccatat atgggctatg aactaatgac    1680
cccgtaattg attactatta ataactagtc aataatcaat gtcaacatgg cggtaatgtt    1740
ggacatgagc caatataaat gtacatatta tgatatggat acaacgtatg caatgggcca    1800
agctcctcga gtaattcgcg ccacttctaa ataagcgaat ttcttatgat ttatgatttt    1860
tattattaaa taagttataa aaaaaataag tgtatacaaa ttttaaagtg actcttaggt    1920
tttaaaacga aaattcttgt tcttgagtaa ctctttcctg taggtcaggt tgctttctca    1980
ggtatagcat gaggtcgctc ttattgacca cacctctacc ggcagatcaa ttcctcgatc    2040
gagtttacca ctccctatca gtgatagaga aaagtgaaag tcgagtttac cactccctat    2100
cagtgataga gaaaagtgaa agtcgagttt accactccct atcagtgata gagaaaagtg    2160
aaagtcgagt ttaccactcc ctatcagtga tagagaaaag tgaaagtcga gtttaccact    2220
ccctatcagt gatagagaaa agtgaaagtc gagtttacca ctccctatca gtgatagaga    2280
aaagtgaaag tcgagtttac cactccctat cagtgataga gaaaagtgaa agtcgagctc    2340
ggtaccctat ggcatgcatg tgctctgtat gtatataaaa ctcttgtttt cttcttttct    2400
ctaaatattc tttccttata cattaggtcc tttgtagcat aaattactat acttctatag    2460
acacgcaaac acaaatacac acactaaatt accggatcaa ttcgggggaa tgctttctga    2520
aaacacgact attctgatgg ctaacggtga attaaagac atcgcaaacg tcacggctaa     2580
ctcttacgtt atgtgcgcag atggctccgc tgcccgcgtc ataaatgtca cagggctaa    2640
tcagaaaatc tataatatac agcaaaaaac caaacacaga gcttttgaag gtgaacctgg    2700
taggttagat cccaggcgta gaacagttta tcagcgtctt gcattacaat gtactgcagg    2760
tcataaattg tcagtcaggg tccctaccaa accactgttg gaaaaagtg gtagaaatgc     2820
caccaaatat aaagtgagat ggagaaatct gcagcaatgt cagacgcttg atggtaggat    2880
aataataatt ccaaaaaacc atcataagac attcccaatg acagttgaag gtgagtttgc    2940
cgcaaaacgc ttcatagaag aaatggagcg ctctaaagga gaatatttca actttgacat    3000
tgaagttaga gatttggatt atcttgatgc tcaattgaga atttctagct gcataagatt    3060
tggtccagta ctcgcaggaa atggtgtttt atctaaattt ctcactggac gtagtgacct    3120
tgtaactcct gctgtaaaaa gtatggcttg gatgcttggt ctgtggttag gtgacagtac    3180
aacaaaagag ccagaaatct cagtagatag cttggatcct aagctaatgg agagtttaag    3240
agaaaatgcg aaaatctggg gtctctacct tacggtttgt gacgatcacg ttccgctacg    3300
tgccaaacat gtaaggcttc attatggaga tggtccagat gaaaacagga agacaaggaa    3360
tttgaggaaa aataatccat tctggaaagc tgtcacaatt ttaaagttta aagggatct    3420
tgatggagaa gcaaatcc ctgaatttat gtacggcgag catatagaag ttcgtgaagc     3480
attcttagcc ggcttgatcg actcagatgg gtacgttgtg aaaaagggcg aaggccctga    3540
atcttataaa atagcaattc aaactgttta ttcatccatt atggacggaa ttgtccatat    3600
ttcaagatct cttggtatgt cagctactgt gacgaccagg tcagctaggg aggaaatcat    3660
tgaaggaaga aaagtccaat gtcaatttac atacgactgt aatgttgctg ggggaacaac    3720
ttcacagaat gttttgtcat attgtcgaag tggtcacaaa acaagagaag ttccgccaat    3780
tataaaaagg gaacccgtat atttcagctt cacggatgat ttccagggtg agagtactgt    3840
atatgggctt acgatagaag gccataaaaa tttcttgctt ggcaacaaaa tagaagtgaa    3900
atcatgtcga ggctgctgtg tgggagaaca gcttaaaata tcacaaaaaa agaatctaaa    3960
acactgtgtt gcttgtccca gaaagggaat caagtatttt tataaagatt ggagtggtaa    4020
```

```
aaatcgagta tgtgctagat gctatggaag atacaaattc agcggtcatc actgtataaa    4080
ttgcaagtat gtaccagaag cacgtgaagt gaaaaaggca aaagacaaag gcgaaaaatt    4140
gggcattacg cccgaaggtt tgccagttaa aggaccagag tgtataaaat gtggcggaat    4200
cttacagttt gatgctgtcc gcgggcctca taagagttgt ggtaacaacg caggtgcgcg    4260
catctgccgg atccccgggt taattaacgg tggaggtgga ggtggaggtg gaggtgaaca    4320
aaagctaatc tccgaggaag acttgaacgg tgaacaaaaa ttaatctcag aagaagactt    4380
gaacggactc gacggtgaac aaaagttgat ttctgaagaa gatttgaacg gtgaacaaaa    4440
gctaatctcc gaggaagact tgaacggtga acaaaaatta atctcagaag aagacttgaa    4500
cggactcgac ggtgaacaaa agttgatttc tgaagaagat ttgaacggtg aacaaaagct    4560
aatctccgag gaagacttga acggtgaaca aaaattaatc tcagaagaag acttgaacgg    4620
actcgacggt gaacaaaagt tgatttctga agaagatttg aacggtgaac aaaagctaat    4680
ctccgaggaa gacttgaacg gtgaacaaaa attaatctca gaagaagact tgaacggact    4740
cgacggtgaa caaaagttga tttctgaaga agatttgaac ggtgaacaaa agctaatctc    4800
cgaggaagac ttgaacggtg aacaaaaatt aatctcagaa gaagacttga acggactcga    4860
cggtgaacaa aagttgattt ctgaagaaga tttgaacggt gaacaaaagc taatctccga    4920
ggaagacttg aacggtgaac aaaaattaat caatcactag tgaattcgcg ccacttctaa    4980
ataagcgaat tcttgagggc cgcatcatg taattagtta tgtcacgctt acattcacgc    5040
cctcccccca catccgctct aaccgaaaag gaaggagtta caaacctga agtctaggtc    5100 cctatttatt tttttatagt tatgttagta ttaagaacgt tatttatatt tcaaattttt    5160 ctttttttttc tgtacagacg cgtgtacgca tgtaacatta tactgaaaac cttgcttgag    5220
aaggttttgg gacgctcgaa ggctttaatt tgcggccaag cttggcgtaa tcatggtcat    5280 agctgttttcc tgtgtgaaat tgttatccgc tcacaattcc acacaacata cgagccggaa    5340
gcataaagtg taaagcctgg ggtgcctaat gagtgagcta actcacatta attgcgttgc    5400
gctcactgcc cgctttccag tcgggaaacc tgtcgtgcca gctgcattaa tgaatcggcc    5460
aacgcgcggg gagaggcggt ttgcgtattg ggcgctcttc cgcttcctcg ctcactgact    5520
cgctgcgctc ggtcgttcgg ctgcggcgag cggtatcagc tcactcaaag gcggtaatac    5580
ggttatccac agaatcaggg gataacgcag gaaagaacat gtgagcaaaa ggccagcaaa    5640
aggccaggaa ccgtaaaaag gccgcgttgc tggcgttttt ccataggctc cgcccccctg    5700
acgagcatca caaaaatcga cgctcaagtc agaggtggcg aaacccgaca ggactataaa    5760
gataccaggc gtttccccct ggaagctccc tcgtgcgctc tcctgttccg accctgccgc    5820
ttaccggata cctgtccgcc tttctccctt cgggaagcgt ggcgctttct catagctcac    5880
gctgtaggta tctcagttcg gtgtaggtcg ttcgctccaa gctgggctgt gtgcacgaac    5940
cccccgttca gcccgaccgc tgcgccttat ccggtaacta tcgtcttgag tccaacccgg    6000
taagacacga cttatcgcca ctggcagcag ccactggtaa caggattagc agagcgaggt    6060
atgtaggcgg tgctacagag ttcttgaagt ggtggcctaa ctacggctac actagaagga    6120
cagtatttgg tatctgcgct ctgctgaagc cagttacctt cggaaaaaga gttggtagct    6180
cttgatccgg caaacaaacc accgctggta gcggtggttt ttttgtttgc aagcagcaga    6240
ttacgcgcag aaaaaaagga tctcaagaag atcctttgat cttttctacg ggtctgacg    6300 ctcagtggaa cgaaaactca cgttaaggga ttttggtcat gagattatca aaaaggatct    6360
```

```
tcacctagat cctttaaat taaaaatgaa gttttaaatc aatctaaagt atatatgagt   6420
aaacttggtc tgacagttac caatgcttaa tcagtgaggc acctatctca gcgatctgtc   6480
tatttcgttc atccatagtt gcctgactcc ccgtcgtgta gataactacg atacgggagg   6540
gcttaccatc tggccccagt gctgcaatga taccgcgaga cccacgctca ccggctccag   6600
atttatcagc aataaaccag ccagccggaa gggccgagcg cagaagtggt cctgcaactt   6660
tatccgcctc catccagtct attaattgtt gccgggaagc tagagtaagt agttcgccag   6720
ttaatagttt gcgcaacgtt gttgccattg ctacaggcat cgtggtgtca cgctcgtcgt   6780
ttggtatggc ttcattcagc tccggttccc aacgatcaag gcgagttaca tgatccccca   6840
tgttgtgcaa aaaagcggtt agctccttcg gtcctccgat cgttgtcaga agtaagttgg   6900
ccgcagtgtt atcactcatg gttatggcag cactgcataa ttctcttact gtcatgccat   6960
ccgtaagatg cttttctgtg actggtgagt actcaaccaa gtcattctga aatagtgta   7020
tgcggcgacc gagttgctct tgcccggcgt caatacggga taataccgcg ccacatagca   7080
gaactttaaa agtgctcatc attggaaaac gttcttcggg gcgaaaactc tcaaggatct   7140
taccgctgtt gagatccagt tcgatgtaac ccactcgtgc acccaactga tcttcagcat   7200
cttttacttt caccagcgtt tctgggtgag caaaaacagg aaggcaaaat gccgcaaaaa   7260
agggaataag ggcgacacgg aaatgttgaa tactcatact cttccttttt caatattatt   7320
gaagcattta tcagggttat tgtctcatga gcggatacat atttgaatgt atttagaaaa   7380
ataaacaaat aggggttccg cgcacatttc cccgaaaagt gccacctgac gtctaagaaa   7440
ccattattat catgacatta acctataaaa ataggcgtat cacgaggccc tttcgtcttc   7500
aagaattcag ctgaagcttc gtacgctgca ggtcgacgga tccccgggtt aattaaggcg   7560
cgccagatct gtttagcttg ccttgtcccc gccgggtcac ccggccagcg acatggaggc   7620
ccagaatacc ctccttgaca gtcttgacgt gcgcagctca ggggcatgat gtgactgtcg   7680
cccgtacatt tagcccatac atccccatgt ataatcattt gcatccatac attttgatgg   7740
ccgcacggcg cgaagcaaaa attacggctc ctcgctgcag acctgcgagc agggaaacgc   7800
tccccctcaca gacgcgttga attgtcccca cgccgcgccc ctgtagagaa atataaaagg   7860
ttaggatttg ccactgaggt tcttctttca tatacttcct tttaaaatct tgctaggata   7920
cagttctcac atcacatccg aacataaaca accatggcta agttgacctc tgctgttcca   7980
gttttgactg ctagagatgt tgctggtgct gttgaatttt ggaccgacag attgggtttt   8040
tccagagatt tcgttgaaga cgatttcgct ggtgttgttc gtgacgatgt taccttgttc   8100
atctccgccg ttcaagatca agttgttcca gataatactt tggcttgggt ttgggttaga   8160
ggtttagacg agttgtatgc tgaatggtct gaagtcgttt ctactaactt cagagatgct   8220
tctggtccag ctatgaccga aattggtgaa caaccatggg gtagagaatt tgccttgaga   8280
gacccagccg gtaattgtgt tcatttcgtc gccgaagaac aagattgatc agtactgaca   8340
ataaaaagat tcttgttttc aagaacttgt catttgtata gttttttat attgtagttg   8400
ttctatttta atcaaatgtt agcgtgattt atatttttt tcgcctcgac atcatctgcc   8460
cagatgcgaa gttaagtgcg cagaaagtaa tatcatgcgt caatcgtatg tgaatgctgg   8520
tcgctatact gctgtcgatt cgatactaac gccgccatcc agtgtcgaaa cgagctcga   8580
attcatcgat gatatcagat ccactagtgg cctatgcaat tctcatgttt gacagcttat   8640
catcgatcgt ccaactgcat ggagatgagt cgtggcaaga ataccaagag ttcctcggtt   8700
tgccagttat taaaagactc gtatttccaa aagactgcaa catactactc agtgcagctt   8760
```

```
cacagaaacc tcattcgttt attcccttgt ttgattcaga agcaggtggg acaggtgaac    8820
ttttggattg gaactcgatt tctgactggg ttggaaggca agagagcccc gagagcttac    8880
attttatgtt agctggtgga ctgacgccag aaaatgttgg tgatgcgctt agattaaatg    8940
gcgttattgg tgttgatgta agcggaggtg tggagacaaa tggtgtaaaa gactctaaca    9000
aaatagcaaa tttcgtcaaa aatgctaaga aataggttat tactgagtag tatttattta    9060
agtattgttt gtgcacttgc ctgcaagcct tttgaaaagc aagcataaaa gatctaaaca    9120
taaaatctgt aaaataacaa gatgtaaaga taatgctaaa tcatttggct ttttgattga    9180
ttgtacagga aaatatacat cgcagggggt tgactttac  catttcaccg caatggaatc    9240
aaacttgttg aagagaatgt tcacaggcgc atacgctaca atgacccgat tcttgctagc    9300
cttttctcgg tcttgcaaac aaccgccggc agcttagtat ataaatacac atgtacatac    9360
ctctctccgt atcctcgtaa tcattttctt gtatttatcg tcttttcgct gtaaaaactt    9420
tatcacactt atctcaaata cacttattaa ccgcttttac tattatcttc tacgctgaca    9480
gtaatatcaa acagtgacac atattaaaca cagtggtttc tttgcataaa caccatcagc    9540
ctcaagtcgt caagtaaaga tttcgtgttc atgcagatag ataacaatct atatgttgat    9600
aattagcgtt gcctcatcaa tgcgagatcc gtttaaccgg accctagtgc acttacccca    9660
cgttcggtcc actgtgtgcc gaacatgctc cttcactatt ttaacatgtg gaattatcga    9720
tgccggtgtt attcttgcta tgataggcca tcgaatgtta aagggaagat ttattgtttt    9780
gcccttaaaa gacgaatttg gaccgtgaat gtttaaataa ttctcatgtt tgacagctta    9840
tcatcgaact ctaagaggtg atacttattt actgtaaaac tgtgacgata aaaccggaag    9900
gaagaataag aaaactcgaa ctgatctata atgcctattt tctgtaaaga gtttaagcta    9960
tgaaagcctc ggcattttgg ccgctcctag gtagtgcttt ttttccaagg acaaaacagt   10020 ttcttttct tgagcaggtt ttatgtttcg gtaatcataa acaataaata aattatttca   10080
tttatgttta aaaataaaaa ataaaaaagt attttaaatt tttaaaaaag ttgattataa   10140
gcatgtgacc ttttgcaagc aattaaattt tgcaatttgt gattttaggc aaaagttaca   10200
atttctggct cgtgtaatat atgtatgcta aagtgaactt ttacaaagtc gatatggact   10260
tagtcaaaag aaattttctt aaaaatatat agcactagcc aatttagcac ttctttatga   10320
gatatattat agactttatt aagccagatt tgtgtattat atgtatttac ccggcgaatc   10380
atggacatac attctgaaat aggtaatatt ctctatggtg agacagcata gataacctag   10440
gatacaagtt aaaagctagt actgttttgc agtaattttt ttctttttta taagaatgtt   10500
accacctaaa taagttataa agtcaatagt taagtttgat atttgattgt aaaataccgt   10560
aatatatttg catgatcaaa aggctcaatg ttgactagcc agcatgtcaa ccactatatt   10620
gatcaccgat atatggactt ccacaccaac tagtaatatg acaataaatt caagatattc   10680
ttcatgagaa tggcccagcg atatatgcgg tgtgaaatac cgcacagatg cgtaaggaga   10740
aaataccgca tcaggcgcca ttcgccattc aggctgcgca actgttggga agggcgatcg   10800
gtgcgggcct cttcgctatt acgccagctg gcgaaagggg gatgtgctgc aaggcgatta   10860
agttgggtaa cgccagggtt ttcccagtca cgacgttgta aaacgacggc cagt         10914
```